US010661036B2

(12) United States Patent
McCullough

(10) Patent No.: US 10,661,036 B2
(45) Date of Patent: May 26, 2020

(54) METHODS AND DELIVERY DEVICES USING HERBAL EXTRACTS

(71) Applicant: Timothy McCullough, Stillwater, MN (US)

(72) Inventor: Timothy McCullough, Stillwater, MN (US)

( * ) Notice: Subject to any disclaimer, the term of this patent is extended or adjusted under 35 U.S.C. 154(b) by 497 days.

(21) Appl. No.: 15/199,366

(22) Filed: Jun. 30, 2016

(65) Prior Publication Data

US 2016/0310684 A1 Oct. 27, 2016

Related U.S. Application Data

(63) Continuation-in-part of application No. 14/574,591, filed on Dec. 18, 2014, now Pat. No. 9,380,813.
(Continued)

(51) Int. Cl.
*A61M 15/06* (2006.01)
*A24F 47/00* (2020.01)
(Continued)

(52) U.S. Cl.
CPC ........... *A61M 15/06* (2013.01); *A24F 47/008* (2013.01); *A61K 31/05* (2013.01); *A61K 31/352* (2013.01);
(Continued)

(58) Field of Classification Search
CPC .......... A61M 11/041; A61M 11/042; A61M 11/044; A61M 15/00; A61M 15/02; A61M 15/06; A24F 47/00–008
See application file for complete search history.

(56) References Cited

U.S. PATENT DOCUMENTS 3,270,437 A   9/1966 Castillo et al.
3,625,214 A   12/1971 Higuchi
(Continued)

FOREIGN PATENT DOCUMENTS

WO   WO-1994009842 A1   5/1994
WO   WO-2001076768 A1   10/2001
(Continued)

OTHER PUBLICATIONS

US 9,254,008 B2, 02/2016, McCullough (withdrawn)
(Continued)

*Primary Examiner* — Valerie L Woodward
(74) *Attorney, Agent, or Firm* — Schwegman Lundberg & Woessner, P.A.

(57) ABSTRACT

A method of purifying herbal extract(s) from an herbaceous plant composition includes heating the herbal extracts-containing composition to volatilize at least one of herbal extract(s) into a vapor and condensing the vapor on a substrate or wet extracting the herbal extract(s) by treatment of the herbaceous plant composition or a derivative thereof with a solvent for the herbal extract(s), separating the solution of herbal extract(s), forming a concentrate and casting the concentrate on the substrate to form a coating of the herbal extract(s) on the substrate. A corresponding delivery cartridge and delivery system can include a controllable heating element and the substrate coated with at least one of herbal extract(s). These are configured to allow passage of air over the substrate to volatilize or entrain the herbal extract(s) as a vapor, gas or aerosol for administration to a user.

11 Claims, 26 Drawing Sheets

Related U.S. Application Data which is a continuation-in-part of application No. 14/264,999, filed on Apr. 29, 2014, now Pat. No. 9,220,294, application No. 15/199,366, which is a continuation-in-part of application No. PCT/US2015/015445, filed on Feb. 11, 2015, which is a continuation of application No. PCT/US2015/014418, filed on Feb. 4, 2015, and a continuation of application No. 14/574,591, filed on Dec. 18, 2014, now Pat. No. 9,380,813, which is a continuation-in-part of application No. 14/264,999, filed on Apr. 29, 2014, now Pat. No. 9,220,294.

(60) Provisional application No. 61/938,577, filed on Feb. 11, 2014, provisional application No. 62/058,431, filed on Oct. 1, 2014.

(51) Int. Cl.

| | | |
|---|---|---|
| *H05B 3/03* | (2006.01) | |
| *H05B 3/34* | (2006.01) | |
| *H05B 1/02* | (2006.01) | |
| *A61M 15/00* | (2006.01) | |
| *A61M 11/04* | (2006.01) | |
| *A61K 31/05* | (2006.01) | |
| *A61K 31/352* | (2006.01) | |
| *H05B 3/42* | (2006.01) | |
| *A61K 36/28* | (2006.01) | |
| *A61K 36/38* | (2006.01) | |
| *A61K 36/53* | (2006.01) | |
| *A61K 36/537* | (2006.01) | |
| *A61K 36/54* | (2006.01) | |
| *A61K 36/752* | (2006.01) | |
| *A61K 36/82* | (2006.01) | |
| *A61K 36/9068* | (2006.01) | |

(52) U.S. Cl.
CPC .............. *A61K 36/28* (2013.01); *A61K 36/38* (2013.01); *A61K 36/53* (2013.01); *A61K 36/537* (2013.01); *A61K 36/54* (2013.01); *A61K 36/752* (2013.01); *A61K 36/82* (2013.01); *A61K 36/9068* (2013.01); *A61M 11/042* (2014.02); *A61M 15/002* (2014.02); *A61M 15/005* (2014.02); *A61M 15/0051* (2014.02); *H05B 1/025* (2013.01); *H05B 3/03* (2013.01); *H05B 3/34* (2013.01); *H05B 3/42* (2013.01); *A61M 15/0028* (2013.01); *A61M 15/0045* (2013.01); *A61M 15/0066* (2014.02); *A61M 2207/00* (2013.01); *H05B 2203/017* (2013.01)

(56) References Cited

U.S. PATENT DOCUMENTS

| | | | |
|---|---|---|---|
| 4,543,275 A | | 9/1985 | Akashi et al. |
| 4,913,865 A | | 4/1990 | Toyotama |
| 4,922,901 A | | 5/1990 | Brooks |
| 5,060,671 A | | 10/1991 | Counts et al. |
| 5,095,921 A | | 3/1992 | Losee et al. |
| 5,224,498 A | | 7/1993 | Deevi et al. |
| 5,269,327 A | * | 12/1993 | Counts ............... A24F 47/008 128/200.14 |
| 5,544,646 A | | 8/1996 | Lloyd et al. |
| 5,878,752 A | | 3/1999 | Adams et al. |
| 5,935,388 A | | 8/1999 | Meszaros |
| 6,045,864 A | | 4/2000 | Lyons et al. |
| 6,095,153 A | | 8/2000 | Kessler et al. |
| 6,270,839 B1 | | 8/2001 | Onoe et al. |
| 6,513,524 B1 | | 2/2003 | Storz |
| 6,589,395 B1 | | 7/2003 | Meili |
| 6,630,507 B1 | | 10/2003 | Hampson et al. |
| 6,909,839 B2 | | 6/2005 | Wang et al. |
| 7,025,992 B2 | | 4/2006 | Whittle |
| 7,088,914 B2 | | 8/2006 | Whittle et al. |
| 7,109,245 B2 | | 9/2006 | Kunos et al. |
| 7,132,128 B2 | | 11/2006 | Brcka |
| 7,215,878 B2 | | 5/2007 | Neumann et al. |
| 7,279,421 B2 | | 10/2007 | Suzuki |
| 7,344,736 B2 | | 3/2008 | Whittle et al. |
| 7,399,872 B2 | | 7/2008 | Webster et al. |
| 7,402,686 B2 | | 7/2008 | Duchek |
| 7,524,881 B2 | | 4/2009 | Goodwin et al. |
| 7,540,286 B2 | | 6/2009 | Cross et al. |
| 7,622,140 B2 | | 11/2009 | Whittle et al. |
| 7,651,570 B2 | | 1/2010 | Brcka |
| 7,674,922 B2 | | 3/2010 | Burdick et al. |
| 7,700,368 B2 | | 4/2010 | Flockhart et al. |
| 7,709,536 B2 | | 5/2010 | WHittle |
| 7,741,365 B2 | | 6/2010 | Makriyannis et al. |
| 7,763,311 B2 | | 7/2010 | Suzuki |
| 7,816,143 B2 | | 10/2010 | Day |
| 7,913,688 B2 | | 3/2011 | Cross et al. |
| 7,942,147 B2 | | 5/2011 | Hodges et al. |
| 8,034,843 B2 | | 10/2011 | Whittle et al. |
| 8,074,644 B2 | | 12/2011 | Hale et al. |
| 8,147,898 B2 | | 4/2012 | Coates |
| 8,161,979 B1 | | 4/2012 | Sinclair, Jr. |
| 8,387,612 B2 | | 3/2013 | Damani et al. |
| 8,481,091 B2 | | 7/2013 | Ross |
| 8,512,767 B2 | | 8/2013 | Ross |
| 8,910,630 B2 | | 12/2014 | Todd |
| 8,910,640 B2 | | 12/2014 | Sears et al. |
| 9,220,294 B2 | | 12/2015 | McCullough |
| 9,333,229 B2 | | 5/2016 | Bjorncrantz |
| 9,380,813 B2 | | 7/2016 | McCullough |
| 9,408,986 B2 | | 8/2016 | McCullough et al. |
| 9,775,379 B2 | | 10/2017 | Davidson et al. |
| 9,802,011 B2 | | 10/2017 | Davidson et al. |
| 9,839,241 B2 | | 12/2017 | Davidson et al. |
| 9,993,602 B2 | | 6/2018 | Davidson et al. |
| 10,034,990 B2 | | 7/2018 | McCullough |
| D825,102 S | | 8/2018 | Bowen et al. |
| 10,045,567 B2 | | 8/2018 | Monsees et al. |
| 10,045,568 B2 | | 8/2018 | Monsees et al. |
| 10,058,124 B2 | | 8/2018 | Monsees et al. |
| 10,058,129 B2 | | 8/2018 | Monsees et al. |
| 10,058,130 B2 | | 8/2018 | Monsees et al. |
| 10,070,669 B2 | | 9/2018 | Monsees et al. |
| 10,076,139 B2 | | 9/2018 | Monsees et al. |
| 10,080,851 B2 | | 9/2018 | Davidson et al. |
| 10,099,020 B2 | | 10/2018 | Davidson et al. |
| 10,104,915 B2 | | 10/2018 | Bowen et al. |
| 10,111,470 B2 | | 10/2018 | Monsees et al. |
| 10,117,465 B2 | | 11/2018 | Monsees et al. |
| 10,117,466 B2 | | 11/2018 | Monsees et al. |
| 10,118,006 B2 | | 11/2018 | Davidson et al. |
| 10,130,123 B2 | | 11/2018 | Hatton et al. |
| 10,159,282 B2 | | 12/2018 | Monsees et al. |
| 10,166,349 B2 | | 1/2019 | Davidson et al. |
| D842,536 S | | 3/2019 | Bowen et al. |
| 10,231,484 B2 | | 3/2019 | Bowen et al. |
| 10,244,793 B2 | | 4/2019 | Monsees et al. |
| 10,279,934 B2 | | 5/2019 | Christensen et al. |
| D857,879 S | | 8/2019 | Kurgan Itay et al. |
| 10,369,304 B2 | | 8/2019 | Davidson et al. |
| D858,745 S | | 9/2019 | Kurgan Itay et al. |
| D858,868 S | | 9/2019 | Bowen et al. |
| D858,869 S | | 9/2019 | Bowen et al. |
| D858,870 S | | 9/2019 | Bowen et al. |
| D860,523 S | | 9/2019 | Cheung et al. |
| 2002/0117175 A1 | | 8/2002 | Kottayil et al. |
| 2003/0131843 A1 | | 7/2003 | Lu |
| 2003/0221625 A1 | | 12/2003 | Toda et al. |
| 2004/0096402 A1 | | 5/2004 | Hodges et al. |
| 2004/0126326 A1 | | 7/2004 | Rabinowitz et al. |
| 2004/0138293 A1 | | 7/2004 | Werner et al. |
| 2004/0147767 A1 | | 7/2004 | Whittle et al. |
| 2005/0042172 A1 | | 2/2005 | Whittle et al. |

(56) References Cited

U.S. PATENT DOCUMENTS

| | | | |
|---|---|---|---|
| 2005/0063686 A1* | 3/2005 | Whittle | A61K 9/007 392/390 |
| 2006/0039959 A1 | 2/2006 | Wessling | |
| 2006/0160888 A1 | 7/2006 | Kottayil et al. | |
| 2006/0167084 A1 | 7/2006 | Dudley | |
| 2007/0020193 A1 | 1/2007 | de Vries et al. | |
| 2007/0041994 A1 | 2/2007 | McDowell | |
| 2007/0049645 A1 | 3/2007 | Mechoulam et al. | |
| 2007/0099987 A1 | 5/2007 | Weiss et al. | |
| 2007/0113789 A1 | 5/2007 | Brcka | |
| 2008/0057117 A1 | 3/2008 | Werner et al. | |
| 2008/0112895 A1 | 5/2008 | Kottayil et al. | |
| 2008/0181942 A1 | 7/2008 | Zajicek | |
| 2008/0216828 A1 | 9/2008 | Wensley et al. | |
| 2008/0255224 A1 | 10/2008 | Blum | |
| 2008/0262099 A1 | 10/2008 | Whittle et al. | |
| 2008/0275237 A1 | 11/2008 | Arslantas et al. | |
| 2008/0306285 A1 | 12/2008 | Hale et al. | |
| 2009/0005461 A1 | 1/2009 | Nagarkatti et al. | |
| 2009/0197941 A1 | 8/2009 | Guy et al. | |
| 2009/0324797 A1 | 12/2009 | Bobzin et al. | |
| 2010/0012118 A1 | 1/2010 | Storz | |
| 2010/0119606 A1 | 5/2010 | Whittle et al. | |
| 2010/0158973 A1 | 6/2010 | Weiss et al. | |
| 2010/0204312 A1 | 8/2010 | McAllister et al. | |
| 2010/0204443 A1 | 8/2010 | Gazit et al. | |
| 2010/0239635 A1 | 9/2010 | McClain et al. | |
| 2010/0239693 A1 | 9/2010 | Guy et al. | |
| 2010/0249223 A1 | 9/2010 | Di Marzo et al. | |
| 2010/0304391 A1 | 12/2010 | Lombard | |
| 2011/0036346 A1 | 2/2011 | Cohen et al. | |
| 2011/0052694 A1 | 3/2011 | Stinchcomb et al. | |
| 2011/0071178 A1 | 3/2011 | Makriyannis et al. | |
| 2011/0073120 A1 | 3/2011 | Adamic | |
| 2011/0082195 A1 | 4/2011 | Guy et al. | |
| 2011/0097283 A1 | 4/2011 | Van Damme et al. | |
| 2011/0240022 A1 | 10/2011 | Hodges et al. | |
| 2012/0138050 A1 | 6/2012 | Wondka et al. | |
| 2012/0304990 A1 | 12/2012 | Todd | |
| 2012/0311744 A1 | 12/2012 | Sirkowski | |
| 2013/0087144 A1 | 4/2013 | Todd | |
| 2013/0152922 A1 | 6/2013 | Benassayag et al. | |
| 2013/0178453 A1 | 7/2013 | Rohde et al. | |
| 2013/0196960 A1 | 8/2013 | Rohde et al. | |
| 2013/0255702 A1* | 10/2013 | Griffith, Jr. | A24F 47/008 131/328 |
| 2013/0276799 A1* | 10/2013 | Davidson | A24F 47/004 131/273 |
| 2013/0284192 A1 | 10/2013 | Peleg et al. | |
| 2013/0298905 A1 | 11/2013 | Levin et al. | |
| 2014/0041655 A1 | 2/2014 | Barron et al. | |
| 2014/0060554 A1 | 3/2014 | Collett et al. | |
| 2015/0075546 A1 | 3/2015 | Kueny, Sr. et al. | |
| 2015/0136158 A1 | 5/2015 | Stevens et al. | |
| 2015/0223515 A1 | 8/2015 | Mccullough | |
| 2015/0223523 A1 | 8/2015 | Mccullough | |
| 2016/0082203 A1 | 3/2016 | Mccullough et al. | |
| 2016/0286860 A1 | 10/2016 | Flayler | |
| 2016/0310682 A1 | 10/2016 | Mccullough | |
| 2016/0331035 A1 | 11/2016 | Cameron | |
| 2016/0331036 A1 | 11/2016 | Cameron | |
| 2016/0354561 A1 | 12/2016 | Mccullough | |
| 2017/0360089 A1 | 12/2017 | Davidson et al. | |
| 2018/0318529 A1 | 11/2018 | Davidson et al. | |
| 2018/0344954 A1 | 12/2018 | Davidson et al. | |
| 2019/0009039 A1 | 1/2019 | Davidson et al. | |
| 2019/0290862 A1 | 9/2019 | Davidson et al. | |

FOREIGN PATENT DOCUMENTS

| | | |
|---|---|---|
| WO | WO-2008134668 A2 | 11/2008 |
| WO | WO-2010011464 A1 | 1/2010 |
| WO | WO-2010111232 A9 | 3/2011 |
| WO | WO-2011100359 A1 | 8/2011 |
| WO | WO-2012085919 A2 | 6/2012 |
| WO | WO-2013083631 A1 | 6/2013 |
| WO | WO-2013164761 A1 | 11/2013 |
| WO | WO-2015123064 A1 | 8/2015 |
| WO | WO-2015123317 A1 | 8/2015 |

OTHER PUBLICATIONS

"Canadian Application Serial No. 2,934,983, Response filed Feb. 8, 2018 to Office Action dated Aug. 31, 2017", 35 pgs.

"Canadian Application Serial No. 2,939,088, Response filed Jan. 25, 2018 to Office Action dated Jul. 31, 2017", 126 pgs.

"U.S. Appl. No. 15/201,185, Corrected Notice of Allowability dated Jun. 29, 2018", 3 pgs.

"U.S. Appl. No. 15/201,185, Notice of Allowance dated Mar. 28, 2018", 5 pgs.

"U.S. Appl. No. 15/201,185, Notice of Allowance dated Jun. 29, 2018", 3 pgs.

"Canadian Application Serial No. 2,934,983, Office Action dated Apr. 12, 2018", 3 pgs.

"Canadian Application Serial No. 2,939,088, Office Action dated Apr. 16, 2018", 3 pgs.

"710 Pen ARK", About 710pen, [Online]. [Accessed Nov. 28, 2017]. Retrieved from the Internet: <URL: https://www.710penvape.com/pages/about-us-1>, 1 pg.

"U.S. Appl. No. 15/188,190, Supplemental Preliminary Amendment filed Nov. 27, 2017", 7 pgs.

"U.S. Appl. No. 15/201,185, Response filed Nov. 27, 2017 to Non Final Office Action dated Aug. 25, 2017", 7 pgs.

"Compare vaporizers", Storz & Bickel, [Online]. [Accessed Nov. 27, 2017]. Retrieved from the Internet: <URL: https://www.storz-bickel.com/us/en/compare/>, 4 pgs.

"Crafty", SKU 01 00 CY—Storz & Bickel, [Online]. [Accesed Nov. 28, 2017]. Retrieved from the Internet: <URL: https://www.storz-bickel.com/us/en/crafty.html>, 5 pgs.

"Crafty Vaporizer", Storz & Bickel, [Online]. [Accessed Nov. 28, 2017]. Retrieved from the Internet: <URL: https://www.storz-bickel.com/us/en/crafty/>, 4 pgs.

"Haze Vaporizer", Guest Post—Best Marijuana Vaporizers for Your Health, [Online]. [Accessed Nov. 28, 2017]. Retrieved from the Internet: <URL: https://www.marijuana.com/news/2014/12/best-marijuana-vaporizers-for-your-health/>, (Dec. 11, 2014), 11 pgs.

"The ARK by 710 Pen—Three pens, nine cartridges, ONE ARK!", Copyright 710 Pen, 2011-2014, [Online]. [Accessed Nov. 28, 2017]. Retrieved from the Internet: <URL: https://www.710penvape.com/products/the-new-710-ark-everything-you-need-in-1-kit>, 2 pgs.

"", Crafty Operating Manual, Storz & Bickel GMBH & Co. KG, (2015), 1-34.

"", Volcano Operating Manual, Storz & Bickel GMBH & Co. KG, (2015), 36 pgs.

"7 Things You Need to Know About Sativex", LeafScience, http://www.leafscience.com/2014/03/08/7-things-need-know-sativex/, (Mar. 8, 2014), 13 pgs.

"Alexza Pharamaceuticals: Staccato Platform Details", [Online]. Retrieved from the Internet: <URL: http://www.alexza.com/staccato/staccato-platform>, (Accessed on: Jun. 30, 2015), 5 pgs.

"Amazon.com: EZ Breathe Atomizer AsthmaInhalers, Model # EZ100: Health & Personal Care", [Online]. Retrieved from the Internet: <URL: http://www.amazon.com/EZ-Breathe-Atomizer-Asthma-Inhalers-EZ-100/dp/B00DQSTVRQ/ref=pd_sxp_f_pt>, (Accessed: Mar. 3, 2015), 25 pgs.

"U.S. Appl. No. 14/264,999, Non Final Office Action dated Mar. 13, 2015", 10 pgs.

"U.S. Appl. No. 14/264,999, Notice of Allowance dated Jul. 2, 2015", 8 pgs.

"U.S. Appl. No. 14/264,999, Notice of Allowance dated Nov. 9, 2015", 8 pgs.

"U.S. Appl. No. 14/264,999, Response filed Jun. 12, 2015 to Non Final Office Action dated Mar. 3, 2015", 16 pgs.

"U.S. Appl. No. 14/574,591, Non Final Office Action dated Aug. 18, 2015", 14 pgs.

(56) References Cited

OTHER PUBLICATIONS

"U.S. Appl. No. 14/574,591, Notice of Allowance dated Feb. 12, 2016", 5 pgs.
"U.S. Appl. No. 14/574,591, Notice of Allowance dated May 20, 2016", 5 pgs.
"U.S. Appl. No. 14/574,591, Notice of Allowance dated Nov. 24, 2015", 5 pgs.
"U.S. Appl. No. 14/574,591, Response filed Jun. 30, 2015 to Restriction Requirement dated May 21, 2015", 9 pgs.
"U.S. Appl. No. 14/574,591, Restriction Requirement dated May 21, 2015", 5 pgs.
"U.S. Appl. No. 14/574,591,Response filed Oct. 30, 2015 to Non Final Office Action dated Aug. 18, 2015", 44 pgs.
"U.S. Appl. No. 14/959,591, Non Final Office Action dated Feb. 1, 2016", 12 pgs.
"U.S. Appl. No. 14/959,591, Notice of Allowance dated Jun. 8, 2016", 8 pgs.
"U.S. Appl. No. 14/959,591, Preliminary Amendment filed Dec. 10, 2015", 6 pgs.
"U.S. Appl. No. 14/959,591, Response filed Apr. 29, 2016 to Non Final Office Action dated Feb. 1, 2016", 24 pgs.
"U.S. Appl. No. 15/201,185, Non Final Office Action dated Aug. 25, 2017", 8 pgs.
"Big Pharma's Weed Winner", [online]. The Daily Beast. [retireved on Apr. 29, 2014]., Retrieved from the Internet: <URL: http://www.thedailybeast.com/articles/2014/01/24/how-one-pharmaceutical-company-could-become-the-safest-and-most-trusted-of-all-cannabis-dealers.html#url=/articles/2014/01/24/how-one-pharmaceutical-company-could-become-, (Jan. 24, 2014), 19 pgs.
"Canadian Application Serial No. 2,934,983, Office Action dated Aug. 31, 2017", 3 pgs.
"Canadian Application Serial No. 2,939,088, Office Action dated Jul. 31, 2017", 3 pgs.
"Clean Your Volcano! How Often?", Volcano Vaporizer Tips n' Tricks, [Online]. Retrieved from the Internet: <URL: http://volcanotips.com/volcano/clean-your-volcano-how-often/, (Accessed Feb. 19, 2016), 4 pgs.
"Decarboxylating Cannabis: Turning THCA into THC", [online}. [retrieved on Apr. 29, 2014]. Retrievefd from the Internet: <URL: http://www.marijuanagrowershq.com/decarboxylating-cannabis-turning-thca-into-thc/>, (Aug. 14, 2012), 36 pgs.
"Decarboxylation of cannabis: scientific info about temps and times", [online]. [archived on Jul. 5, 2013]. Retrieved from the Internet: <URL: http://cannabischris.com/2012/10/decarboxylation-of-cannabis/>, (Oct. 31, 2012), 5 pgs.
"Dr. Sisley Recieves Government Grant to Research Cannabis and PTSD", [Online]. Retrieved from the Internet: <URL: https://www.cannabisreports.com/news/2014/12/17/dr-sisley-receives-government-grant-to-research-cannabis-and-ptsd/>, (Dec. 17, 2014), 10 pgs.
"Edibles in Review: LickIt Cannabis-Infused Breath Strips—Drugs Forum", [Online]. Retrieved from the Internet: <URL: https://drugs-forum.com/forum/showthread.php?t=220406>, (Accessed Apr. 26, 2016), 3 pgs.
"Evaluation of Volcano(r) Vaporizer for the Efficient Emission of THC, CBD, CBN and the Significant Reduction and/or Elimination of Polynuclear-Aromatic (PNA) Analytes Resultant of Pyrolysis", prepared by Chemic Laboratories, Canton, MA [online}. [retrieved on Apr. 29, 2014]. Retrieved from the Internet: <URL: http://www.maps.org/mmj/vaporizerstudy4.15.03.pdf>, (2003), 57 pgs.
"Hash Oil", [online]. [retrieved on Apr. 29, 2014]. Retrieved from the Internet: <URL: http://en.wikipedia.org/wiki/Hash_oil>, (last modified on Apr. 27, 2014), 4 pgs.
"Heliospectra AB hires Dr. Sue Sisley as Director of Medicinal Plant Research", Heliospectra, [Online]. Retrieved from the Internet: <URL: https://www.heliospectra.com/blog/heliospectra-ab-hires-dr-sue-sisley-director-medicinal-plant-research>, (Feb. 23, 2015), 6 pgs.
"Herbal Vaporizer, Ingesting herbs has some incredible health benefits", Natural Health Ezine, [Online]. Retrieved from the Internet: <URL: http://naturalhealthezine.com/herbal-vaporizers-an-introduction/>, (Jan. 9, 2011), 5 pgs.
"History: GW Pharmaceuticals", [Online]. Retrieved from the Internet: <URL: http://www.gwpharm.com/history.aspx>, (Accessed on: Jun. 30, 2015), 5 pgs.
"How to Use Your Inhaler", Asthma Society of Canada, [Online]. Retrieved from the Internet: <URL: http://www.asthma.ca/adults/treatment/spacers.php, (Oct. 2015), 3 pgs.
"International Application Serial No. PCT/US2015/014418, International Preliminary Report on Patentability dated Aug. 25, 2016", 10 pgs.
"International Application Serial No. PCT/US2015/014418, International Search Report dated Jun. 25, 2015", 4 pgs.
"International Application Serial No. PCT/US2015/014418, Invitation to Pay Additional Fees and Partial Search Report dated Apr. 20, 2015", 2 pgs.
"International Application Serial No. PCT/US2015/014418, Written Opinion dated Jun. 25, 2015", 8 pgs.
"International Application Serial No. PCT/US2015/015445, International Preliminary Report on Patentability dated Aug. 25, 2016", 18 pgs.
"International Application Serial No. PCT/US2015/015445, International Search Report dated May 14, 2015", 4 pgs.
"International Application Serial No. PCT/US2015/015445, Written Opinion dated May 14, 2015", 16 pgs.
"Juju Joints: Home page", [Online]. Retrieved from the Internet: <URL: http://jujujoints.com/>, (Accessed on: Jun. 30, 2015), 1 pg.
"Juju Joints: The Deets", [Online]. Retrieved from the Internet: <URL: http://jujujoints.com/deets/>, (Accessed on: Jun. 30, 2015), 3 pgs.
"Open Vape-Products: O.Penvape Battery & Charger", [Online]. Retrieved from the Internet: <URL: http://www.openvape.com/shop/shop/featured-products/o-penvape-battery.html?SID=h9susctdi7uc88huscks6je2o0>, (Accessed on: Jun. 30, 2015), 3 pgs.
"Open vape: Home page", [Online]. Retrieved from the Internet: <URL: http://www.openvape.com/>, (Accessed on: Jun. 30, 2015), 2 pgs.
"Sativex(r)", [online]. (c) 2014 GW Pharnaceuticals. [retrieved on Apr. 29, 2014]. Retrieved from the Internet: <URL: http://www.gwpharm.com/Sativex.aspx>, (2014), 2 pgs.
"Science Minus Details: Weed Science or 'Activation Explained!!'", [Online]. Retrieved from the Internet: <URL: http://www.scienceminusdetails.com/2009/04/weed-science.html, (2009), 17 pgs.
"Total Sublimation—Sublimator in Action", [online]. [retrieved on Apr. 29, 2014]. Retrieved from the Internet: <URL: http://thehighcanadian.wordpress.com/tag/total-sublimation/>, (2014), 3 pgs.
"Tutorial: Atomizer vs. Cartomizer vs. Clearomizer Overview of Atomizer vs. Cartomizer vs. Clearomizer", [Online]. Retrieved from the Internet: <URL: https://www.misthub.com/blog/tutorialatomizervscartomizervsclearomizer/>, (Accessed: Mar. 3, 2015), 15 pgs.
"Vacuum and fractional distillation", [online]. [retrieved on Apr. 29, 2014]. Retrieved from the Internet: <URL: http://boards.cannabis.com/concentrates/182951-vacuum-fractional-distillation.html>, (2014), 5 pgs.
"Vaporizer (inhalation device)", [online]. Wikipedia(r), the free encyclopedia. [retrieved on Apr. 29, 2014]. Retrieved from the Internet: <URL: http://en.wikipedia.org/wiki/Vaporizer_(inhalation_device)>, (modified on Mar. 21, 2014), 4 pgs.
"Volcano Vaporizer", [online]. (c) 2013 Storz & Bickel GMBH & Co. KG. [retrieved on Dec. 10, 2013]. Retrieved from the Internet: <URL: http://volcanovaporizer.com/about/>, (2013), 4 pgs.
"Volcano(r) Vaporization System", [online]. [retrieved on May 15, 2014]. Retrieved from the Internet: <URL: http://www.storz-bickel.com/vaporizer/volcano-technology.html>, (2014), 4 pgs.
"Why Vaporize?", [online]. (c) 2013 Storz & Bickel GMBH & Co. KG. [retrieved on Dec. 10, 2013]. Retrieved from the Internet: <URL: http://volcanovaporizer.com/whv-vape/>, (2013), 4 pgs.
Chanbers, Rachel, "Leafly: What is Dabbing and How Do Dabs Work?", [Online]. Retrieved from the Internet: <URL: https://www.leafly.com/news/cannabis-101/is-dabbing-good-or-bad-or-both>, (Oct. 28, 2013), 9 pgs.

(56) References Cited

OTHER PUBLICATIONS

Cross, Green, "THC is heat activated: Rollitup", [Online]. Retrieved from the Internet: <URL: http://www.rollitup.org/t/thc-is-heat-activated.242205/>, (Accessed Apr. 26, 2016), 7 pgs.

Doblin, Rick, "HHS Cover Letter", Multidisciplinary Association for Psychedelic Studies(MAPS), [Online]. Retrieved from the Internet: <URL: http://www.maps.org/research-archive/mmj/HHS-CoverLetter-Doblin-electronic-14Mar14.pdf>, (Mar. 12, 2014), 2 pgs.

Fraleigh, Nicholas, "Backdoor Medicine: How Cannabis Suppositories Can Save Lives—Cannabis Digest", [Online]. Retrieved from the Internet: <URL: http://cannabisdigest.ca/cannatory/>, (2014), 53 pgs.

Hazekamp, et al., "Evaluation of a Vaporizing Device (Volcano (R)) for the Pulmonary administration of tetrahydrocannabinol", Journal of Pharmaceutical Sciences.vol. 95, (Jun. 2006), 1308-1317.

Hazekamp, Arno, "", Cannabis Extracting The Medicine Hazekamp Thesis, (2007), 187 pgs.

Jimbob, "THC coated rolling papers: Cannabis.com—The World's Cannabis Site", [Online]. Retrieved from the Internet: <URL: http://boards.cannabis.com/threads/thc-coated-rolling-papers.114509/>, (Accessed Apr. 26, 2016), 7 pgs.

Mechoulam, Raphael, "Veterans for medical cannabis access: General use of cannabis for PTSD Symptoms", [Online]. Retrieved from the Internet: <URL: http://veteransformedicalmarijuana.org/content/general-use-cannabis-ptsd-symptoms>, (2010), 3 pgs.

Schwartz, Carly, "Marijuana Market Poised to Grow Faster Than Smartphones", [online]. Huffington Post. [retrieved on Apr. 29, 2014]. Retrieved from the Internet: <URL: http://www.huffingtonpost.com/2013/11/04/marijuana-market_n_4209874.html>, (2013), 6 pgs.

Wattenberg, Sarah, "Letter to Multidisciplinary Association for Psychedelic Studies (MAPS)", [Online]. Retrieved from the Internet: <URL: http://www.maps.org/research-archive/mmj/CoverletterSarahW_10-23_2013_final_forweb.pdf, (Oct. 23, 2013), 14 pgs.

Welch, William M., "Vaporizers, e-cigs of the pot world, are booming", [online]. USA Today. [retrieved on Apr. 29, 2014]. Retrieved from the Internet: <URL: http://www.usatoday.com/story/money/business/2014/03/15/marijuana-vapporizing-gains/6042675/>, (Mar. 17, 2014), 6 pgs.

Whittle, G. W, et al., "Prospect for new cannabis-based prescription medicines", Journal of Cannabis Therapeutics 3(4), (2001), 133-152.

"U.S. Appl. No. 15/118,090, Final Office Action dated Aug. 8, 2019", 7 pgs.

"U.S. Appl. No. 15/118,090, Non Final Office Action dated Dec. 14, 2018", 21 pgs.

"U.S. Appl. No. 15/118,090, Response filed Jun. 14, 2019 to Non Final Office Action dated Dec. 14, 2019", 21 pgs.

"Canadian Application Serial No. 2,934,983, Response filed Oct. 9, 2018 to Office Action dated Apr. 12, 2018", 16 pgs.

"Canadian Application Serial No. 2,939,088, Office Action dated Jan. 8, 2019", 3 pgs.

"Canadian Application Serial No. 2,939,088, Response filed Jul. 5, 2019 to Office Action dated Jan. 8, 2019", 11 pgs.

"Canadian Application Serial No. 2,939,088, Response filed Oct. 16, 2018 to Office Action dated Apr. 16, 2018", 17 pgs.

June-Wells, Mark, "Your Guide to Supercritical Extraction", Cannabis Business Times, [Online] Retrieved from the Internet on Oct. 1, 2019: <URL: https://www.cannabisbusinesstimes.com/article/your-guide-to-supercritical-extraction/>, (Mar. 2018), 7 pgs.

"U.S. Appl. No. 15/118,090, Non Final Office Action dated Feb. 24, 2020", 7 pgs.

"U.S. Appl. No. 15/118,090, Response dated Feb. 6, 2020 to Final Office Action dated Aug. 8, 2019", 10 pgs.

"The World's First Programmable Drug Delivery System", Syqe Medical, [Online] Retrieved from the Internet: <URL: https://www.syqemedical.com/>, (dated on Feb. 6, 2020), 16 pgs.

Greenberg, Tzally, "Eight Years and 83 Million Later, Syqe Medical Releases First Cannabis Inhaler", CTECH by Calcalist, [Online] Retrieved from the Internet: <URL: https://www.calcalistech.com/ctech/articles/0,7340,L-3764680,00.html>, (Jun. 20, 2019), 5 pgs.

* cited by examiner

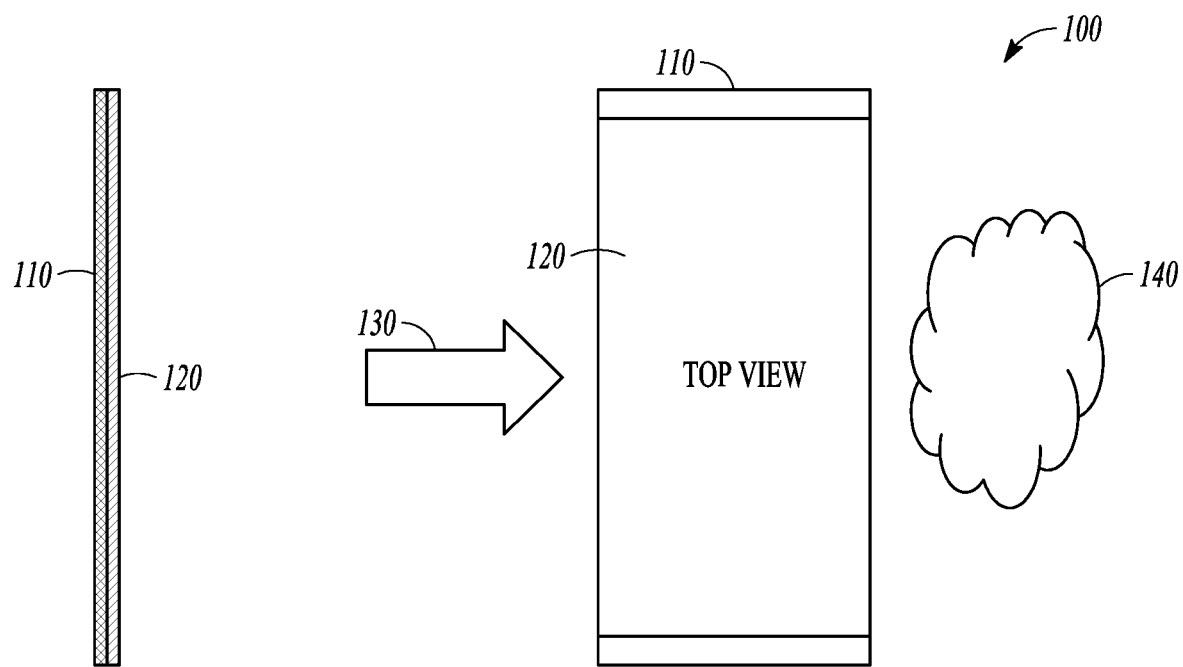
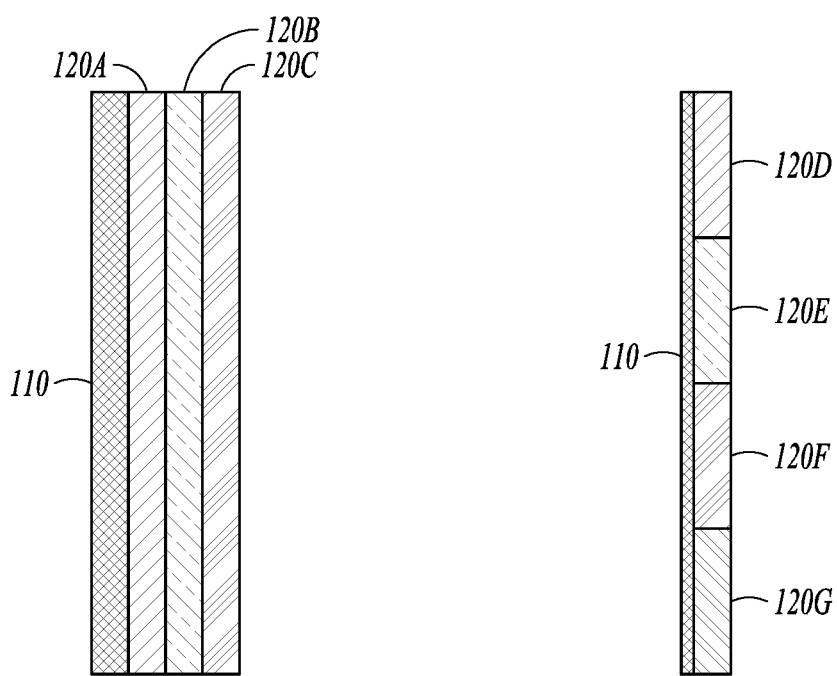
FIG. 1A  FIG. 1B
FIG. 1C  FIG. 1D

METHODS AND DELIVERY DEVICES USING HERBAL EXTRACTS

CLAIM OF PRIORITY

This application claims the benefit of priority to U.S. patent application Ser. No. 14/574,591, entitled "DRUG DELIVERY SYSTEM AND METHOD", filed on Dec. 18, 2014; and the benefit of priority to International Application Serial No. PCT/US2015/015445, entitled "METHODS AND DELIVERY DEVICES USING CANNABIS", filed on Feb. 11, 2015, each of which is hereby incorporated by reference herein in its entirety.

This application is also a continuation in part of International Application Serial No. PCT/US2015/015445, filed Feb. 11, 2015 and U.S. patent application Ser. No. 14/574, 591 filed Dec. 18, 2014 and presents subject matter common to said PCT patent application and said U.S. patent application.

TECHNICAL FIELD

The present application relates to methods and devices using herbal extracts, and more particularly, to methods of purifying herbal extract(s) from herbaceous plants with naturopathic and/or medicinal properties to create delivery products containing herbal extracts useful for naturopathic and/or human beneficial purposes.

BACKGROUND

Herbal extracts, otherwise known as botanical medicines, are derived from naturally occurring herbaceous plants by extraction from the seeds, berries, stems, branches, leaves, bark, roots or flowers or other parts of the plants. Herbal extracts are well known for medicinal purposes dating back to ancient Chinese and Egyptian writings. Herbaceous plants also constitute a source for development of modern pharmaceutical medicines and herbal extract(s) ranging from the development in the late 1800's of aspirin, a derivative of the silver willow bark, to the development in the 1980's of paclitaxel, a terpene derivative of the yew bush. When used as medicinals, herbal extracts can provide numerous benefits and can be used, for example, to treat pain, cancer, muscle spasm, depression, viral and bacterial infection, nausea, cardiovascular problems, lung problems, joint and osteoporosis problems, blood clots and other physiological problems.

Herbal extracts traditionally are administered by oral, topical, inhalation and/or injection methods. Inhalation of vaporized herbal extracts is a common form of administration. However, the traditional methods do not control dose or timing of the delivery. Moreover, traditional methods do not utilize purified extracts so that the herbal extracts typically contain plant side products, carcinogenic substances and other deleterious plant substances. Furthermore, in some circumstances, the vapors of the medicinal herb plant material are inhaled by burning the plant material, in other words by smoking. The combustion of the plant material can also release many toxic substances such as ammonia and hydrogen cyanide that can cause tissue damage if ingested. Ingestion of foods laced with herbal extracts material can also deliver herbal extract(s) to the body. However, undesirable materials in the herbal extracts are also ingested and the dosages of the ingested herbal extract(s) can be inconsistent and hard to determine.

Isolation and purification of herbal extract(s) from herbaceous plants can be of great interest and benefit to the medical community. A way to purify herbal extract(s) from herbaceous plants and convert the purified forms into an easily-ingestible form and/or to administer such purified forms or derivatives thereof is desired.

GOALS OF THE INVENTION

There is an opportunity for an herbal extract(s) delivery product that allows for inhalation of herbal extract(s) without inhaling other undesirable components found in raw herbaceous plants or created by burning the raw plant material. The amount and purity of herbal extract(s) in the delivery product can be controlled for dosage. The delivery product can be formed using a separation and coating process, as described herein, that facilitates controlled deposition of herbal extract(s) onto a substrate to form the delivery product.

SUMMARY OF THE INVENTION

The present invention is directed to methods for purifying herbal extract(s) from herbaceous plant material; providing substrates containing or incorporating the purified herbal extract(s); and providing apparatuses for delivery of herbal extract(s) to patients and consumers.

In a first aspect of the invention, the method is directed to controlled volatilization or wet extraction of the herbal extract(s) from herbaceous plant material, that is preferably comminuted, and absorption, adsorption, deposition or otherwise combining the volatilized or extracted herbal extract(s) with a substrate. When an individual herbal extract is obtained by volatilization, the substrate is held at a temperature to assure capture of the volatilized herbal extract by its condensation on the substrate (preferably cooled). When an individual herbal extract is obtained by wet extraction, a concentrate of the herbal extract in solvent is deposited onto the substrate with evaporation to form a dried layer on the substrate.

A second aspect of the invention is directed to the substrate with deposited herbal extracts. The substrate with herbal extract(s) is constructed and configured to enable release of the herbal extract(s) upon controlled heating. This aspect can include controlled release of the herbal extract(s) so as to provide regulated, controlled, limited doses of herbal extract(s) over time.

In a third aspect of the invention, the substrate with deposited herbal extract(s) is converted into a delivery cartridge. The delivery cartridge can be used with a controllable heating element to volatilize or entrain as a vapor or aerosol the herbal extract(s) and inhale the vapor or aerosol.

A fourth aspect of the invention is directed to a delivery system which can include a delivery cartridge described above. In an example, the delivery cartridge can include a cylindrical structure extending in a longitudinal direction and formed from an electrically conductive material. The cylindrical structure can include multiple electrodes extending laterally across the substrate at respective longitudinal locations. Each of the electrodes has an electrical resistance small enough to conduct current laterally along the substrate without heating the cylindrical structure. The cylindrical structure can include at least one substrate portion extending longitudinally between a respective pair of electrodes. Each substrate portion can have an electrical resistance high enough to conduct current longitudinally between the electrodes and resistively heat the respective substrate portion in response to the current conducted there through. A dose of an herbal extract(s) can be disposed on each substrate portion and configured to volatilize into a gas or vapor or entrain into an aerosol in response to the resistive heating of the respective substrate portion.

A fifth aspect of the invention is directed to the configuration and construction of the herbal extract(s) on the substrate. If multiple extracts are present, they may be arranged as overlapping layers or as segregated layers on the substrate. If the layers are overlapping, they may be arranged in any order and preferably are arranged with the herbal extract having the lowest volatilization or entrainment temperature as the top layer and the herbal extract having the highest volatilization or entrainment temperature being the bottom layer next to the substrate. With the overlapping arrangement, volatilization or entrainment is accomplished by controlling the temperature in increasing stages. With the segregated arrangement, volatilization or entrainment is accomplished by a series of heating elements, each of which is controlled to produce the appropriate volatilization or entrainment temperature for the corresponding herbal extract of the segment.

A sixth aspect is directed to an apparatus and method for producing herbal extract(s) from the raw herbaceous plant material and depositing the herbal extract(s) on the substrate. The apparatus includes a component for comminution of the herbaceous plant material, a component for controlled heating of the comminuted plant material to volatilize the herbal extract, and a cooled substrate on which the volatilized herbal extract is condensed and deposited.

A supplement of this aspect includes a cooled transport belt in place of the substrate. The volatilized herbal extract is condensed and deposited on the transport belt. A knife scraper or other remover apparatus is positioned to remove the herbal extract from the belt which is preferably heated so as to place the herbal extract to a liquid state. A transport mechanism, preferably heated, deposits the herbal extract appropriately on the substrate at a relatively close location. The appropriate deposit of the herbal extract is preferably controlled so as to deposit a unit dose of the herbal extract on the substrate, the apparatus being capable of continuously preparing substrate pieces with purified extract having the dimensions suitable for use in the delivery system.

A seventh aspect is directed to a method for wet extraction of the herbal extract(s) from the herbaceous plant material. The herbaceous plant material is comminuted to provide very small particles and the particles optionally dried in air to remove water within the plant material. The dried particles are combined with a solvent in which the herbal extract is soluble and agitated or otherwise mixed to extract into the solvent the herbal extract and produce a solution. The solution is filtered, optionally treated with activated charcoal and optionally chromatographed or fractionally distilled or optionally crystallized to further purify the herbal extract. Either following the optional purification steps or without use of these steps, the herbal extract in solvent is concentrated to produce a concentrate. The concentrate may be deposited with evaporation on the substrate to form a dried layer or coating of herbal extract on the substrate. Optionally the concentrate may be treated with a non-solvent for the herbal extract to crystallize the herbal extract or "oil out" the herbal extract as an amorphous solid. The solid may be filtered, dried and may be directly deposited or otherwise cast on the substrate. The substrate with solid may be optionally heated to liquefy or otherwise convert the solid into a contiguous layer of herbal extract on the substrate. The so-coated substrate is used as described above to form a delivery cartridge and subsequently a delivery system.

This Summary is intended to provide an overview of subject matter of the present patent application. It is not intended to provide an exclusive or exhaustive explanation of the invention. The Detailed Description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1A is a side view of an example of a single herbal extract coated substrate in accordance with the present invention.

FIG. 1B is a top view of a substrate coated with herbal extract(s) of FIG. 1A.

FIG. 1C is a side view of an example of a multilayer herbal extract coating on a substrate in accordance with the present invention.

FIG. 1D is a side view of an example of a substrate with a segregated multi-coating herbal extract.

DEFINITIONS

Figure 2:
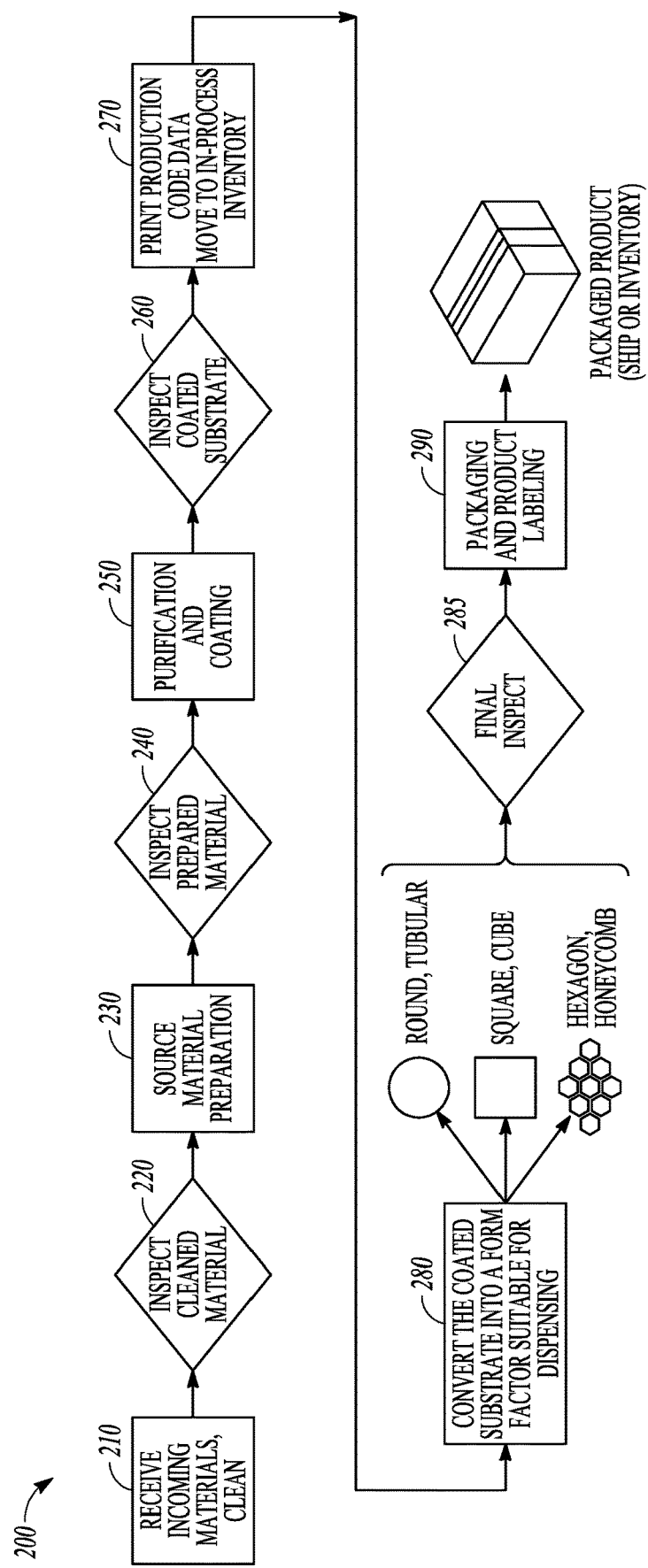
FIG. 2 is a block diagram of an example of a process for making a delivery cartridge in accordance with the present invention.

The following terms as used herein according to the invention have the following meanings.

The terms "herbs" and "herbaceous plants" in the singular and plural are understood to mean all kinds of plants, funguses and algae that can contain or can produce substances that have a pharmacological, physiological, beneficial, sensory or other perceived or un-noticed but measurable effect on humans. The term herbaceous plant includes the stems, seeds, buds, roots, leaves, branches, bark, flowers fruit and all other parts of a plant. Preferably, these parts may be selected to provide only the plant part containing the desired herbal extract if appropriate. The term "herbaceous plant material" is understood to mean comminuted herbaceous plant material unless in context this term describes a whole plant.

As used herein pursuant to the invention, an "herbal extract" and/or "extract" are understood to mean a substance or derivative thereof obtained directly from an herbaceous plant or indirectly through synthetic methods applied to such plants and/or substances. An herbal extract can be a solid, oil or liquid and can have a pharmacological, physiological, beneficial, sensory or other perceived or unnoticed but measurable effect on humans (e.g., an unnoticed but measurable effect may be, but is not limited to, lowering of blood pressure). In addition to the popular understanding that an herbal extract is a flavor, taste and odiferous substance for use in foods, the term herbal extract(s) and related terms used herein include medicinal agents and substances, pharmacological agents and substances, and chemical agent, substances and compounds known or derived from any kind of plant, fungus or algae. Included also are semi-synthetic derivatives of such substances. The term "herbal extract(s)" includes any of the phrases "one or more herbal extracts" an "herbal extract or extracts", and herbal extract, in other words, the singular herbal extract and the plural herbal extracts, i.e., multiple herbal extracts As used herein according to the invention, the terms "volatilize" and/or "volatilization" are understood to mean vaporization of an herbal extract from an herbaceous plant, which is either a liquid or a solid and is vaporized to a gas or vapor phase. In an example, one or more herbal extracts described herein may start as a solid or an oil and be heated such that the one or more herbal extracts vaporize. The one or more herbal extracts may transition directly from the solid to the gas phase, a sublimation process, or the one or more herbal extracts may become a liquid and then vaporize to a gas. In an example, the one or more herbal extracts described herein may be in a liquid or solid form prior to heating.

As used herein according to the invention, the terms "entrain", "entraining" and/or "entrainment" are understood to mean formation of a solid-gas mixture such as a solid-gas aerosol with air in which a solid, oil or liquid herbal extract is heated to an extent that it forms microparticles or microdroplets of liquid dispersed and/or mixed in a gas such as air. The common form of such a dispersion is a particulate-gas aerosol or a liquid droplet-gas aerosol. The entrainment does not require the herbal extract to vaporize into a gaseous state but instead to form an aerosol.

DETAILED DESCRIPTION

The present application relates to methods of purifying the herbal extract(s) from herbaceous plant material by heating the herbaceous plant material to vaporize the herbal extract(s) and condensing the vapor onto a substrate to form a substrate coated with herbal extract(s). Alternatively, the herbaceous plant material can be wet extracted with an appropriate solvent to produce solution of herbal extract in solvent. The solution can be concentrated to produce a concentrate and the concentrate can be deposited on a substrate and dried to produce a substrate coated with herbal extract. With either technique, multiple overlapping or segregated layers of one or more herbal extracts can be deposited on the substrate.

The coated substrates can be converted into various three-dimensional structures configured for use as a delivery cartridge. The delivery cartridge can be heated and air or inert gas can be passed through the cartridge, thus volatilizing as a vapor or entraining as an aerosol the herbal extract(s) in the delivery cartridge such that the user can inhale the herbal extract(s) for a medicinal effect and/or therapeutic effect and/or beneficial effect. The purity and ratios of herbal extract(s) in the delivery cartridge can be controlled based on the desired composition, and the quantities of herbal extract(s) can be controlled based on the desired dosage. Based on the processes used to form the coated substrates, undesirable components in the herbaceous plant material are not included in the delivery cartridge. The delivery cartridges described herein can be used with various types of delivery devices to aid in inhalation of the herbal extract(s)

The delivery cartridge can be a cylindrical structure extending in a longitudinal direction and formed from a substrate of an electrically conductive material. Electrodes can extend laterally across the substrate at respective longitudinal locations. The electrodes can each have an electrical resistance small enough to conduct current laterally along the substrate without heating the cylindrical structure. One or more substrate portions can have an electrical resistance sufficient to conduct current longitudinally between the electrodes and resistively heat the substrate portions. Herbal extract(s) can be disposed on the substrate portions and configured to volatilize or aerosolize or entrain in response to the resistive heating of the substrate portions. The cylindrical structure or other type of delivery cartridge can be used in various types of delivery systems.

With reference to the figures, details of examples and aspects of embodiments of the invention are described. The descriptions of the examples and aspects do not limit the scope of the invention.

FIGS. 1A and 1B show side and top views of an example of a coated substrate 100 of the present disclosure. The coated substrate 100 can include a substrate component 110 onto which an herbal extract(s) component 120 can be deposited. The coated substrate 100 can be exposed to heated air 130, and the herbal extract(s) component 120 can be volatilized and/or entrained in the heated air 130 to form a vapor, an aerosol or a gas-particulate mixture in which the herbal extract(s) 140 is present. The vapor or aerosol 140 can then be ingested by a user to induce a medicinal or therapeutic effect on the user.

FIGS. 1C and 1D respectively show the side views of an example of a substrate with a multi-layer overlapping herbal extract coating and an example of a substrate with a multi-layer segregated multi-layer herbal extract coating. Substrate 110 is coated with overlapping layers (120A, B and C) or segregated layers (120D, E, F and G) respectively. The layers can be exposed to air heated in stages to increase the air temperature or can be electrically heated in stages to raise the temperature of the layers and volatilize or entrain simultaneously or sequentially the multiple herbal extracts.

The substrate component 110 can be constructed from any naturally-occurring material or any man-made material, such as an FDA-approved polymer for the delivery of one or more herbal extracts, or any combination of naturally-occurring and/or man-made materials. The material selected for the substrate component 110 is inert at the heating temperatures described below for forming the coating on the substrate and the heating temperatures for later imbibing, inhaling, ingesting or otherwise administering the one or more herbal extract(s) components from the coated substrate. In an example, the substrate component 110, can include, but is not limited to, materials where the substrate component 110 can be elastic, flexible, resilient, permanently deformable or plastically deformable.

For examples including resistive heating of the substrate, the substrate may be electrically conductive such as a metal including aluminum or an electrically conductive organic polymer such as high temperature polyethylene, polypropylene or polycarbonate or polyacrylate or similar polymers preferably doped to make the polymer(s) electrically conductive, as well as inorganic (e.g. silicone) polymers. The resistive potential of the substrate will be sufficient to generate heat and volatilize or cause entrainment of the herbal extract(s).

In an example, the substrate component 110 can assume the form of any three dimensional structure, including, but not limited to, a sheet, a mesh, or any combination of three dimensional structures. Other types of structures can be employed without departing from the present subject matter of the invention. In an example, the substrate component 110 can be a sheet of polymer material. In an example, the substrate component 110 can be a sheet of aluminum mesh, a sheet of solid aluminum or a combination of both aluminum mesh and aluminum sheet. As used herein, the term aluminum can include all grades of aluminum and aluminum alloys. Materials suitable for use as the substrate component 110 are also described below in reference to FIG. 3.

As described further below, the substrate component 110 can be formed into a variety of three-dimensional shapes to form a deliver cartridge with herbal extract(s). In an example, the delivery cartridge can be designed to maximize the surface area of the herbal extract(s) component 120 exposed to the flow of heated air 130. In an example, the substrate component 110 can be shaped into forms including, but not limited to, a cone, a tube or tubular structure. As used here, a tubular structure can include any structure with an open cross-sectional area shape, a closed cross-sectional area shape, or a combination of open and closed cross-sectional area shapes. In an example, the cross-sectional area shapes can include, but are not limited to, circles, ovals, ellipses, squares, rectangles or other polygonal shapes. In an example, the cross-sectional area shapes can be open or closed shapes. Other types of structures can be employed without departing from the present subject matter.

The herbal extract(s) component 120 can include any substance or agent having a pharmaceutical, physiological, medical, beneficial, sensory, perceived or unperceived but measurable effect upon a human. The substance or agent may be present in an herbaceous plant material or in a semi-synthetic derivative of plant material. In an example, the herbal extract component 120 can include one or more active components for medicinal purposes, physiological action or therapeutic effect. In an example, the herbal extract component 120 can include one or more extracts found in herbaceous plant material, including one or more of the plant materials such as herbal extracts of herbaceous plants. As discussed above, herbaceous plants in the context of the invention include spice and flavor producing plants, flowering plants, trees, bushes fungus, algae, medicinal agent plants, alkaloid producing plants, complex hydrocarbon producing plants and any kind of plant that has been found to contain or produce an organic compound that has a pharmacological, physiological, beneficial, naturopathic, sensory or other desired effect on a human. The herbal extracts may be polycyclic hydrocarbons, heterocycle compounds, saturated and unsaturated poly-hydrocarbon acids and esters, purines, pyrimidines, alkaloids, terpenes, steroidal compounds such as budesonide, mometasone or fluticasone, macrocycles, anti-infectives, naturally occurring esters, naturally occurring acids, naturally occurring amines, naturally occurring amides, naturally occurring Schiff bases and combinations and semi-synthetic derivatives thereof. These extracts may exhibit such therapeutic or physiologic effects as bronchodilator, cardiovascular, antibacterial, anti-infective, anti-viral, mucolytic, psychological, endocrine, gastrointestinal, digestive, anti-asthmatic, cardiopulmonary, renal, urogenital, reproductive, anti-conceptive, central nervous system, sympathetic and parasympathetic nervous system effects, skin, cranial-sinus, and other pharmacological effects. These therapeutic, pharmacological and/or physiologic effects are known attributes of the herbal extracts. Administration of herbal extracts that are controlled substances such as opiates and/or have significant pharmacological and/or physiological effects should be accomplished only under the guidance and wisdom of a registered M.D. or D.O. physician, nurse practitioner or physician's assistant who is qualified and licensed to prescribe such substances. In addition, purchase and use of such controlled substances made pursuant to aspects of this invention should only be made under the supervision and licensure of qualified pharmacists.

As an example, the herbaceous plants may be selected from the group consisting of damiana, blue lotus, mullein, *Lobelia*, peppermint, spearmint, catnip, thyme, sage, wild dagga, lavender, rosemary, *Salvia divinorum*, basil, lemon balm, hops, yerba mate, calea zacatechichi, chamomile, ashwagandha *Eucalyptus*, passion flower, St John's wart, valerian, *Astragalus, Avena sativa*, kinnikinnick, cacao, chago, cinnamon, nutmeg, mace, *Cordyceps*, Don Quai, Gotu Kola, ginger root, *Ginseng*, green tea, kava, maca, moringa leaf, mullein, sacred pink lotus, red raspberry, *Rhodiola*, rooibos, tong kat ali, vanilla, yohimbine, garlic, turmeric, nutmeg, capsaicin, rosemary, *Cannabis*, coniferous trees, yew bush, willow tree, aspen tree, blood root, opium poppy, *Atropa belladonna*, strychnine, *Vinca rosea*, coffee plant, cacao tree and beans (chocolate), coca plant (cocaine), *Nicotinaa tabacum, Camelia sinensis*, monkshood, castor oil, henbane, calabar bean, *Digitalis* sp, autumn *Crocus*, peyote, *Amanita*, orange, lemon, and similar known herbaceous plants in which useful herbal extracts are known to be present. Some of these herbal extracts can be obtained commercially as they have previously been extracted for the herbaceous plant materials. Still others have been synthetically derivatized to form semi-synthetic compounds. The most useful forms of such herbal extracts and semi-synthetic compounds are the free base or free acid forms or neutral, uncomplexed forms. These forms lend themselves to volatilization and/or molecular entrainment as vapors and/or aerosols. The salt forms of bases and acids as well as complexed forms of neutral compounds can preferably be converted into the non-salt and/or non-complexed forms for use according to the invention.

The extracts of herbal plant material can exist in several parts of the plant including, but not limited to, leaves, stem, roots, branches, bark, flower, flower buds and/or fruit or seeds. In an example, the herbaceous plant material can include components such as all of the foregoing parts of a plant. As used herein, herbaceous plants can refer to plant material that has been harvested but is otherwise unprocessed. In an example, the plant material such as leaves, stems, bark, branches, seeds, roots, flowers and/or fruit can be shredded, chopped or otherwise comminuted to increase the surface area of the material in preparation for purification. In an example, the desired herbaceous material can include small particles produced by comminution. In an example, the herbal extract can be obtained by solvent extraction treatments or volatilization treatments or fractional distillation treatments of the comminuted herbaceous material.

Multiple references are made herein to a starting material of herbaceous plant material. It is recognized that any herbaceous plant composition can alternatively be used in the descriptions and examples below. Some of the processing steps, such as the separation or purification step, may vary depending on whether herbaceous plant material or an alternative form of an herbal plant material composition is used.

FIG. 2 shows an example of a process 200 that can be used to form a delivery product containing herbal extract(s), also referred to herein as a delivery cartridge. In an example, the delivery product includes herbal extract(s). In the process 200, a pre-processing step 210 can include receiving source material, such as, for example, raw herbaceous plant material. In an example, the pre-processing step 210 can include collection of raw herbaceous material from growers for use as source material and removal of undesirable organic and inorganic components from the source material. In an example, the source material can be a whole plant as discussed above or appropriate parts of the plant known to contain the desired herbal extract(s).

A first inspection step 220 can include examination of the source material for general suitability in the process 200. In an example, source material that is diseased or not otherwise of a specified quality can be removed from the source material before further processing.

A source material preparation step 230 can further prepare the source material for later steps in the process 200. In an example, the source material preparation step 230 can include the use of equipment and methods to increase the surface area of the source material, such as by shredding, chopping or otherwise comminuting, to aid in a purification process.

A second inspection step 240 can include examination of source material to ensure that the source material has been suitably processed. In an example, source material that has been improperly shredded or chopped may be rejected or redirected for further processing.

A purification and coating step 250 can include a process for separating the herbal extracts component 120 of FIG. 1 from the herbaceous plants. The purification in step 250 can include heating the pre-processed plant material to volatilize the herbal extract(s). Specific steps can depend on the form of the herbaceous plant material. Under step 250, the volatilized herbal extract(s) can then be condensed onto a carrier material to form a substrate coated with the herbal extract(s). In an example, the condensation of volatilized herbal extract(s) on a carrier material such as a substrate or on a cooled transport device can be accomplished through cooled absorption or cooled adsorption of the volatilized herbal extract. The purification and coating step can also be practiced multiple times or simultaneously practiced with multiple apparatuses to produce multiple herbal extracts deposited as overlapping layers or segregated layers on the substrate.

Alternatively, the purification and coating step 250 can include an extractive process for separating the herbal extract from the herbaceous plants. The appropriate plant material, e.g., the whole plant or selected plant parts such as flowers, seeds, buds, leaves, stems, branches, bark and/or roots, may be comminuted into very small particles. The small plant particles may be extracted with a solvent in which the desired herb extract is soluble to form an extract solution. In some examples, the solvent may be water while in others it may be ethyl alcohol, chloroform, supercritical carbon dioxide or a hydrocarbon. The extract solution may be decolorized with activated charcoal and/or further purified by column chromatography on diatomaceous earth or silica gel or other suitable known chromatographic support material, for example. The purified extract solution may be concentrated by substantial but not complete evaporation of the solvent to form a concentrate. The concentrate may be parsed onto the substrate and the remaining solvent evaporated to deposit the purified herbal extract on the substrate. Also, if the herbal extract is commercially available, it may be purchased in purified form and formulated in a minimum amount of appropriate solvent to form a concentrate as discussed above. The subsequent steps to form the purified herbal extract on the substrate may be carried out as described above. If multiple overlain layers of herbal extract are to be formed, subsequent layers may be deposited on top of previous layers by flash evaporation. As the subsequent concentrate is laid down over a previous layer, a flow of air or inert gas at a temperature to instantly evaporate the solvent is applied. The result is deposition of dry herbal extract and avoidance of comingling of the various layers that might result from solvent dissolution.

A third inspection step 260 can include examination of substrate coated with the herbal extract(s) for coating uniformity or other predetermined parameters.

A first post-processing step 270 can include identification and handling of the substrate coated with one or more herbal extracts. In an example, the coated substrate with herbal extract(s) can be marked or labeled for quality assurance and material handling purposes, such as delivery to inventory of the substrate coated with one or more herbal extracts. In an example, steps 260 and 270 can be skipped and the coated substrate from step 250 can go directly to step 280 for converting.

A conversion step 280 can include transforming the coated substrate with herbal extract(s) into forms convenient for consumption by an individual user. In an example, the conversion step 280 can include converting the substrate coated with herbal extract(s) into segments and forming the segments into delivery products or cartridges. In an example, the cartridge is constructed to maximize the volatilization or entrainment surface area of the coated substrate while minimizing packaging volume of the cartridge. In an example, the cartridge can be of a generally tubular form and assume any cross-sectional shape without altering the effect of the cartridge. In an example, the cross-section shape can include, but is not limited to, a circle, a square, a hexagon, a polygon or any symmetric or non-symmetric cross-sectional profile. Other types of shapes can be employed without departing from the present subject matter.

A fourth inspection step 285 can include examination of the cartridges to ensure that the cartridges have been suitably processed. In an example, the fourth inspection step 285 can include examination of the user shapes for visual uniformity or other parameters.

A second post-processing step 290 can include packaging and labeling of the cartridges. In an example, each cartridge can be wrapped as an individual unit. In an example, individual units can be labeled for quality assurance and governmental tax purposes.

In an example, all the aforementioned steps of the process 200 can be subject to standard manufacturing control techniques.

Figure 3:
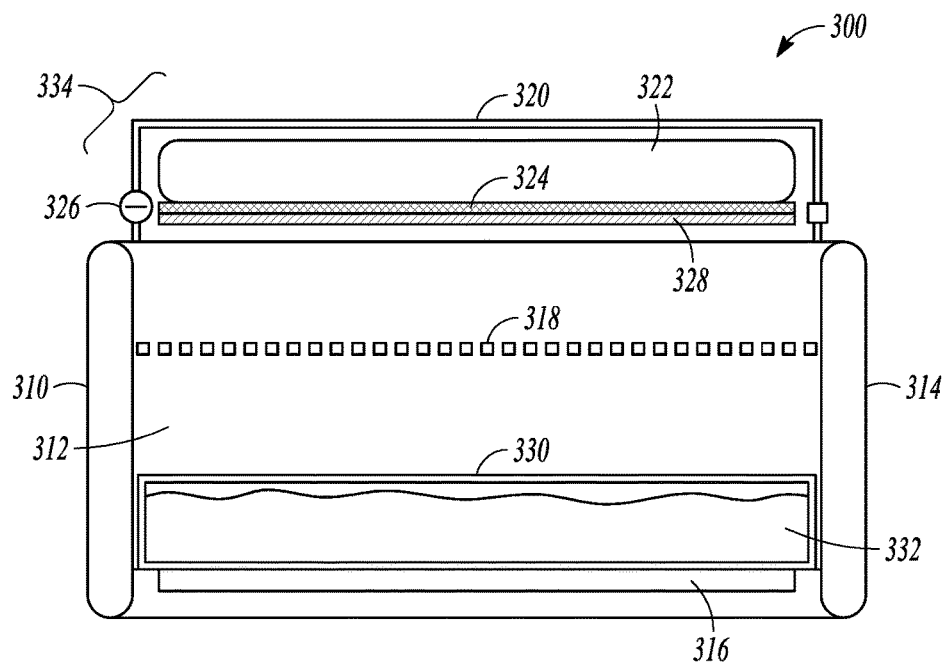
FIG. 3 is an example of a heating chamber having a batch substrate coating process for creating a coated substrate in accordance with the present invention.

FIG. 3 shows an example of a heating chamber 300 of the present disclosure for use in a single sheet substrate coating process when the herbal extract can be volatilized from the herbaceous plant material. The heating chamber 300 can include a container box 310 and a container cover 320 that can be removably attached to the container box 310. The container box 310 can include an interior surface 312, an exterior surface 314 and a controlled heat source 316 located along an interior surface 312 of the container box 310. A removable tray 330 to contain a source material (plant material) 332 can be located against an interior surface 312 of the container box 310. A removable screen 318 can be located in the container box 310 between the removable tray 330 and the container cover 320 to contain source material 332.

The container cover 320 can include a hinge 326 to attach the container cover 320 to the container box 310 and a cooling bar 322 to which a substrate 324 can be located in close proximity or removably attached. In an example, the substrate 324 can be removably attached to the cooling bar 322 with clips or similar attachment aids.

The substrate 324 can be covered with a coating 328 of herbal extract(s) using, for example, a heating process. In an example, herbal extract(s) can be deposited on the substrate by sequential processing of the appropriate herbaceous plant materials. The depositions may overlay the respective multiple extract layers on top of each other or may segregate the layers on the substrate. The controlled heat source 316 can be initiated to heat the source material 332 to a selected temperature. Depending on the selected temperature, herbal extract(s) can volatilize from the source material 332. The substrate 324 can be cooled through conduction (when in contact with the cooling bar 322) or radiation (when located in close proximity to the cooling bar 322) and the vapors generated during the heating process can condense onto the substrate 324 to form a coating 328 on the substrate 324. In an example, the herbal extract(s) can be absorbed and/or adsorbed within and/or on the substrate 324. In an example, the herbal extract(s) can be adsorbed onto the surface of the substrate 324 so as to produce a substrate coated with herbal extract(s). As used herein, a coated substrate 334 can refer to a combination of the substrate 324 and the coating 328 formed thereon.

In an example, the heating chamber 300 can be used to volatilize herbal extract(s) in the herbaceous plant material. Using the steps above, the desirable components, i.e., one or more herbal extracts, can be sequentially extracted and purified from the herbaceous plant material by controlling the temperature in the heating chamber and sequentially adding appropriate herbaceous plant material containing the desired herbal extracts. As described further below, various one or more substrates coated with herbal extracts can be formed that have one or more herbal extracts, in purified form, and contain minimal to no undesirable components.

The volatilization of the herbal extract in the heating chamber 300 can be based on the known volatilization temperature of particular herbal extract desired. Depending on a temperature that the herbaceous plant material is heated to, herbal extract(s) can be volatilized if more than one is present in the composition. Typically, the temperature of the heating chamber may approach the known volatilization temperature of the desired herbal extract. However, maintaining a slightly, to somewhat, lower chamber temperature can be utilized to assure primary production of the desired herbal extract in substantially purified form. Use of the partial vapor pressure of the herbal extract at a temperature below its volatilization temperature can be practiced to assure at least in part the production of substantially purified herbal extract.

Care is practiced to avoid combustion of the cellulosic and other materials of the herbaceous plant composition. While not a required condition for volatilization and deposition, applying a vacuum to the heating chamber can facilitate volatilization of the herbal extract at lower temperatures while not also producing undesirable substances or causing combustion. Preferably, the heating with or without partial vacuum is conducted under an inert atmosphere, such as a nitrogen or argon atmosphere. This aspect also is helpful for avoidance of plant combustion.

Water is almost always present in such plant material. Consequently, the herbaceous plant material can be pre-dried at ambient to slightly elevated temperatures to remove water.

In general, the temperatures at which each of herbal extract(s) can volatilize relative to their known volatilization temperatures in isolated, pure states are not necessarily precisely known and can depend, for example, on the surrounding conditions, the degree of comminution, the pre-drying removal of water and the particular plant part containing the herbal extract. The heating chambers described above can be used to heat the herbal extracts-containing composition to any given temperature. The particular temperature or temperature range selected can depend on multiple factors, including, for example, a particular composition of the raw herbal extracts or the desired composition of the coated substrate. Samples of the deposited or cooled vapors can be collected, at all or some of the temperature intervals, to analyze the fractions and determine the composition of the coating. Based on the results, the temperature range sufficient for volatilization can be determined or adjusted based on the desired composition of the coating. It is recognized that the temperature range can depend on the starting material and how tightly the composition of the coating is to be controlled. The composition of the starting material can vary from batch to batch and can depend, for example, on where and how the raw herbaceous plants are grown, and cleaning of the raw herbaceous plants or other preparation steps, prior to processing.

Practice and variation of these parameters are well within the ordinary and routine skill of a chemical technician to achieve the desired volatilization. The following discussion examines these parameters.

A composition of the coated substrate 334, including a purity of the herbal extract(s) can be a function of the source material used in the heating process. In an example, the grade of herbaceous plant used as the source material, such as the species and source of supply, can influence the composition of the coated substrate 334, including varying levels of one or more herbal extracts. In an example, the pre-processing of the source material, such as the size of particle resulting from shredding and chopping of the source material, can influence the composition of the coated substrate 334. In an example, sampling can be performed on the source material to determine a composition of the source material. Specification parameters and standard processing control can be implemented for monitoring and controlling the composition of the source material and the coated substrate 334.

The composition of the coated substrate 334 can be a function of the control parameters used in the heating process. In an example, the temperature and partial pressure (i.e., partial vacuum) of the chamber, the total time the source material is exposed to the temperature of the chamber and the temperature of the cooling bar 324 can influence the coated substrate 334. In an example, these and other process parameters can be under standard processing control.

The substrate 324 can be constructed from any naturally-occurring material or any man-made material, such as an FDA-approved polymer for the delivery of one or more herbal extracts, or any combination of naturally-occurring or man-made materials.

The substrate 324 can be a pharmaceutically acceptable material or combination of materials, including natural and/or synthetic materials, which can capture the one or more herbal extracts. In an example, pharmaceutically acceptable materials for the substrate can include, but are not limited to, cellulosic materials, synthetically altered cellulosic materials, synthetic polymers, natural polymers or any material approved for pharmaceutical use by the United States Food and Drug Administration (FDA). In an example, the materials can be porous, micro-porous, adsorptive or absorptive or include a combination of adsorptive and absorptive properties. In an example, the substrate can be stable and non-degrading at temperatures well above the volatilization temperatures of one or more herbal extracts. In an example, the substrate 324 can comprise an aluminum or aluminum alloy. If a substrate is to be designed as an electrically conductive synthetic or natural organic or inorganic polymer, it will include a feature providing the ability to conduct electricity. Such electrically conductive polymers are well-known.

Figure 4:
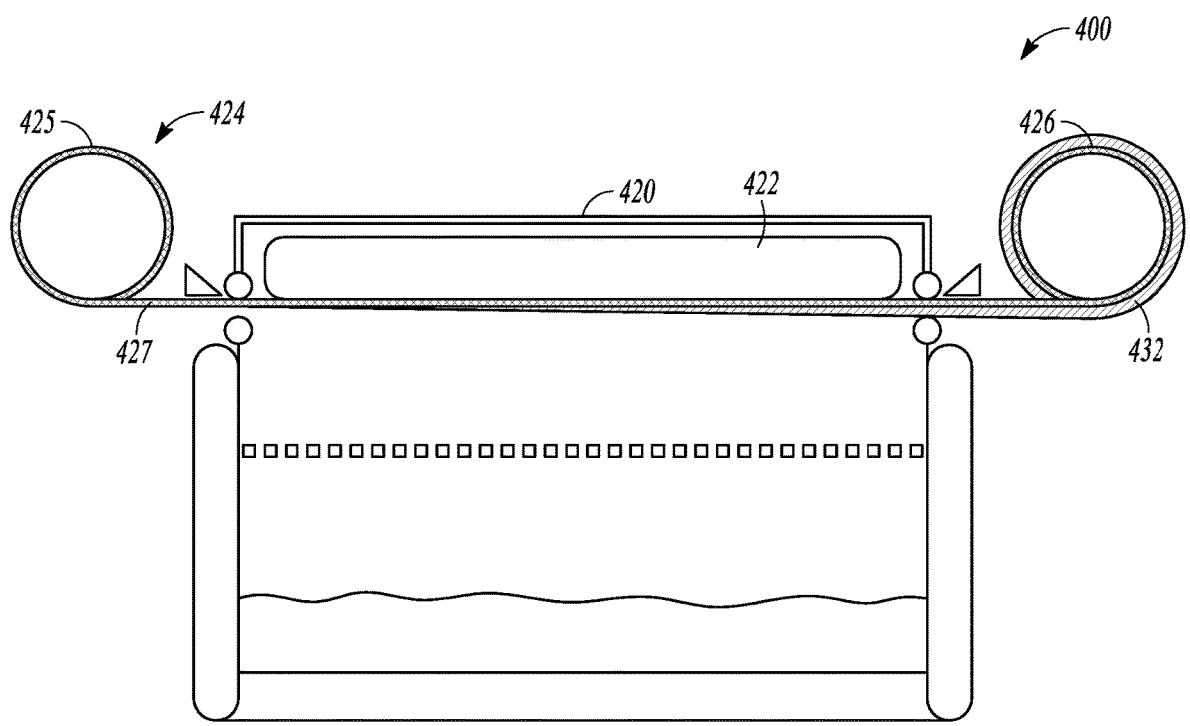
FIG. 4 is an example of a heating chamber having a continuous substrate coating process in accordance with the present invention.

FIG. 4 shows an example of a heating chamber 400 of the present disclosure for use in a continuous sheet substrate coating process. The heating chamber 400 can include many of the same elements as the heating chamber 300 of FIG. 3, but instead of being a batch process, it can include additional features to enable a continuous process. The container cover 420 can include a roller take-up mechanism 424. In an example, the roller take-up mechanism 424 can include a source spool mechanism 425, a receiving spool mechanism 426 and a flexible substrate 427 extending from the source spool mechanism 425 to the receiving spool mechanism 426 and located in close proximity to the cooling bar 422. In an example, the source spool mechanism 425 can include a spindle and bearings to support the source spool and a motor attached to the source spool for tensioning of the flexible substrate 427. In an example, the receiving spool mechanism 426 can include a spindle and bearings to support the receiving spool and a motor attached to the receiving spool to draw the flexible substrate 427 across the cooling bar 422. During the heating process, the receiving spool mechanism 426 can draw the flexible substrate 427 across the cooling bar 422 so that the herbal extract(s) condense on one side of the flexible substrate 427 to form a continuous coating 432 on the flexible substrate 427.

In an example, the roller take-up mechanism 424 can be controlled to perform continuous deposition processing of the flexible substrate 427. In an example, the roller take-up mechanism 424 can be controlled to perform multi-batch deposition processing of the flexible substrate 427. Other designs can be used as an alternative to or in addition to the mechanisms 424 and 426 for enabling a continuous process.

Figure 5C:
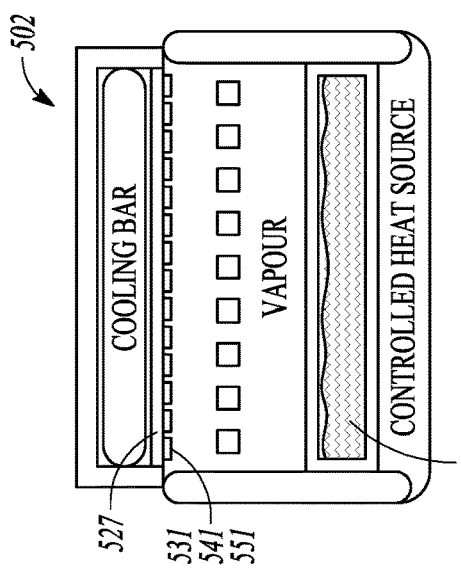
FIGS. 5A, 5B and 5C are examples of a series of heating chambers for producing a multi-layered substrate coating process in accordance with the present invention.
Figure 5B:
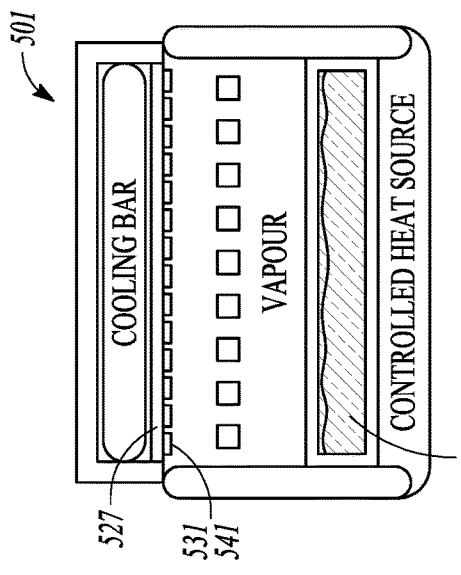
Figure 5A:
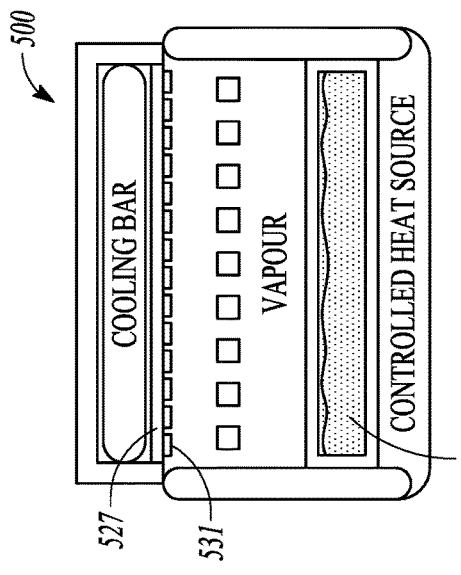
Figure 5D:
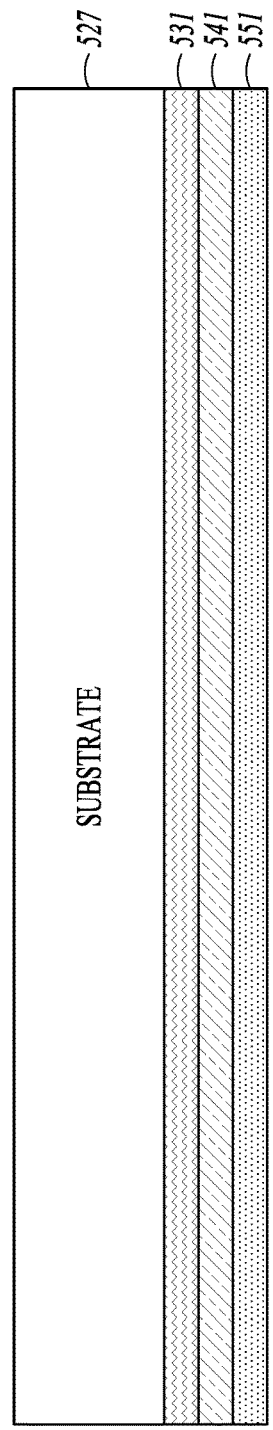
FIG. 5D is an example of a substrate with multiple layers of herbal extract(s)

FIGS. 5A, 5B and 5C show an exemplary series of heating chambers 500, 501 and 502 of the present disclosure for use in preparation of a substrate with a multiple layer coating of different herbal extracts. The heating chambers 500, 501 and 502 can be separate chambers arranged in a tandem order or can be a single chamber which is replenished with different herbaceous materials as feed stocks and which serve to convert chamber 500 to chamber 501 and hence into chamber 502. Heating chambers 500, 501 and 502 can include many of the same elements as the heating chambers 300 and 400 of FIGS. 3 and 4, respectively. When operated in tandem, the substrate 527 can be arranged on a continuous belt and roller as depicted in FIG. 4. The continuous belt and roller will extend through chambers 500, 501 and 502 with the outtake roller being positioned before chamber 500 and the uptake roller being positioned after chamber 502. Alternatively, a single chamber 500 can be employed and the herbaceous plant material changed to provide an operational configuration of chambers 501 and 502. In an example, flexible substrate 527 is coated in either a multi-batch or continuous deposition process with a first coat 531 of herbal extract from volatilization of herbaceous material 530 as shown in FIG. 5A. The chamber 500 is refilled with herbaceous material 540 so as to provide chamber 501. Alternatively, a second, separate chamber 501 is employed in this step as shown by FIG. 5B. A second coating of herbal extract 541 is applied to the substrate with coating 531 by volatilization and cooling as depicted in FIG. 5B. The result is a substrate with coatings 531 and 541. In a third step as shown in FIG. 5C the original chamber is replenished with herbaceous material 550 so as to provide chamber 502, or a third separate chamber 502 is used. Through volatilization and cooling, a third coating of herbal extract 551 is applied so as to produce a substrate with multiple coatings 531, 541 and 551. The substrate coated with three herbaceous extracts 531, 541 and 551 is shown in FIG. 5D.

Figure 6A:
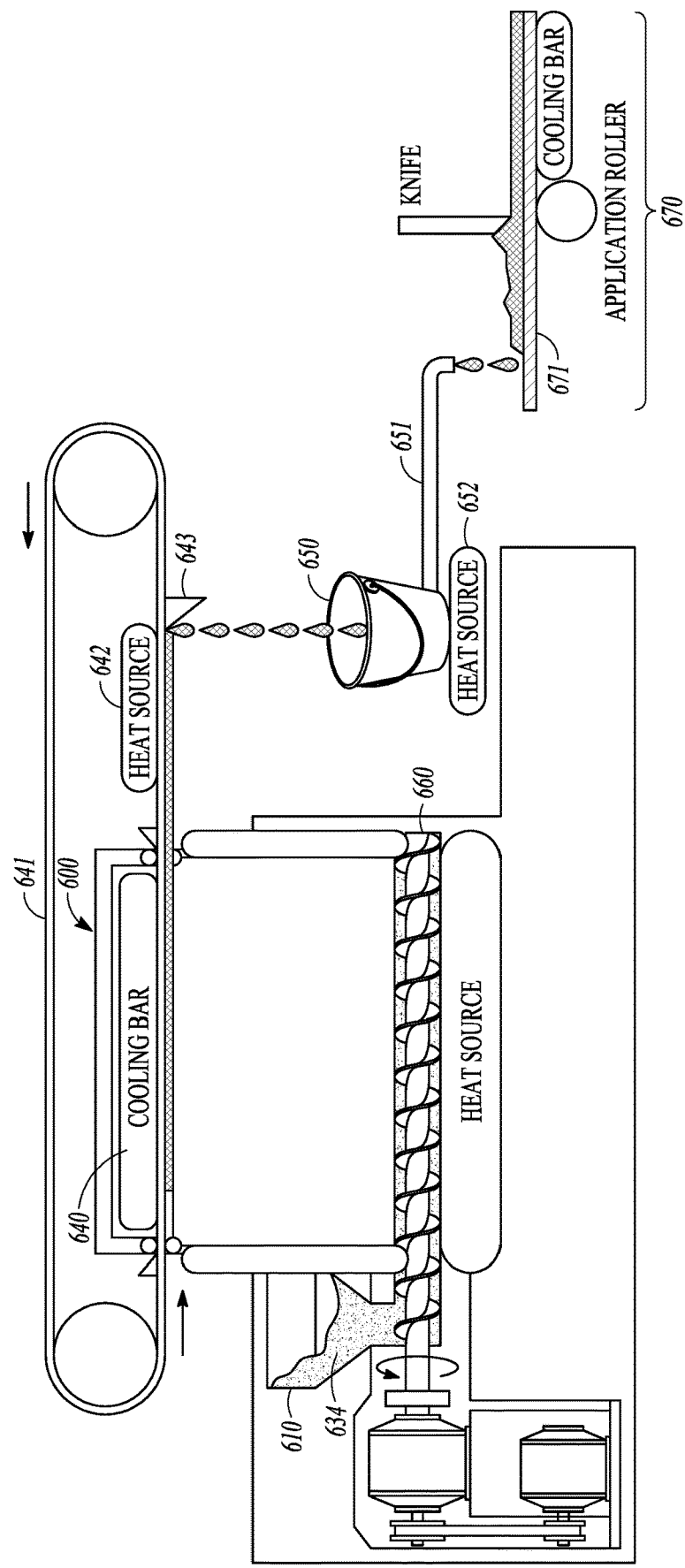
FIGS. 6A and 6B present an example of a heating chamber with transfer cooling belt, knife scraper and substrate deposit; and a storage and deposit system for processing one of more batches of herbaceous plant material in accordance with the present invention.
Figure 6B:
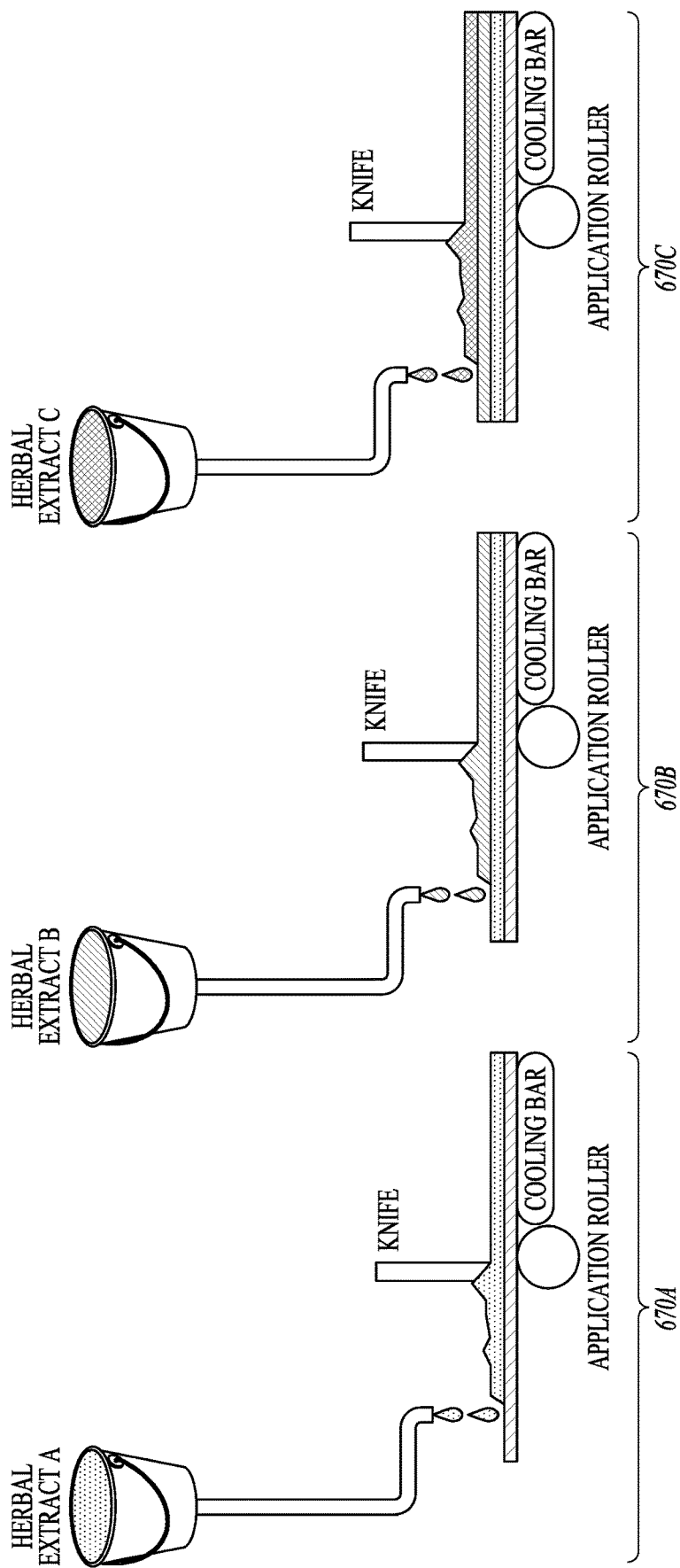

FIG. 6A shows an exemplary heating chamber 600 of the present disclosure for use in a continuous substrate coating process with a continuous source material feed system and a heated, remote storage and coating subsystem. The remote coating subsystem enables the use of a single heating chamber and a multiple number of storage and coating subsystems. The overall system enables large runs of herbaceous plant material and multiple coatings of batch substrates or continuous substrates. In an example, a screw conveyor 660 can move herbaceous plant material 634 into the feed hopper 610 for heating and volatilization. A screw conveyor 660 moves the herbaceous material 634 into the heating chamber 600. The screw conveyer can also be used to remove spent herbaceous plant material from chamber 600 and dispose it into a waste hopper (not shown). Multiple feed hoppers can be connected to a single delivery chute leading to the screw conveyor. Each hopper can contain a different herbaceous plant material and the release of each into the screw conveyer can be controlled by hopper outlet valves. In this fashion multiple herbaceous materials can be delivered to the single heating chamber so as to produce multiple herbal extracts. Each volatilized herbal extract is collected on a continuous belt 641 cooled by cooling bar 640. The belt with solidified herbal extract moves out of the heating chamber 600 and is subsequently warmed by heat source 642. Stripper 643 or a similar device causes the warmed herbal extract to pass into storage hopper 650. Storage hopper can be cooled or heated by heater/cooler 652 depending on whether the herbal extract is to be stored in hopper 650 or is to be transported through tube 651 to the remote coating subsystem 670. As shown in FIG. 6B, a remote series of coating subsystems 670*a*, 670*b* and 670*c* can be employed to provide substrates with multiple layers of herbal extracts or a series of substrates each with a single different herbal extract. The coating subsystem includes storage hoppers 650 with transport tubes 651 and heater coolers 652. The system can be arranged on a rotating platform synchronized with the continuous belt 641 and stripper 643 so that a series of herbal extracts can be collected, stored and sequentially applied to a substrate. To form a substrate with one or more layers of herbal extract, storage hopper 650 is heated and the liquid herbal extract caused to flow through tube 651 to the remote coating subsystem 670. The flowable herbal extract is deposited on substrate 671, is leveled by a leveling means such as a knife edge or a curtain of air or by gravity optionally in combination with movement of substrate 671 . . . . The leveled herbal extract layer is cooled by direct or indirect contact with a cooler or by cold air. A deposition of subsequent layers of different herbal extracts contained in additional storage hoppers 650 can be accomplished by the same process to produce a multi-coated substrate. The same process and coating subsystem can be employed to produce and store multiple herbal extracts and coat substrates with single coatings of different herbal extracts.

In an example, any of the heating chambers described above can be part of a mobile process such that the purification and coating processes can be done at or near the origin of the source material. In an example in which the source material is raw herbaceous plant material, the purification and coating processes can be contained or stored within a transportation device such that these steps can be performed at or near where the raw herbal extracts is grown.

In an example, a batch process similar to the heating chamber 300 of FIG. 3 can be used to sample source material and determine its composition, to determine, for example, levels of herbal extract(s) in the source material.

The heating chambers and processes described above in reference to FIGS. 3-6 are an example of a separation process for separating one or more components from the herbaceous plant composition. Other known processes may be used, such as, for example, a wet extraction process or a fractional distillation process. The particular process used for separating the desired components from the source material can depend, in part, on the composition and form (solid, liquid, etc.) of the source material, the nature of the herbal extract(s) desired, the volume of coated substrate to be produced, the time for production, technical expertise of the users, equipment availability and budget, and the cost of implementation.

Alternatively, a wet extraction method can be used to obtain the herbal extract(s). In an example, an herbaceous plant material containing an herbal extract, such as but not limited to an alkaloid such as sanguinarine (blood root) or *Digitalis* (digitalin and digitoxin from foxglove) can be comminuted to small particles and dried to remove water. Combining the dried herbaceous plant material with an appropriate solvent such as ethyl alcohol or chloroform or water extracts the herbal extract from the dried plant material and produces an herbal extract solution.

Optionally, treating the herbal extract solution with activated charcoal to decolorize, and optionally recrystallizing by addition of water followed by filtration, can be employed to produce purified herbal extract as an oil or solid.

Either the herbal extract solution can be concentrated by vacuum evaporation of a substantial amount of solvent to produce a concentrate or the purified herbal extract can be redissolved in a minimum amount solvent to produce a concentrate. The concentrate can be deposited as a layer of concentrate on a substrate.

The deposit can be accomplished by a batchwise technique involving placing the substrate in a catch pan with sides slightly higher than the side edges of the substrate. The catch pan and substrate can be sized to enable subsequent division of the coated substrate into dose calculated strips. The concentrate can be deposited onto the substrate in the catch pan that holds the concentrate at appropriate depth on top of the substrate. The concentrate can be flash evaporated by placing the catch pan with concentrate and substrate into a vacuum chamber and applying a vacuum with slightly elevated temperature. This technique will flash off the solvent while not volatilizing or subliming the herbal extract to any detectable degree.

The coated substrate can be cut or otherwise divided along predetermined lines to produce the unit dosage forms of substrate coated with herbal extract. As explained above, the coated substrate can be configured for use in a hot air delivery cartridge or configured with electric heating elements and flowing ambient air to entrain the herbal extract molecules in a micro-aerosol or solid particulate-gas mixture or volatize the molecules into a vapor for inhalation delivery to the lungs.

Administration of herbal extracts such as for example medicinal alkaloids such as sanguinarine (anti-bacterial) or *Digitalis* (cardiovascular) and other medicinal herbal extracts by inhalation into the lungs is an effective method for rapid and precise delivery of the medicinal to the organ or organs in need. This technique avoids transport of the medicinal through the gut-blood barrier and its passage through the hepatic route, both of which can cause degradation of the medicinal.

In an example, the purification and coating processes described above can include re-processing the coated substrate or transport by heating the coated substrate such that the herbal extract(s) on the coated substrate or transport belt are re-vaporized and then condensed onto a new substrate. This can be used to further purify the herbal extract(s) in the coated substrate and can be repeated until a desired purity of the at least one of herbal extract(s) is achieved.

An amount of the herbal extract(s) components in or on the coated substrates can be determined as part of the process for forming the coated substrate and the delivery cartridges described below. As described above, process control methods can be implemented to control, for example, a thickness of the coating on the substrate. Based on sampling of the source material, a composition of the coating on the substrate can also be determined. Other known techniques can be used to determine a composition of the coating on the substrate. As such, an amount of the herbal extract(s) component can be determined per unit area of the coated substrate. This can be used to determine an appropriate surface area of the delivery cartridge if there is a specified amount of the herbal extract(s) in the delivery cartridge. Similarly, if the surface area of the delivery cartridge is specified, the thickness of the coating on the substrate can be adjusted in order to meet a specified amount of the herbal extract(s) in the delivery cartridge. The methods described herein for forming the coated substrates and the delivery cartridges can be used to effectively and accurately determine a composition and amount of the herbal extract(s) which can be used for dosage control.

Coated substrates as described herein containing herbal extract(s) can be used to form a three-dimensional structure configured for use as a delivery product. In an example, a coated substrate can be used as a delivery cartridge in a delivery device. As used herein, a delivery cartridge can refer to a replaceable element in a delivery system that is slowly depleted of herbal extract(s) as a consequence of continued use or intervals of use. The delivery cartridge can be replaced for continued use of the delivery system. In an example, delivery cartridges can be designed to maximize surface area exposed to an air flow while minimizing package volume.

Coated substrates can take many structural forms. In an example, coated substrates can include, but are not limited to, cubes, cones, parallelenebulizerds, or other three-dimensional shapes. In an example, a coated substrate can be in the form of a sheet. As used herein, a sheet can be any three-dimensional structure defined by a first dimension, a second dimension and a third dimension where the first dimension is much smaller than the second and third dimensions. In an example, a sheet can be generally rectangular in shape with a first end and a second end opposite the first end.

FIG. 7A shows an example of a coated substrate 700 of the present disclosure which can be formed using the techniques described above or generally known in the art, examples of which are described above for extracting and purifying herbal extract(s) and coating the herbal extract(s) on a substrate. The substrate coated with herbal extract(s) 700 can include a substrate component 710, and herbal extract(s) 720 coated on the substrate component 710 and spacers 722 located on the substrate component 710 or the herbal extract(s) component 720. In an example, the spacers 722 can be located on the substrate component 710 before the substrate component 710 is coated. In an example, the spacers 722 can be located on the herbal extract(s) component 720 after the substrate component 710 is coated.

FIG. 7B shows an example where the substrate coated with herbal extract(s) 700 can be converted into a three-dimensional structure configured for use as a delivery cartridge 702. In an example, the substrate coated with herbal extract(s) 700 can be rolled into a spirally wound cylindrical shape to form the delivery cartridge 702. In an example, the plurality of spacers 722 can be used as a structural element to maintain channel(s) 724 between layers of the delivery cartridge 702 to allow for the passage of heated air. The delivery cartridge 702 can include any number of layers.

The delivery cartridge 702 can be used with a delivery device, an example of which is described below and shown in FIG. 17. In an example, the delivery device can include, but is not limited to a vaporizer, an e-cigarette device, a nebulizer or an aerosol device. Alternatively, the delivery cartridge 702 can be used by directly applying heated air to the delivery cartridge 702 to volatilize or entrain molecules of the herbal extract(s) from the delivery cartridge 702. In an example, heated air can be directly applied to the delivery cartridge 702 by any heating process or heating device that can include, but is not limited to, a vaporizer, an e-cigarette device, a nebulizer or an aerosol device In an example, heated air can be directed through the channel 724 to volatilize, and/or entrain as a solid-gas aerosol, molecules of the herbal extract(s) from the delivery cartridge 702.

FIG. 8 shows a flow chart of an exemplary process to construct a spirally wound cylindrical shape, similar to the cartridge 702 of FIG. 7B. In an example, step 810 can include providing a supply of herbaceous plant material; step 820 can include heating the herbaceous plant material to a first temperature to release a first vapor or wet extraction to produce a solution; step 830 can include condensing the first vapor or depositing and evaporating the solution onto a substrate to create a coated substrate; step 840 can include placing spacers on the coated substrate to allow for airflow through the cartridge; step 850 can include rolling the coated substrate to form a spirally-wound cylindrical shape configured for use as a delivery cartridge.

FIG. 9 shows an example of a coated substrate shaped in a saw-tooth, zig-zag, or accordion configuration. In an example, the saw-tooth coated substrate 900 includes a first coating 910 where the first coating 910 can be one of one or more herbal extracts. In an example, the saw-tooth coated substrate 900 includes a second coating 920 where the coating 920 can be another of the herbal extract(s)

FIG. 10 shows an example of a two-substrate assembly 1070 where a first saw-tooth coated substrate 1035 and a second saw-tooth coated substrate 1045 can be stacked for use as delivery cartridge. In an example, a plurality of spacers 1022 can be used as structural elements to maintain a plurality of channels 1024 between the first saw-tooth coated substrate 1035 and the second saw-tooth coated substrate 1045 to allow for the passage of heated air. In an example, the two-substrate assembly 1070 can be stacked so that the first coating 1010 of the first saw-tooth coated substrate 1035 can face the second coating 1020 of the second saw-tooth coated substrate 1045. In an example, a plurality of two substrate assembly 1070 can be stacked for use as a delivery cartridge.

Figure 11:
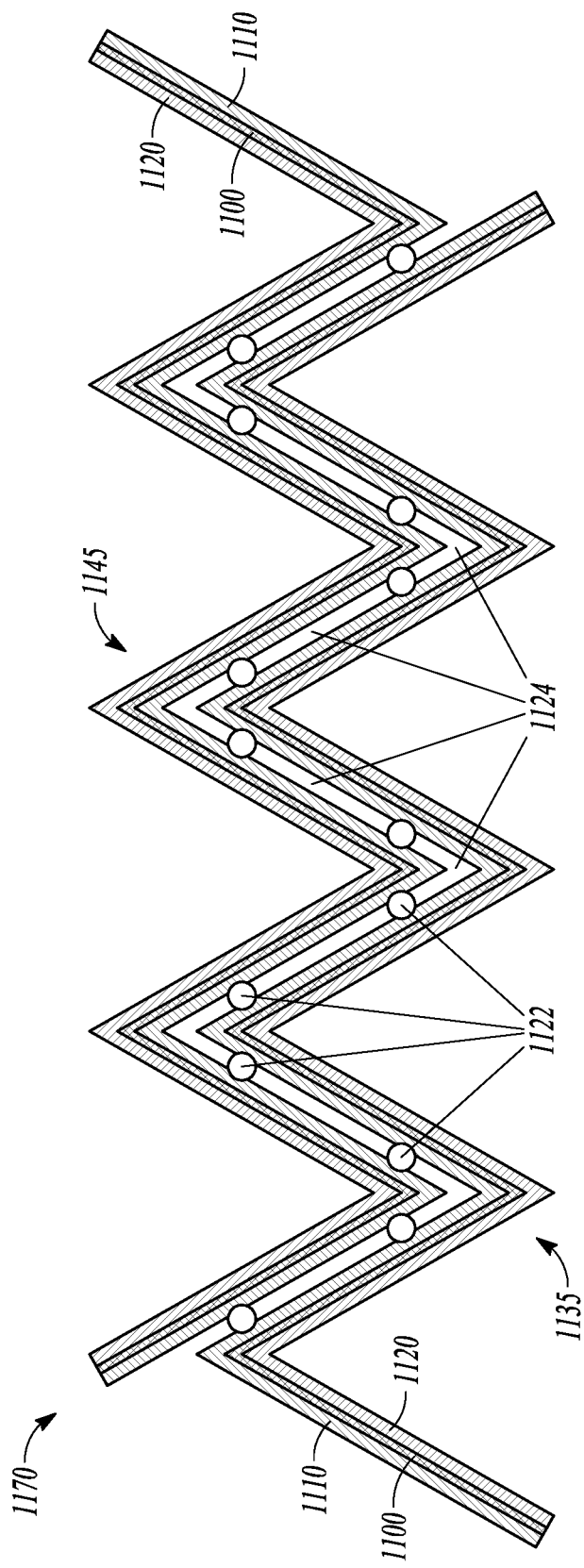
FIG. 11 is an example of a delivery cartridge having multiple segregated layers of coated substrates, in accordance with the present invention.

FIG. 11 shows an example of a two-substrate assembly 1170 where the first coating 1110 of a first saw-tooth coated substrate 1135 can face the first coating 1110 of a second saw-tooth coated substrate 1145. In an example, a plurality of two-substrate assembly 1170 can be stacked for use as a delivery cartridge.

Figure 10:
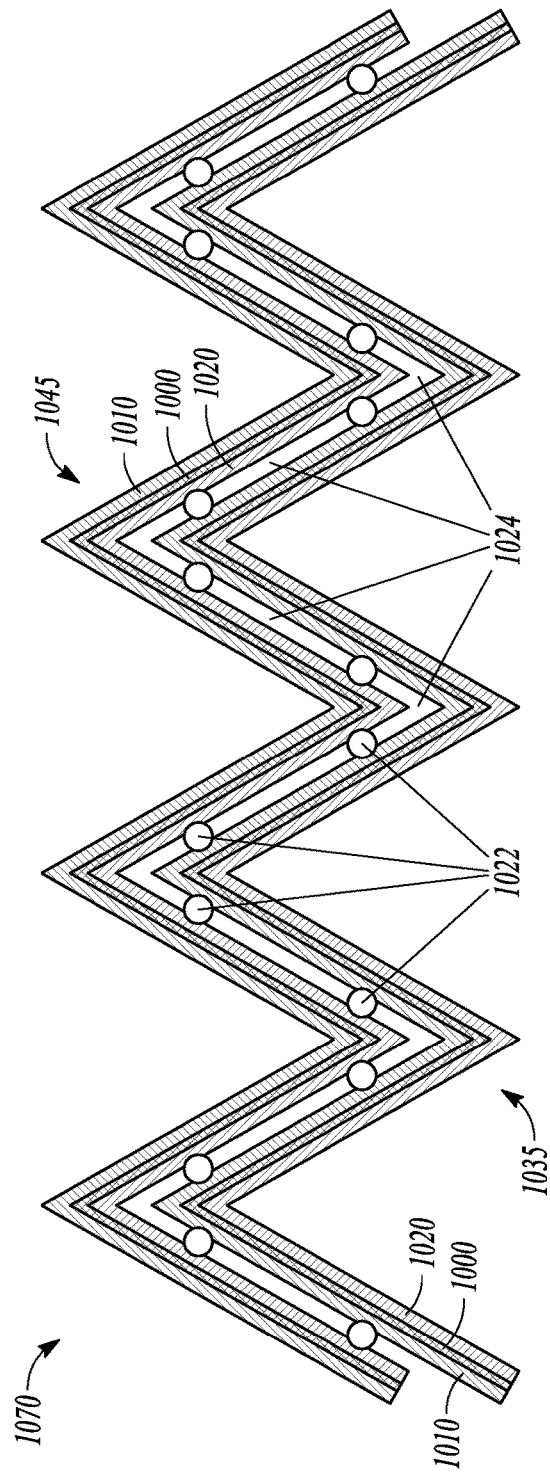
Figure 12:
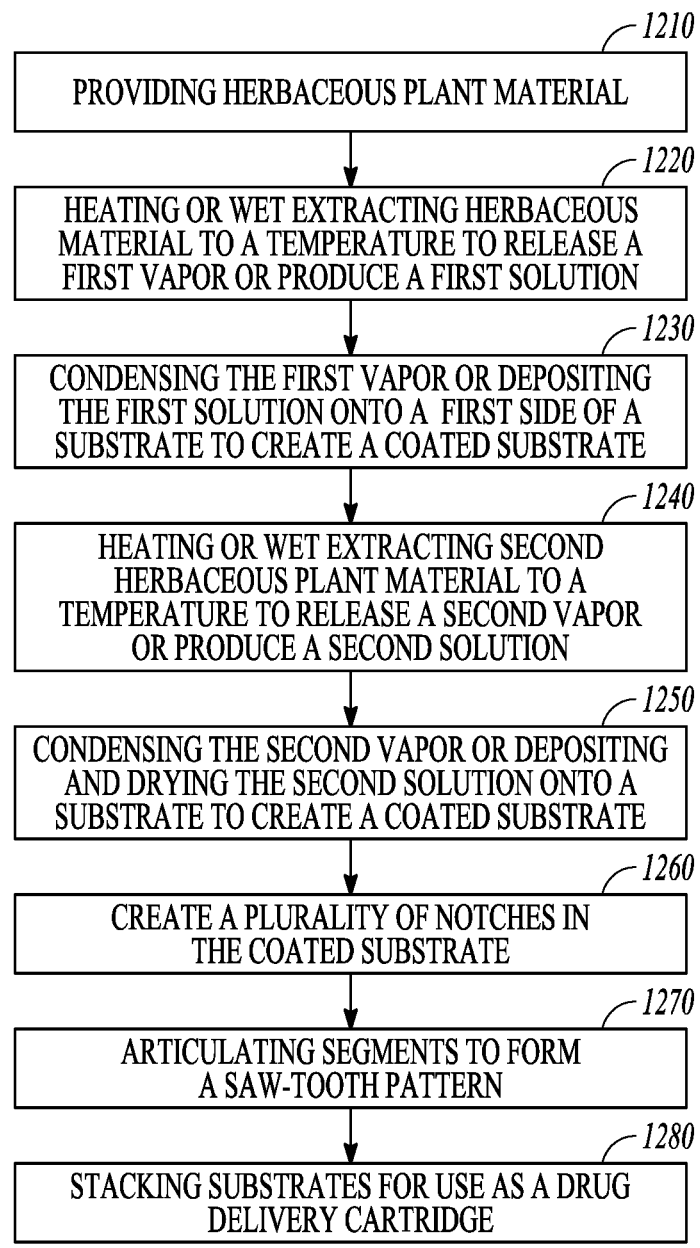
FIG. 12 is a block diagram of an example of a process to construct a delivery cartridge in accordance with the present invention.

FIG. 12 shows an example of a process to construct a saw-toothed delivery cartridge. In an example, step 1210 can include providing a supply of herbaceous plant material; step 1220 can include heating the herbaceous plant material to a first temperature to release a first vapor or wet extracting a first extract to form a solution; step 1230 can include condensing the first vapor or depositing and evaporating the solution onto a first side of a substrate; step 1240 can include heating a second herbaceous plant material to a second temperature to release a second vapor or performing a second wet extraction step; step 1250 can include condensing the second vapor or depositing and evaporating the second solution onto a second side of the substrate; step 1260 can include creating a plurality of notches in the coated substrate; step 1270 can include articulating the segments to form a saw-tooth pattern and step 1280 can include stacking the substrate for use as a delivery cartridge. The process of FIG. 12 can be modified to incorporate the multiple substrate assemblies shown in FIGS. 10 and 11.

Figure 13A:
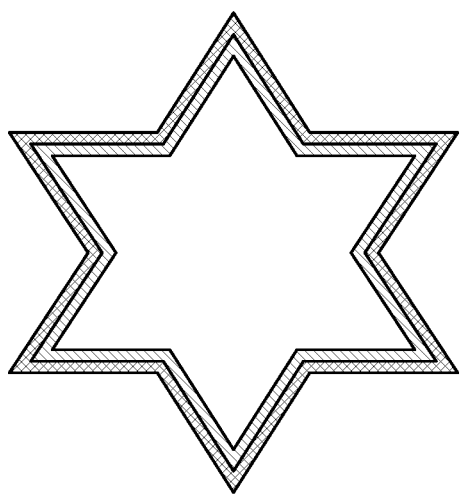
FIG. 13A is a top view of an example of a polygonal delivery cartridge in accordance with the present invention.
Figure 13B:
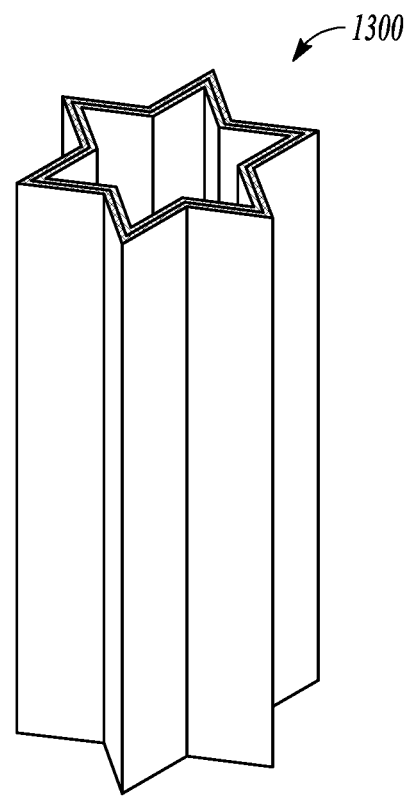
FIG. 13B is a perspective view of the polygonal delivery cartridge of FIG. 13A.

FIGS. 13A and 13B show top and side views, respectively, of an example of a polygonal delivery cartridge 1300. In an example, the cross-sectional shape of the polygonal delivery cartridge can include, but is not limited to, a three-side cross-section, a four-sided cross-section or an "n"-sided cross-section where "n" can be any number equal to or greater than 3.

Figure 13C:
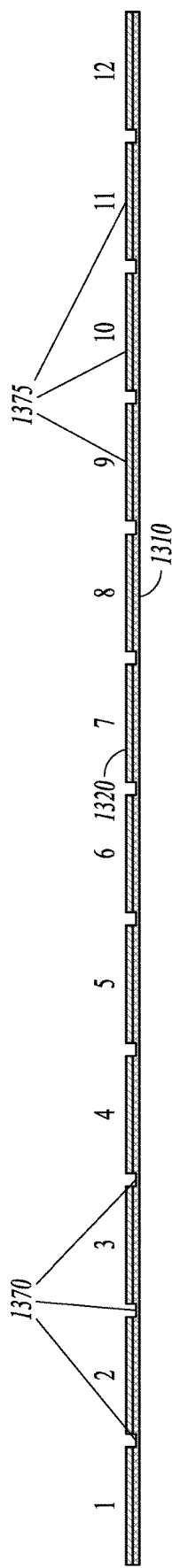
FIG. 13C is a side view of the coated substrate of the delivery cartridge of FIGS. 13A and 13B prior to forming the polygonal shape.
Figure 13D:
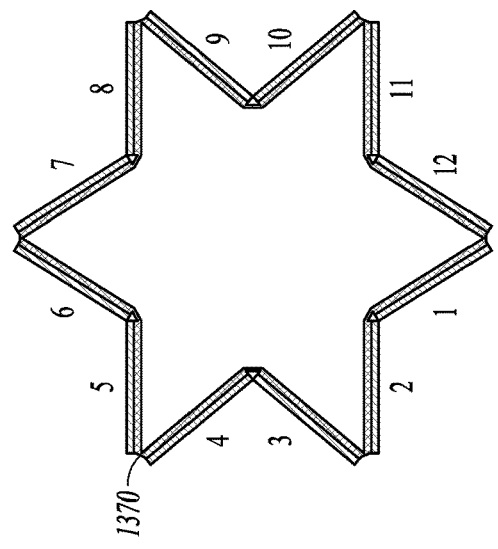
FIG. 13D is an end view of the, coated substrate of FIG. 13C formed into a polygonal shape.

FIG. 13C shows notches 1370 formed in the substrate 1310 and the coating 1320 that can allow a segment 1375 to articulate with respect to an adjacent segment 1375. As used herein, a segment 1375 is the portion of the substrate 1310 and coating 1320 located between two notches 1370.

Figure 14:
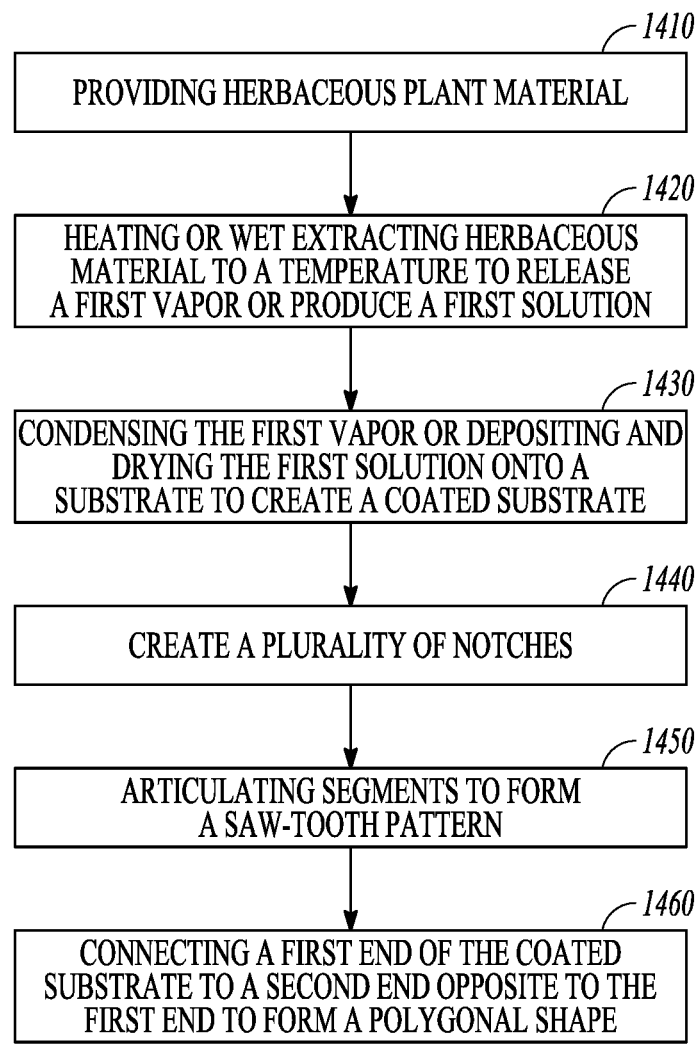
FIG. 14 is a block diagram of an example of a process to construct a polygonal delivery cartridge in accordance with the present invention.

FIG. 14 shows an example of a process to construct a closed polygonal shaped delivery cartridge similar to the star-shaped cartridge 1300 of FIG. 13. In an example, step 1410 can include providing a supply of herbaceous plant material; step 1420 can include heating the herbaceous plant material to a first temperature to release a first vapor or wet extraction to produce a first solution; step 1430 can include condensing the first vapor or depositing and evaporating the first solution onto a substrate to create a coated substrate; step 1440 can include creating a plurality of notches and step 1450 can include articulating the segments to form a saw-tooth pattern; and step 1460 can include connecting the first end to the second end to form a polygonal shape. In an example, step 1460 can include manipulating the segments to align the segments in a desired orientation relative to one another.

Figure 7A:
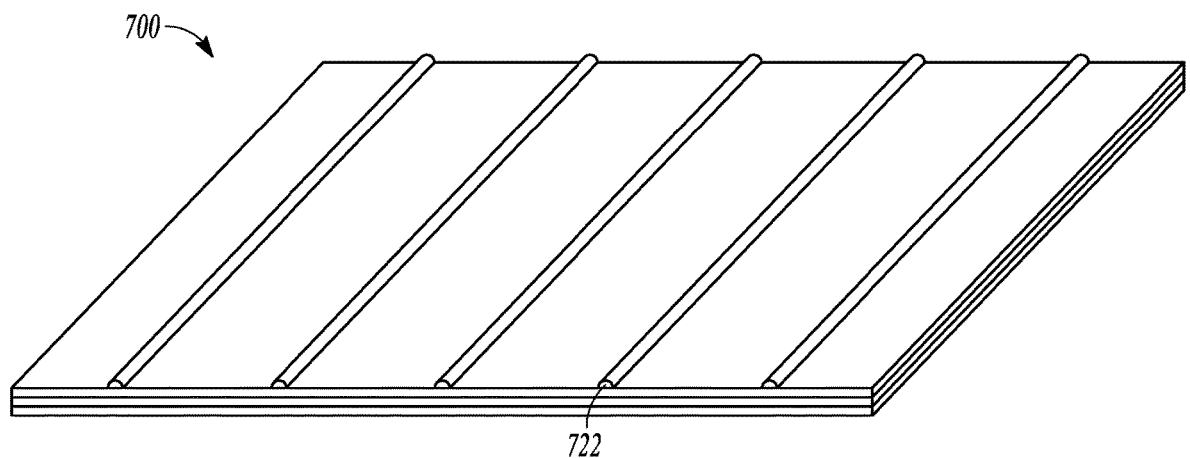
FIG. 7A is an example of a penultimate form of a delivery cartridge formed of a substrate with a multilayer coating of herbal extracts and separation spacers in accordance with the present invention.
Figure 7B:
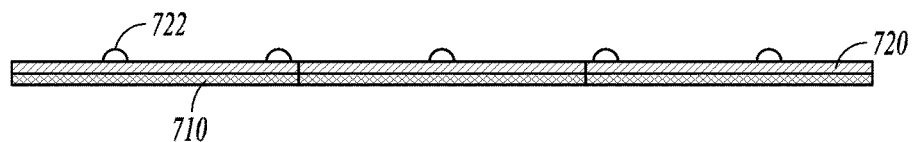
FIG. 7B is an example of a penultimate form of a delivery cartridge with a segregated multi segment substrate in accordance with the present invention.
Figure 7C:
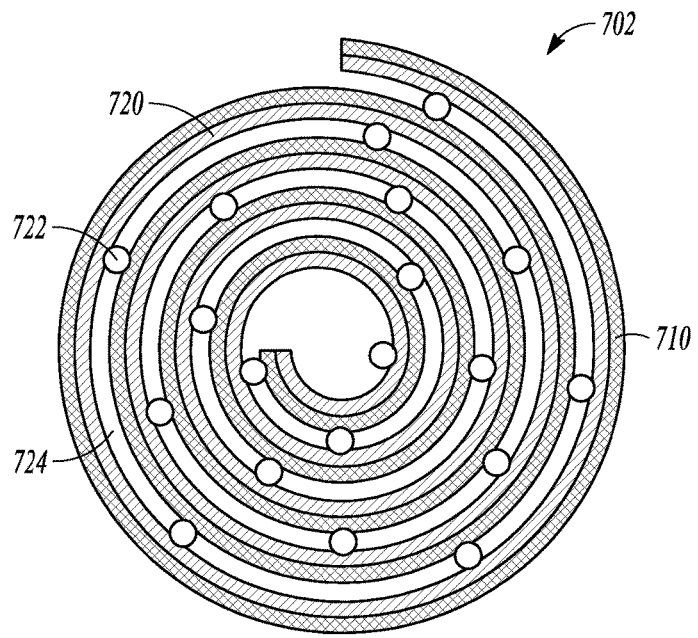
FIG. 7C is an example of an end view of the delivery cartridge formed
Figure 8:
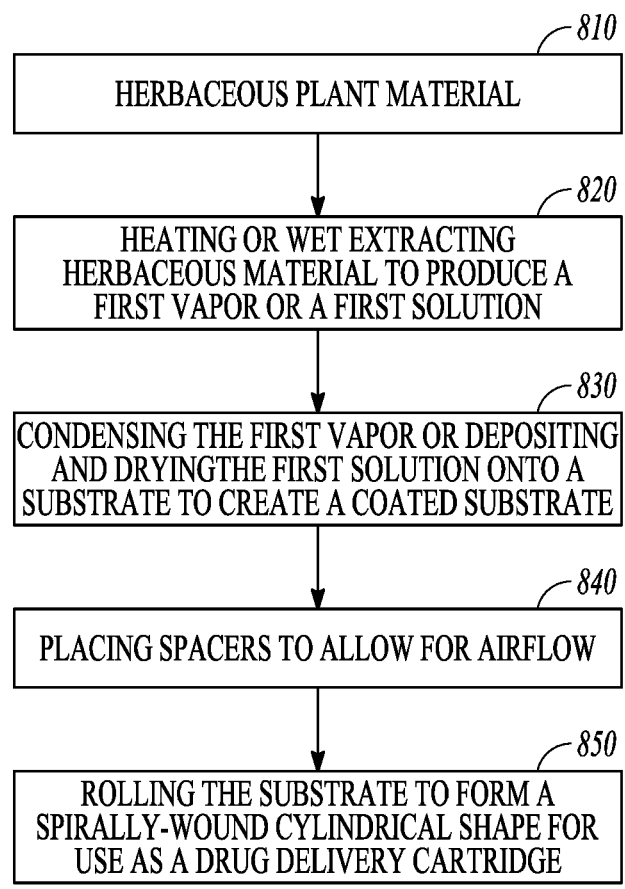
Figure 9:
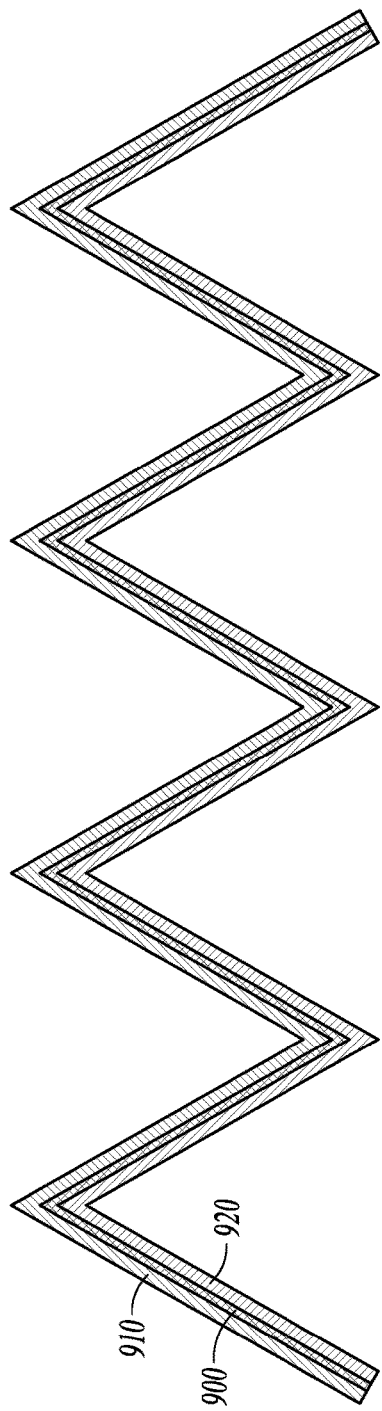

Other shapes can be used for a delivery cartridge. Any of the examples described and shown in FIGS. 7, 9, 10, 11 and 13A-13C can include additional layers of substrate and each layer of substrate can include one or more coating layers. As stated above in reference to FIG. 7B, the delivery cartridges described herein can be used alone or in combination with a delivery device. Each delivery cartridge can be designed such that heated air can be passed through the cartridge and one or more herbal extract(s) can be volatilized or entrained and inhaled by a user.

Dimensions of any of the delivery cartridges described herein can depend, in part, on whether a delivery device is intended to be used with the cartridge and a particular design of the delivery device. These dimensions can include a length, width and overall shape of the delivery cartridge and can depend on the length and width of the coated substrate used to form the delivery cartridge. The dimensions of the delivery cartridge can also depend, in part, on an amount of the herbal extract(s) in the delivery cartridge and an intended dosage of the herbal extract(s).

Figure 15:
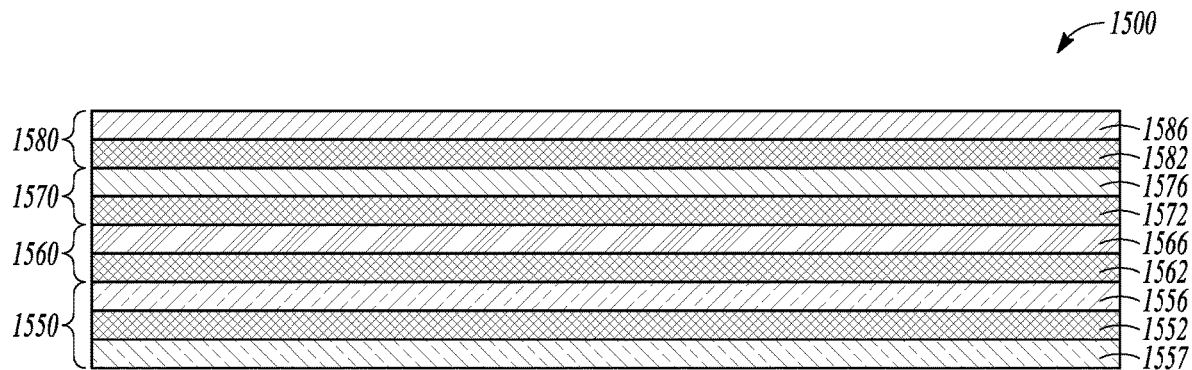
FIG. 15 is an exploded cross-section view of an example of a multi-layer substrate in accordance with the present invention.

FIG. 15 shows an exploded view of an example of an assembly 1500 comprising multiple layers of coated substrates. In an example, an herbal extract layer 1550 can include a substrate 1552 with a first surface and a second surface where a first herbal extract coating 1556 can be applied to the first surface and a second herbal extract coating 1557 can be applied to the second surface. In an example, a taste layer 1560 can include a substrate 1562 having a taste coating 1566 applied to the substrate 1562 to enhance or mask the user sensation as some but not all herbal extracts have bitter and/or unpleasing tastes and/or odors. In an example, the taste coating 1566 can include a flavoring that can include, but is not limited to, fresh mint and/or a volatile sweetening agent such as sorbitol. In an example, an adjuvant layer 1570 can include a substrate 1572 having an adjuvant coating 1576 applied to the substrate 1572 where the adjuvant coating 1576 can include at least a second compound that can augment the therapeutic effect of the herbal extract. In an example, the second compound can include, for example, a volatizable adjuvant for medicinal agents, the adjuvant being, for example, paraffin oil or squalene. In an example, an amelioration layer 1580 can include a substrate 1582 having an amelioration coating 1586 applied to the substrate 1582 where the amelioration coating 1586 can include at least a third compound that can minimize any undesirable side effects of herbal extracts, if applicable. In an example, the active herbal extracts layer 1550, the taste layer 1560, the adjuvant layer 1570 and the amelioration layer 1580 can be assembled together or in any permutation. In a further example incorporating any or all of the foregoing features of the coatings applied to the substrate, an herbal extract applied as first or second coating 1556 or 1557 respectively to the first or second surfaces of substrate 1552 may be one or more *Cannabis* extracts such as THC and/or CBD or may be one of the herbal extracts delineated in the foregoing list of extracts. Preferably, the coatings may be a combination of *Cannabis* extracts with one of the other herbal extracts. More preferably, the coatings may be a combination of *Cannabis* extracts and an adjuvant or flavoring. In an example, the assembly 1500 can be converted into a three-dimensional structure for use as a delivery cartridge as described above. In other examples, an assembly can include any number and combination of layers depending on desired properties of the assembly. In an example, spacers similar to the spacers 722 shown in FIGS. 7A and 7B can be placed between each layer prior to forming the three-dimensional structure to allow for the passage of air between the layers.

Figure 16:
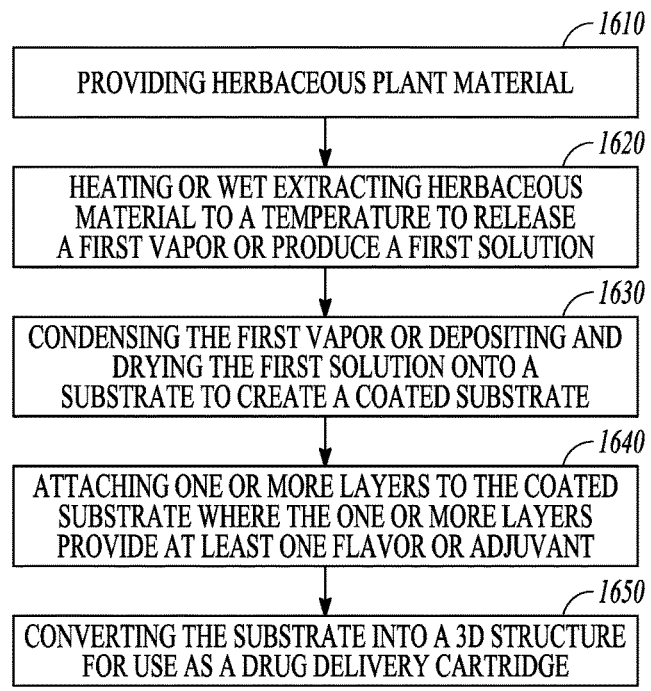
FIG. 16 is a block diagram of an example of a process used to make a delivery cartridge having two or more layers, in accordance with the present invention.

FIG. 16 shows an example of a process used to make a delivery cartridge where the coated substrate includes two or more layers where at least one provides flavor or adjuvant. In an example, step 1610 can include providing a supply of herbaceous plant material; step 1620 can include heating or wet extracting the herbaceous plant material to release a first vapor or produce a first solution; step 1630 can include condensing the first vapor or depositing and drying the first solution onto a substrate to create a coated substrate; step 1640 can include attaching one or more layers to the coated substrate where the one or more layers provide at least one of flavor or adjuvant of the at least one of one or more herbal extracts, and step 1650 can include converting the substrate into a three-dimensional structure for use as a delivery cartridge. In an example, an additional step can be performed between steps 1630 and 1640 which can include heating or wet extracting the second, different herbaceous plant material to release a second vapor or to produce a second solution and subsequently condensing the second vapor or depositing and drying the second solution onto the substrate, thus creating a second coating on the coated substrate, as described above.

As described above in reference to the coated substrates, a composition and amount of the herbal extract(s) in the delivery cartridge can be determined and controlled, which can be used for dosage control of the herbal extract(s). In an example, the delivery cartridges can contain a predetermined quantity of herbal extract(s) and can be designed as single dosage or multi-dosage cartridges. Using the control parameters described above, a quantity of herbal extract(s) in the delivery cartridge can vary depending, for example, on the intended use of the herbal extracts.

A delivery cartridge can cooperate with a delivery device that supplies a volatilizing heat source to deliver the herbal extract(s) in the delivery cartridge to a user. In an example, the delivery device can include, but is not limited to, an e-cigarette, a bong, a water nebulizer and a vaporizer.

Figure 17:
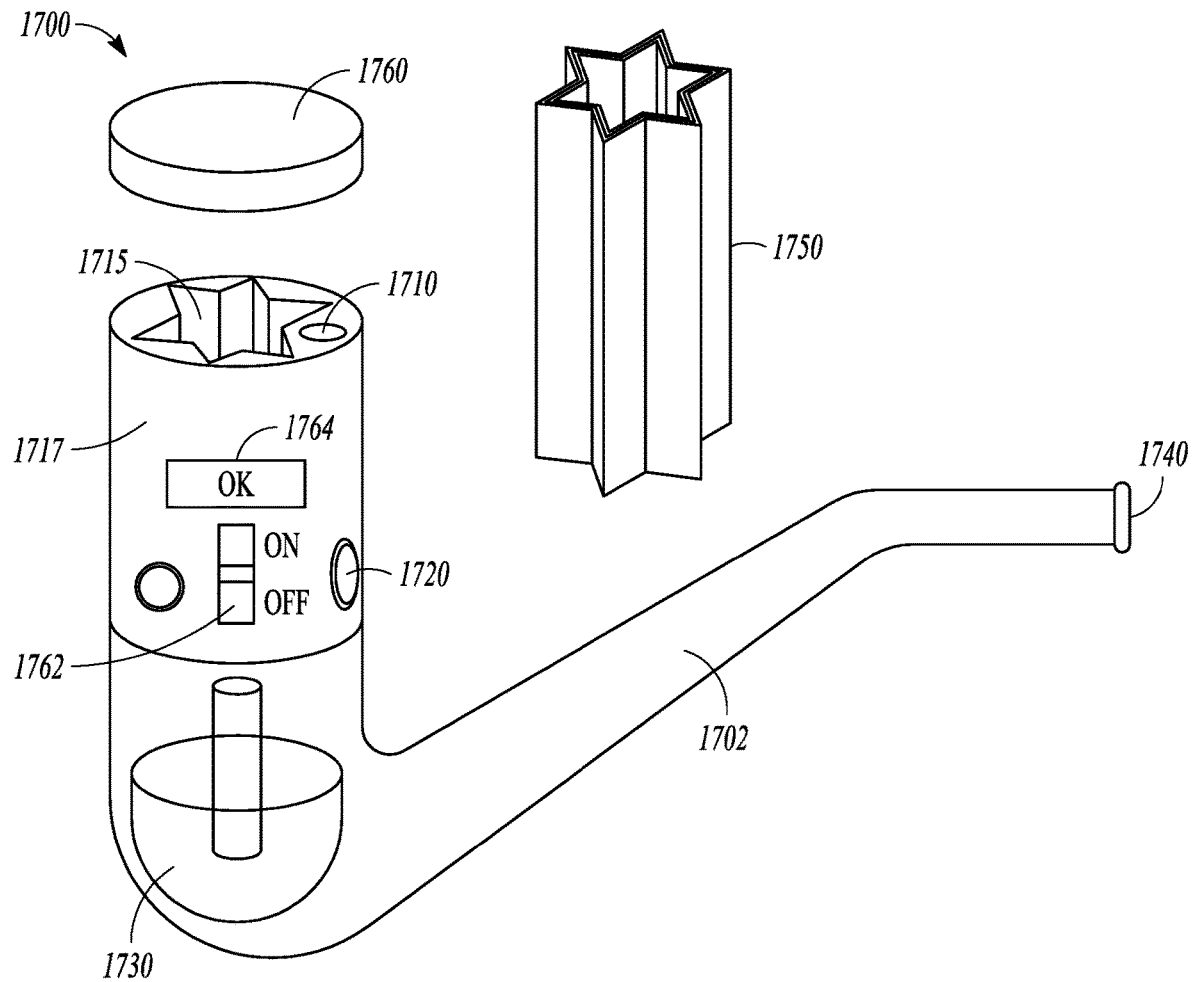
FIG. 17 is a perspective view of an example of a delivery cartridge in combination with a delivery device, in accordance with the present invention.

FIG. 17 shows a delivery cartridge 1750 in combination with an example of a delivery device, an electronic nebulizer 1700. In an example, the electronic nebulizer 1700 and the delivery cartridge 1750 form a delivery system. The electronic nebulizer 1700 can include a heating element 1710 with an opening 1715 sized and shaped to receive the delivery cartridge 1750, a power unit 1717, an air intake 1720, a moisturizing and cooling chamber 1730, a mouthpiece 1740, a cover 1760, a power switch 1762 and a digital readout 1764.

The heating element 1710 can heat the delivery cartridge 1750 to a specified temperature. In an example, the heating element 1710 can pre-heat the delivery cartridge 1750 to a temperature less than a volatizing or entraining temperature of the herbal extracts so that the delivery cartridge 1750 can readily volatize or entrain the molecules of the herbal extract on user demand. In an example, the heating element 1710 can heat the delivery cartridge 1750 to a temperature greater than or equal to a volatizing or entraining temperature of the herbal extract(s) to volatize or entrain the herbal extract(s) for delivery of the volatized herbal extracts on user demand.

The air intake 1720 provides makeup air to the electronic nebulizer 1700. In an example, the air intake 1720 can be a hole located in the electronic nebulizer 1700 in communication with the opening 1715, the moisturizing and cooling chamber 1730 and the mouthpiece 1740. In an example, the air intake 1720 can allow makeup air to flow into the electronic nebulizer 1700 when a user induces a negative pressure (or suction) action at the mouthpiece 1740.

The cover 1760 can prevent users from contacting the heating element 1710 during operation of the electronic nebulizer 1700. In an example, the cover 1760 removably attaches to the electronic nebulizer 1700 to prevent loss of the delivery cartridge 1750 during use.

The power switch 1762 controls the flow of electrical power from a power unit 1717 to the heating element 1710.

In an example, electrical power can flow from the power unit 1717 to the heating element 1710 when the power switch 1762 is in an 'on' position. In an example, electrical power can be prevented from flowing from the power unit 1717 to the heating element 1710 when the power switch 1762 is in an 'off' position.

The delivery cartridge 1750 can be used with the electronic nebulizer 1700 to deliver a predetermined and accurate quantity of volatized or entrained herbal extract(s) to a user. As described above, the amount of the herbal extract(s) in the cartridge 1750 can be controlled and thus known. The cartridge 1750 can be a single dose cartridge or intended for use over multiple doses. In an example, a user can remove the cover 1760 from the electronic nebulizer 1700 and insert a delivery cartridge 1750 into the opening 1715. In an example, the user can removably attach the cover 1760 to the electronic nebulizer 1700 before adjusting the power switch 1862 to the 'on' position in order to preheat the delivery cartridge 1750. In an example, the user can monitor the digital display 1764 for a visual cue that indicates that the electronic nebulizer 1700 is ready for use.

A delivery device can be configured to control the dosage of the herbal extract(s) to the user such that a multi-dose cartridge can be used with the delivery device, while still maintaining dosage control. For example, a delivery device similar to the electronic nebulizer 1700 can be configured to deliver a predetermined amount of herbal extract(s) per inhalation.

The delivery device can control how much air passes through the delivery cartridge and how much air is delivered to the user. In an example, a valve device inserted into the air flow of the delivery device can be used to control the volume of air available to the user. For example, the valve device can be located in the mouthpiece of a delivery device to throttle the volume of air flowing through the mouthpiece. In an example, the valve device can include, but is not limited to, a flapper valve, a ball valve, a gate valve, a butterfly valve, a duckbill valve or an adjustable orifice.

In an example, the valve device can include a timer device that can cause the valve device to open or close after an interval of time to regulate air flow through the delivery device. For example, the valve device can include an openloop timer device utilizing mechanisms such as a spring or a mechanical linkage to open or close the valve device. In another example, the valve device can include a closed-loop timer device using an actuator, an electrical control circuit and one or more feedback sensors to implement a control algorithm to open and close the valve.

The delivery device can also control other parameters that impact the amount herbal extracts(s) delivered to the user, including, for example, a temperature that the cartridge is heated to and the rate of airflow. Because the delivery cartridge only contains the desired components, have already been separated from the undesirable components in the source material, sufficient heat can be applied to the delivery cartridge to quickly vaporize or entrain the herbal extract(s) without worrying about the undesirable components also being vaporized.

The delivery cartridge can be configured to control the amount or dose of herbal extract(s) delivered. In an example, the delivery cartridge can be coated with a micro porous film to control the flow of herbal extract(s) vapor or entrained microparticles from the delivery cartridge. For example, the diameter of the pores in the micro porous film applied to the coated substrate can be sized to control the dose of herbal extract(s) delivered. In an example, the coated substrate used to form a delivery cartridge can be coated with a micro porous film to control the flow of herbal extract(s) vapor or entrained herbal microparticles from the coated substrate and thereafter formed into a delivery cartridge.

In an example, the delivery cartridge can be constructed from a coated substrate comprising a conductive material. In an example, the conductive material can include, but is not limited to, aluminum. In an example, an electrical power circuit can be connected to the conductive material to resistively heat the conductive material to a temperature sufficient to volatilize or entrain the herbal extract(s) on the coated substrate. In an example, the electrical power circuit can include an electrical control circuit and one or more feedback sensors to resistively heat the conductive material to a sufficient temperature and thereafter accurately maintain the temperature over a period of time.

In an example, the delivery cartridges described herein can be used with a vaporizer or entrainer. The vaporizer or entrainer can be configured to include a chamber or receptacle into which the delivery cartridge can be placed. The delivery cartridge can be configured as a single dose or multi-dose cartridge. Given the control parameters that can be used in the process of making the delivery cartridge, the delivery cartridge can include a known quantity of the herbal extract(s). As similarly stated above, a heating temperature of the vaporizer or entrainer is not a significant concern because the delivery cartridge only includes the desired herbal extract(s) and the substrate used in forming delivery cartridge can be inert at these operating temperatures.

Figure 18:
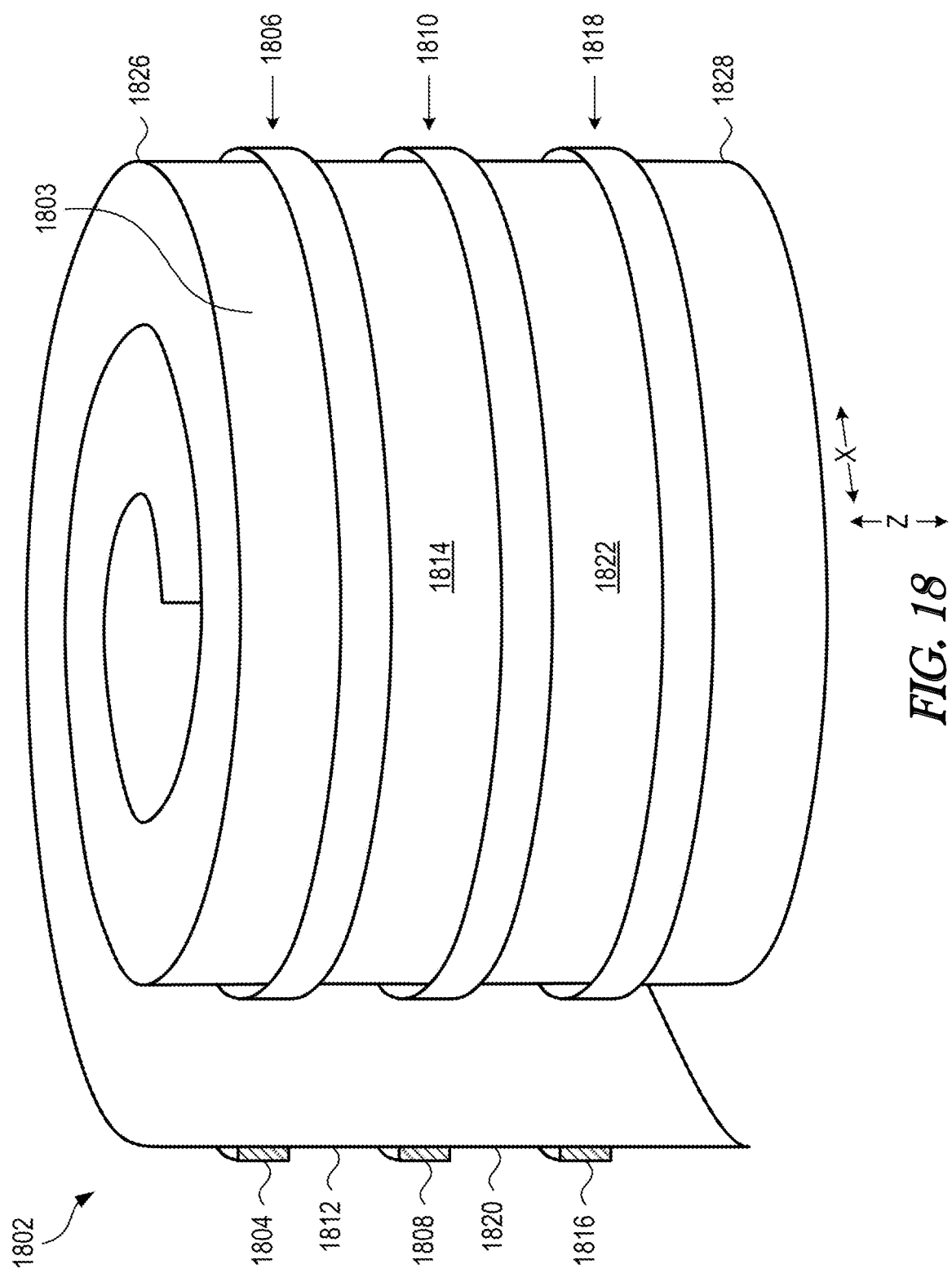
FIG. 18 shows an example of a cylindrically rolled sheet, which can be suitable for use with a delivery system.

FIG. 18 shows an example of a cylindrically rolled sheet 1802, which can be suitable for use as a delivery cartridge with a delivery system. The term cylindrical, as used herein, is intended to mean that the cross-sectional shape of the rolled sheet is the same at each longitudinal location along the rolled sheet 1802. For instance, the cross-section itself can be a circle, a spiral, a curve that lacks sharp corners, a curve that includes at least one sharp corner, a combination of curved and straight portions, a polygon, a square, a star shape, and other suitable shapes. In some examples, the cylindrically rolled sheet can form a tunnel structure that can support air flow there through. The rolled sheet 1802 of FIG. 18 is but one example of a cylindrical structure for use as a delivery cartridge. As described below, a cylindrical closed-end structure, such as a tube or a star can alternatively be used.

As described above and shown in the figures, any suitable shape can be used for the delivery cartridge, and the shape and design is not limited to the examples described and shown herein. As described above, the delivery cartridge can be cylindrical such that the cross-sectional shape is the same at each longitudinal location. In other examples, non-cylindrical designs can be used in which the cross-sectional shape varies longitudinally. In other examples, the delivery cartridge can be further converted to have a shape configured for use with different delivery systems. Further converting can include, for example, shaping a cylindrical structure into a J or an S for use in a nebulizer.

Referring back to FIG. 18, the rolled sheet 1802 includes a substrate 1803, which can be formed from an electrically conductive material, such as aluminum, copper, or another suitable metal or metal alloy. The rolled sheet 1802 is shaped to allow a gaseous flow in its interior, along the longitudinal direction (Z), from a first longitudinal end 1826 to a second longitudinal end 1828 opposite the first longitudinal end 1826. As further described below, all or a portion of the substrate 1803 can be covered with a coating of herbal extract(s). As described above, in some examples, the herbal extract(s) component can include one or more herbal extracts on one or both sides of the substrate 1803.

The rolled sheet 1802 can include a first electrode 1804 extending laterally (X) across the substrate 1803 at a first longitudinal location 1806. In some examples, the first electrode 1804 can be formed integral to the substrate 1803 to form the rolled sheet 1802, for example, by extruding the electrode 1804 onto the substrate 1803. In those examples, the first electrode 1804 can be thicker relative to the substrate 1803. In some examples, the first electrode 1804 can be originally separate from the substrate 1803 and attached to the substrate 1803, so that the first electrode 1804 is electrically coupled to the substrate 1803 to form the rolled sheet 1802. This is described further below. In some examples, the first electrode 1804 can extend outward from the rolled sheet 1802, toward an exterior of the rolled sheet 1802. In other examples, the first electrode 1804 can extend inward from the rolled sheet 1802, toward an interior of the rolled sheet 1802. In still other examples, the first electrode 104 can extend both outward and inward from the rolled sheet 1802.

The first electrode 1804 can be formed from an electrically conductive material and can be formed from the same or a different material than the substrate 1803. Example materials include, but are not limited to, aluminum, copper, or another suitable metal or metal alloy. The particular material selected can depend in part on whether the first electrode 1804 is integral to or separate from the substrate 1803. The first electrode 1804 can act a contact portion for use within a housing of an herbal extract(s) delivery system having corresponding electrodes, as described further below.

In an example in which the first electrode 1804 is separate from the substrate 1803, the first electrode 1804 can be made of steel and welded to the substrate 1803 to form the rolled sheet 1802. In such an example, the steel material can optionally be formed or provided as a coiled spring which can be straightened out to weld the material to the substrate and then the material can coil back up as the substrate 1803 is rolled to form the rolled sheet 1802. Other materials and other assembly methods can be used to form the rolled sheet 1802 out of the substrate 1803 and first electrode 1804.

The rolled sheet 1802 can also include a second electrode 1808 extending laterally (X) across the rolled sheet 1802 at a second longitudinal location 1810. The second electrode 1808 can be similar to the first electrode 1804 and have the properties described above. The first and second electrodes 1804, 1808 can each have an electrical resistance small enough to conduct current laterally (X direction) along the rolled sheet 1802 without heating the rolled sheet 1802. The second electrode 1808 can also be formed as a thick portion of the rolled sheet 1802, or formed separately from the rolled sheet 1802 and attached to the rolled sheet 1802, as described above with reference to the first electrode 1804.

The rolled sheet 1802 can include a first substrate portion 1812 extending longitudinally (Z direction) between the first and second electrodes 1804, 1808. The first substrate portion 1812 can have an electrical resistance high enough to conduct current longitudinally (Z) between the first and second electrodes 1804, 1808 and resistively heat the first substrate portion 1812 in response to the current conducted there through.

A first dose 1814 of an herbal extract(s) can be disposed on the first substrate portion 1812 of the substrate 1803 and configured to volatilize or entrain into vapor or aerosol in response to the resistive heating of the first substrate portion 1812. In some examples, the first dose 1814 of the herbal extract(s) can be uniformly coated on the first substrate portion 1812. In other examples, the first dose 1814 of the herbal extract(s) can include discrete pieces of multiple herbal extract(s) adhered to the first substrate portion 1812. In some examples, the herbal extract(s) can be coated on an exterior side of the substrate 1803 in the area identified as the first portion 1812. In some examples, the herbal extract(s) can be coated on an interior side of the substrate 1803 in the area identified as the first portion 1812. In some examples, the herbal extract(s) can be coated on both the interior and exterior sides of the substrate 1803. In some examples, different herbal extract(s) or combinations of herbal extract(s) can be coated on the interior and exterior sides of the substrate 1803.

In some examples, the rolled sheet 1802 can further include a third electrode 1816 extending laterally (X) across the rolled sheet 1802 at a third longitudinal location 1818, so that the second electrode 1808 is positioned longitudinally between the first and third electrodes 1804, 1816. The third electrode 1816 can have an electrical resistance small enough to conduct current laterally (X) along the rolled sheet 1802 without heating the rolled sheet 1802. The third electrode 1816 can also be formed as a thick portion of the rolled sheet 1802, or formed separately from the rolled sheet 1802 and attached to the rolled sheet 1802.

In some examples, the rolled sheet 1802 can further include a second substrate portion 1820 extending longitudinally (Z) between the second and third electrodes 1808, 1816. The second substrate portion 1820 can have an electrical resistance high enough to conduct current longitudinally (Z) between the second and third electrodes 1808, 1816 and resistively heat the second substrate portion 1820 in response to the current conducted there through.

A second dose 1822 of the herbal extract(s) can be disposed on the second substrate portion 1820 and configured to volatilize or entrain into a vapor or aerosol or in response to the resistive heating of the second substrate portion 1820. In some examples, the first and second doses 1814, 1822 include doses of the same herbal extract(s). In other examples, the first and second doses 1814, 1822 include doses of different herbal extract(s).

In some examples, the rolled sheet can include more than three electrodes, with a corresponding substrate portion between each pair of adjacent electrodes, and an herbal extract(s) dose disposed on each substrate portion of the substrate 1803. As described below in reference to FIGS. 22 and 23, a controller can be used to regulate how and when the herbal extract(s) doses are delivered to an individual.

Figure 19:
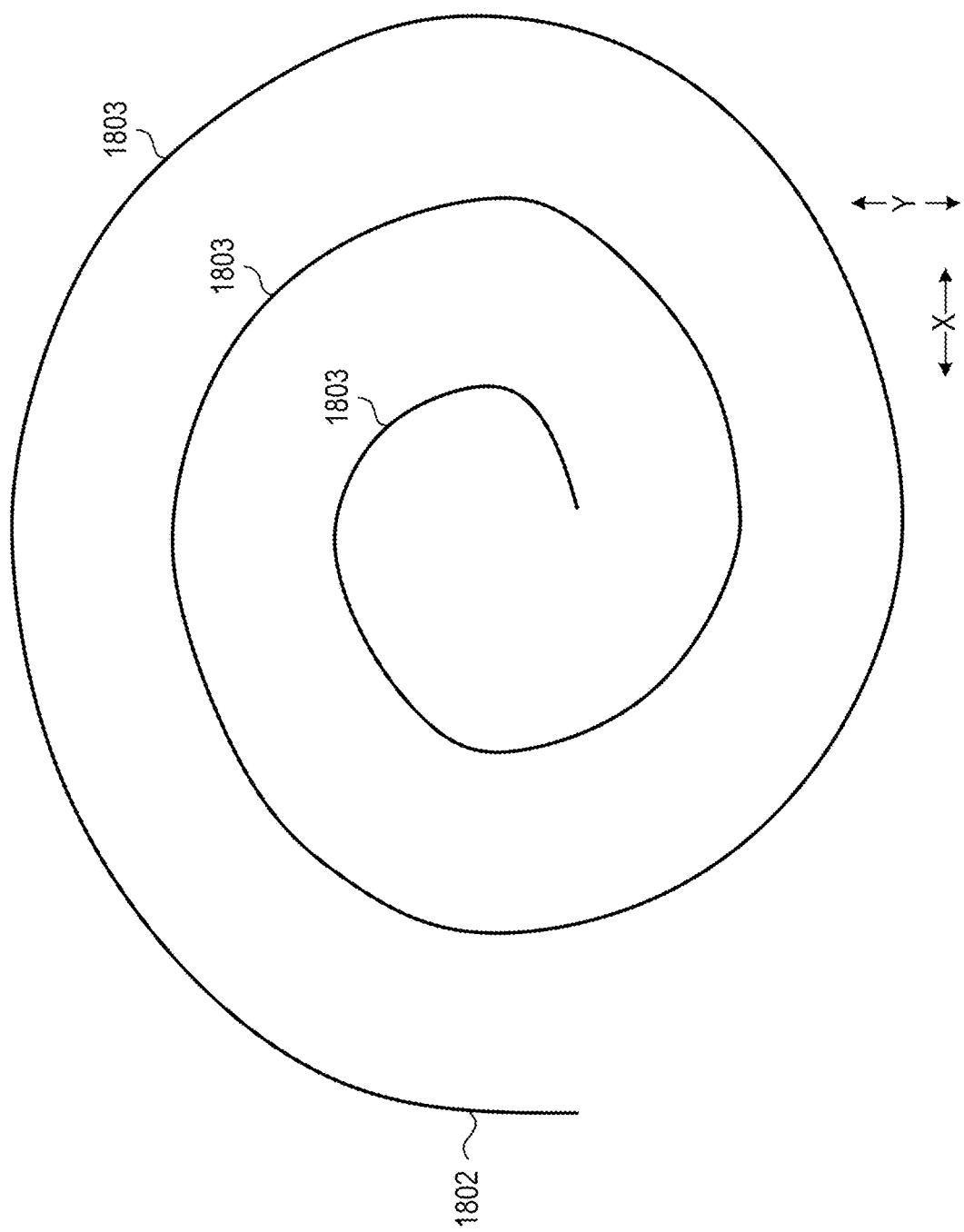
FIG. 19 shows a cross-section of the rolled sheet of FIG. 18.

FIG. 19 shows a cross-section of the rolled sheet 1802 of FIG. 18. In this example, the substrate 1803 is rolled to form a cylindrical structure having a spiral cross-section, when viewed from the first longitudinal end 1826 (FIG. 18) of the rolled sheet 1802. The first, second, and third electrodes are omitted from FIG. 19 for clarity.

Figure 20:
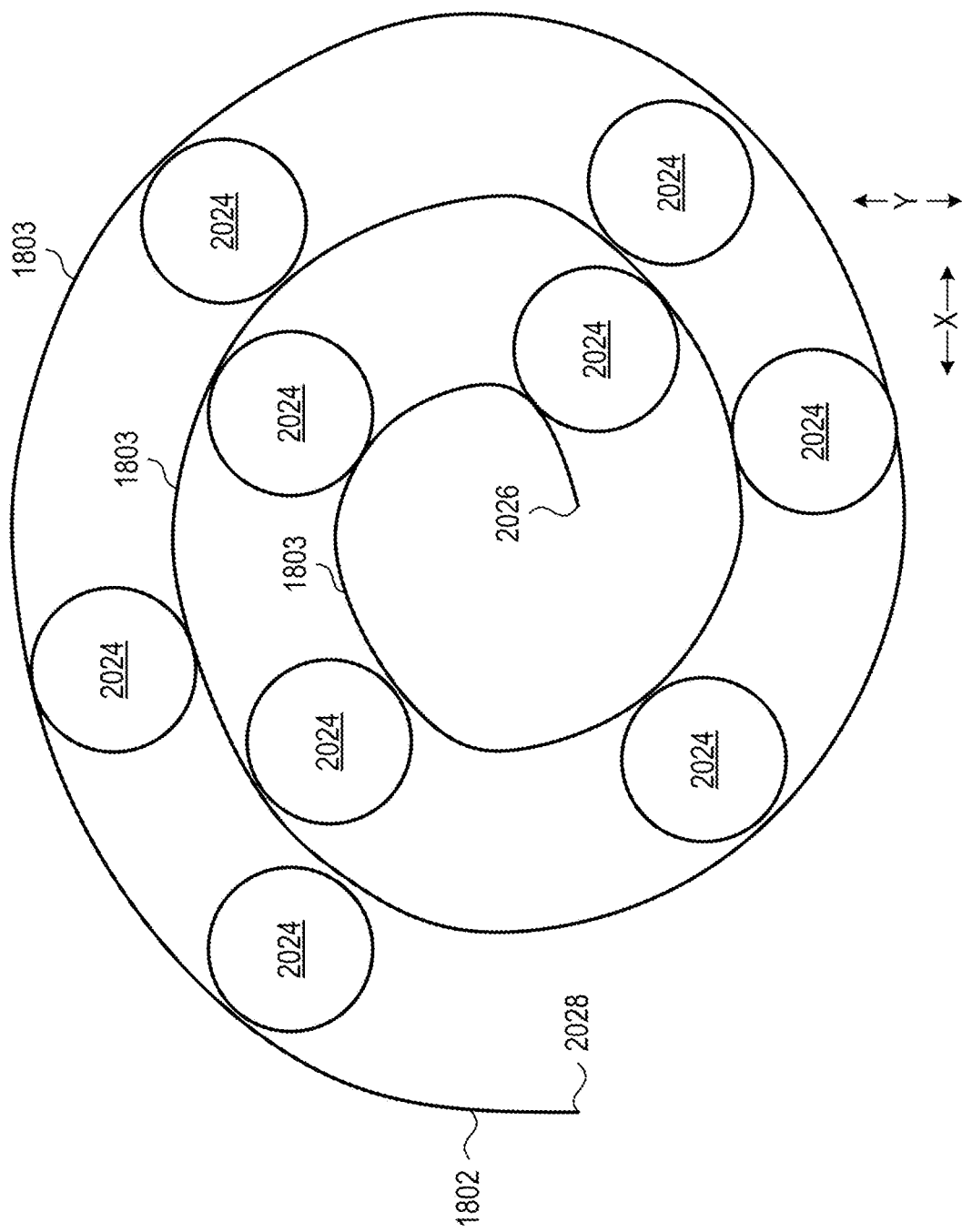
FIG. 20 shows the cross-section of the rolled sheet from FIG. 19, with the addition of an optional plurality of electrically insulating spacers positioned to space apart adjacent rolls of the rolled sheet.

FIG. 20 shows the cross-section of the rolled sheet 1802 from FIG. 19, with the addition of an optional plurality of electrically insulating spacers 2024 positioned to space apart adjacent layers of the substrate 1803. The spacers 2024 can be similar to the spacers described above in reference to FIGS. 7A and 7B. The electrically insulating spacers 2024 can be positioned and spaced apart to allow a gaseous flow in the interior of the rolled sheet 1802, along the longitudinal direction, from the first longitudinal end 1826 (FIG. 18) to the second longitudinal end 1828 (FIG. 18). The spacers 2024 can be added to the substrate 1803 prior to forming the rolled sheet 1802 or after the rolled sheet 1802 is assembled.

In the examples of FIGS. 18-20, the substrate 1803 is rolled in an open-ended manner to form the rolled sheet 1802, so that one of its lateral edges 2026 is disposed at the center of the rolled sheet 1802 and the opposite lateral edge 2028 is disposed at the exterior of the rolled sheet 1802. In other examples, the substrate 1803 can be assembled in a closed-ended manner, so that for some methods of assembly, its lateral edges can be joined during assembly to form a tube or other cylindrical structure.

Figure 21:
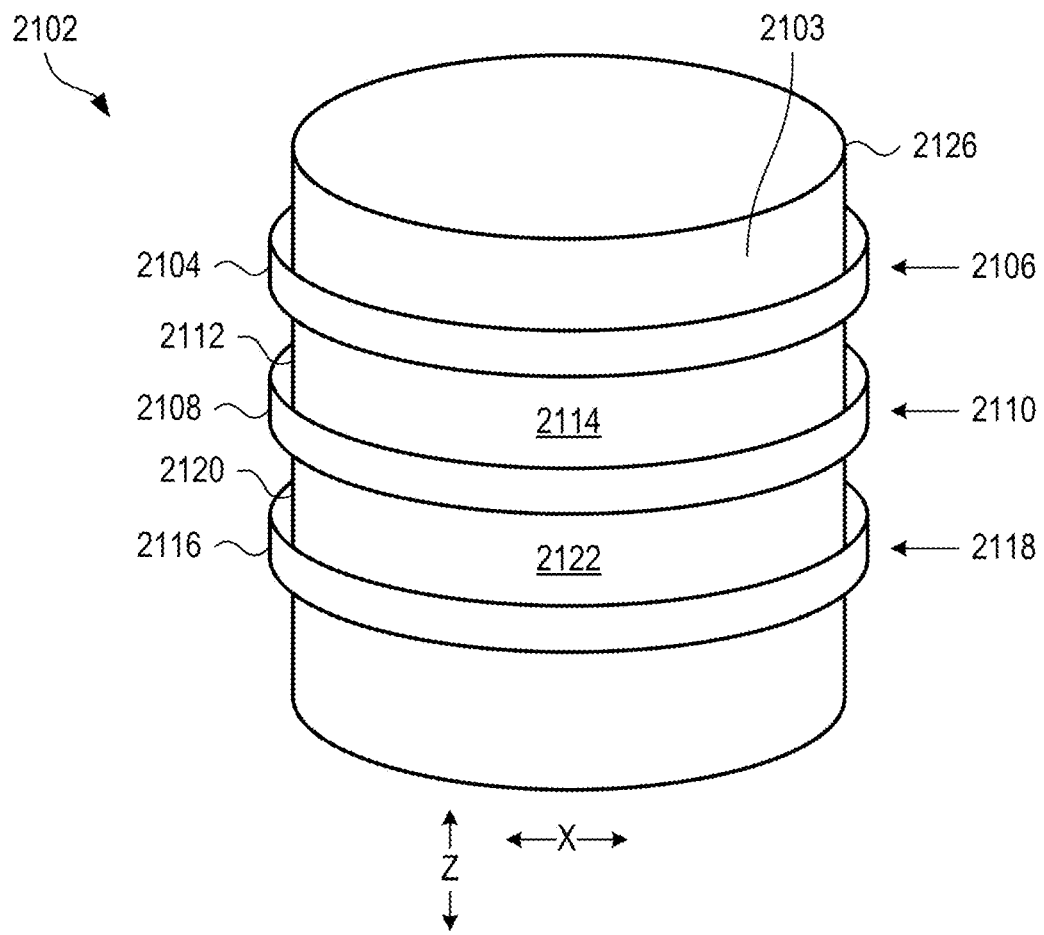
FIG. 21 shows another example of a cylindrically rolled sheet.

FIG. 21 shows an example of a tube 2102, suitable for use as a delivery cartridge in delivery system. In the example of FIG. 21, the tube 2102 has a circular cross-section, when viewed from a longitudinal end 2126 of the tube 2102. The tube 2102 is formed of a substrate 2103, and as described above, all or a portion of the substrate 2103 can be coated with herbal extract(s). The tube 2102 includes a first electrode 2104 at a first longitudinal location 2106, a second electrode 2108 at a second longitudinal location 2110, a first substrate portion 2112 extending longitudinally (Z) between the first and second electrodes 2104, 2108, a first dose 2114 of an herbal extract disposed on the first substrate portion 2112, a third electrode 2116 disposed at a third longitudinal location 2118, a second substrate portion 2120 extending longitudinally (Z) between the second and third electrodes 2108, 2116, and a second dose 2122 of an herbal extract disposed on the second substrate portion 2120. In some examples, only one side of the substrate 2103 is coated with the herbal extract(s) such that the herbal extract doses are disposed on the exterior of the tube 2102 or the interior of the tube 2102. In some examples, both sides of the substrate 2103 are coated with the herbal extract(s) such that the herbal extract(s) doses are disposed on the interior and exterior of the tube 2102.

In an example in which the cylindrical structure is a tube, like the tube 2102, the tube 2102 can be formed in at least the two ways described herein. Other processes can alternatively or additionally be used to form the cylindrical structure. In a first process, the first electrode 2104 can be open and have a lateral dimension generally equal to a lateral dimension of the substrate 2103. The first electrode 2104 can include a hinge, which can be generally located at a lateral mid-point on the first electrode 2104. It is recognized that the hinge can be at other lateral locations on the first electrode 2104, and more than one hinge can be used. The first electrode 404 and the substrate 2103 can be brought together such that the first and second lateral ends of each of the substrate 2103 and the electrode 2104 are generally aligned. The first and second lateral ends of the substrate 2103 and the electrode 2104 can then be connected together to form a closed, tubular structure, with the electrode 2104 connected to an exterior circumference of the substrate 2103. Additional electrodes can similarly be attached to the substrate 2103 to form a tube having multiple electrodes at various longitudinal locations on the substrate 2103.

In a second process, the first electrode 2104 can be a closed-end structure, having a generally circular shape; the substrate 2103 can be converted into a tube by joining the first and second longitudinal ends of the substrate 2103. The converted substrate 2103 can then be inserted into the circular electrode 2104 such that the electrode 2104 is connected to an exterior circumference of the substrate 2103. If the tube 2102 is intended to have multiple electrodes, the converted substrate 2103 can be separately inserted into each electrode, or the multiple electrodes can be longitudinally spaced from one another and the converted substrate 2103 can be inserted into the multiple electrodes in one step. In some examples, a support structure can be used to support the one or more electrodes as the converted substrate 2103 is inserted into the one or more electrodes.

One of ordinary skill in the art will appreciate that the delivery cartridge can have any suitable cross-section, such as spiral (FIGS. 17-20), circular (FIG. 21), elliptical, rounded and elongated, square, star-shaped, regular and irregular polygonal, and so forth.

Figure 22:
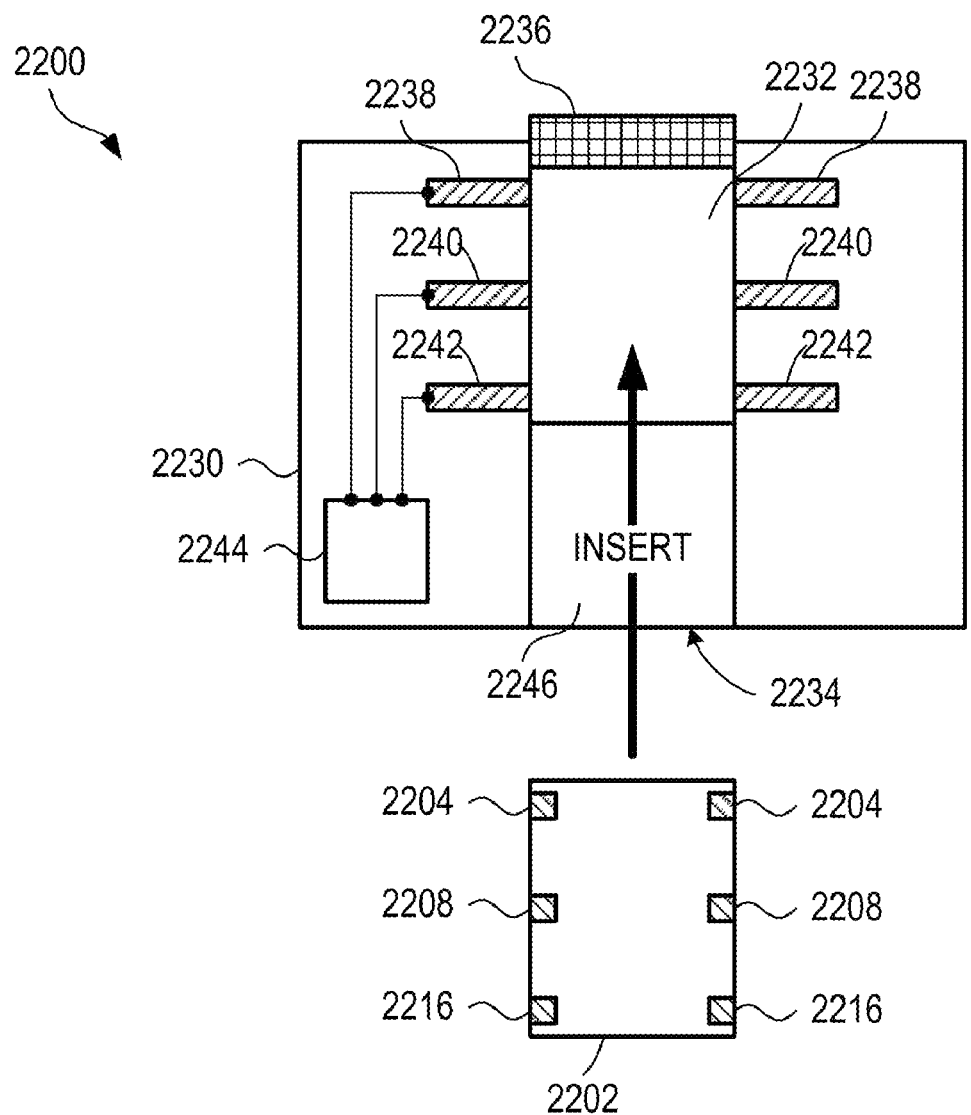
FIGS. 22 and 23 show examples of a delivery system with control circuit for providing multi-temperature staged heating of coated substrate.
Figure 23:
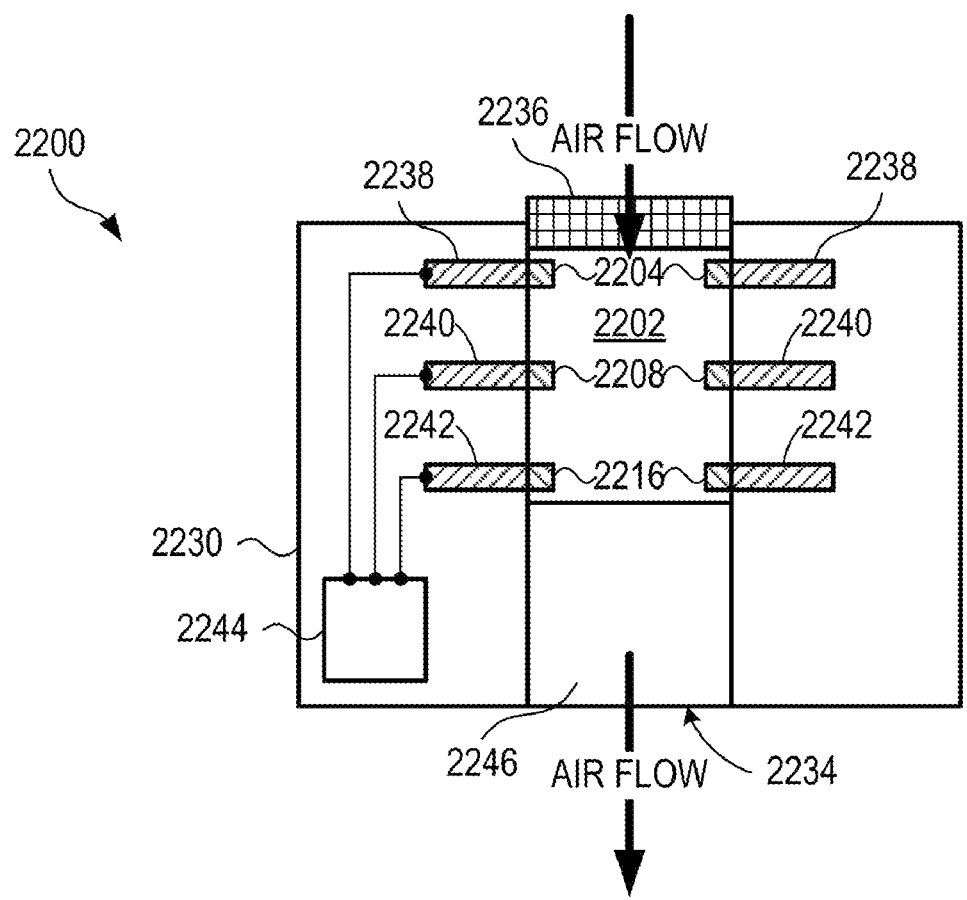

FIGS. 22 and 23 show an example of a delivery system 2200. The delivery system 2200 can include a delivery cartridge 2202, which can be similar to the rolled sheet 1802 (FIG. 17-20) or alternatively can be a tube such as the tube 2102 (FIG. 21). The delivery system 2200 can further include a housing 2230. FIG. 5 shows the rolled sheet 2202 separate from the housing 2230, which is how the delivery system 2200 can be arranged as sold or during storage. FIG. 23 shows the rolled sheet 2202 inserted into the housing 2230, which is how the delivery system 2200 can be arranged during use.

In some examples, the housing 2230 can be configured to be reusable, and the rolled sheet 2202 can be configured to be disposable or recyclable after the herbal extract dosages have been delivered. In some of these examples, the rolled sheet 2202 can be packaged as a replaceable cartridge. In other examples, the housing 2230 and rolled sheet 2202 can be packaged together, with one or both being configured to be disposable or recyclable after the herbal extracts dosages have been delivered. In some examples, the housing 2230 can be elongated and can include a first longitudinal end configured to deliver the volatilized gas into a user's mouth.

The housing 2230 can be configured to receive the rolled sheet 2202 within a cylindrical cavity 2232. The cylindrical cavity 2232 can be accessed through an opening 2234 in the housing 2230. In some examples, such as the example of FIG. 22, the opening 2234 can face a user, during use. In some of these examples, the opening 2234 is configured to deliver the aerosol or vapor into a user's mouth. For these examples, the housing 2230 can include an air filter 2236, attached to or made integral with the housing 2230, positioned on an opposite side of the cylindrical cavity 2232 as the opening 2234, and configured to filter air intake as air flows from outside the housing 2230, through air filter 2236, toward the cylindrical cavity 2232. In other examples, the opening 2234 can face away from a user, during use. In these examples, the rolled sheet 2202 can optionally include an air filter. In some examples, the cylindrical cavity 2232 and the rolled sheet 2202 can be keyed, or can include one or more locating features that can ensure that the rolled sheet 2202 is inserted into the cylindrical cavity 2232 with a specified rotational orientation. The housing 2230 can be designed to receive delivery cartridges having alternative shapes to the cylindrical design of the delivery cartridge 2200 by having the cavity 2232 in the housing 530 be sized and shaped to correspond to the size and shape of the delivery cartridge.

The housing 2230 can include a first housing electrode 2238 around a circumference of the cylindrical cavity 2232 and facing inward toward the cylindrical cavity 2232. The first housing electrode 2238 can be positioned longitudinally to respectively contact the first electrode 2204 of the rolled sheet 2202 when the rolled sheet 2202 is inserted into the housing 2230. The first housing electrode 2238, as well as additional housing electrodes, can be formed from stainless steel, aluminum, copper, or other suitable conductive materials.

The housing 2230 can include a second housing electrode 2240 around a circumference of the cylindrical cavity 2232 and facing inward toward the cylindrical cavity 2232. The second housing electrode 2240 can be positioned longitudinally to respectively contact the second electrode 2208 of the rolled sheet 2202 when the rolled sheet 2202 is inserted into the housing 2230. The first and second housing electrodes 2238, 2240 can be configured to deliver current between the first and second electrodes 2204, 2208 of the rolled sheet 2202. The first and second housing electrodes 2238, 2240 can be part of a heating element to deliver current between the first and second electrodes 2204, 2208 of the rolled sheet 2202 such that a portion of the rolled sheet 2202 can be resistively heated, as an alternative to using heated air.

The housing 2230 can optionally include a third housing electrode 2242 around a circumference of the cylindrical cavity 2232 and facing inward toward the cylindrical cavity 2232. The third housing electrode 2242 can be positioned longitudinally to respectively contact the third electrode 2216 of the rolled sheet 2202 when the rolled sheet 2202 is inserted into the housing 2230. The second and third housing electrodes 2240, 2242 can be configured to deliver current between the second and third electrodes 2208, 2216 of the rolled sheet 2202.

In some examples, the rolled sheet 2202 and housing 2230 can include more than three electrodes and housing electrodes, respectively. For these examples, each pair of adjacent housing electrodes can be configured to deliver current between a corresponding pair of adjacent electrodes of the rolled sheet.

In some examples, a controller 2244 can be positioned in the housing 2230. The controller 2244 can be configured to deliver current to the housing electrodes 2238, 2240 and 2242. In some examples, the controller can deliver current between the first and second housing electrodes 2238, 2240 at a first time to provide a first dose of an herbal extract to a user. In some examples, the controller 2244 can be further configured to deliver current between the second and third housing electrodes 2240, 2242 at a second time, different from the first time, to provide a second dose of the herbal extract to the user. For delivery cartridges that include multiple doses, the controller 2244 can be configured to deliver current between adjacent pairs of housing electrodes at sequential times to provide a dose of herbal extract to a user at each sequential time. In some examples, the controller 2244 can deliver current to multiple pairs of housing electrodes at the same time to deliver multiple doses to the user with a single inhalation. By using a conductive substrate and delivering current to the electrodes, the herbal extract(s) can be volatilized or entrained and inhaled by the user using room temperature air instead of heated air.

In some examples, the controller 2244 can include one or more batteries. In some examples, the controller 2244 can be rechargeable. In some examples, the controller 2244 can communicate with other electronic devices, such as through short-range wireless communication. In some examples, the controller 2244 can communicate with the Internet. In some of these examples, the controller 2244 can record a user's dosage history through wireless communication with another electronic device or through a web-based application. The controller 2244 can be triggered through a button on the housing 2230, through a touch-sensitive area on the housing configured to activate the controller 2244 when the 2230 housing contacts a user's mouth, or through another suitable trigger.

During use, as a user inhales, such as through opening 2234, the user can draw in air from the surroundings through the air filter 2236. The air from the surroundings can combine with the dose of the herbal extract released from the rolled sheet 2202 in an optional expansion/mixing chamber 2246. In some examples, the expansion/mixing chamber 2246 can be positioned between the rolled sheet 2202 and the user's mouth, during use.

After use, once the doses of the herbal extract(s) on the rolled sheet 2202 have been dispensed, the housing 2230 can eject or release the expended rolled sheet 2202. The expended rolled sheet 2202 can then be thrown away or recycled. In some examples, the housing 2230 can optionally include storage for one or more additional rolled sheets 2202.

Figure 24:
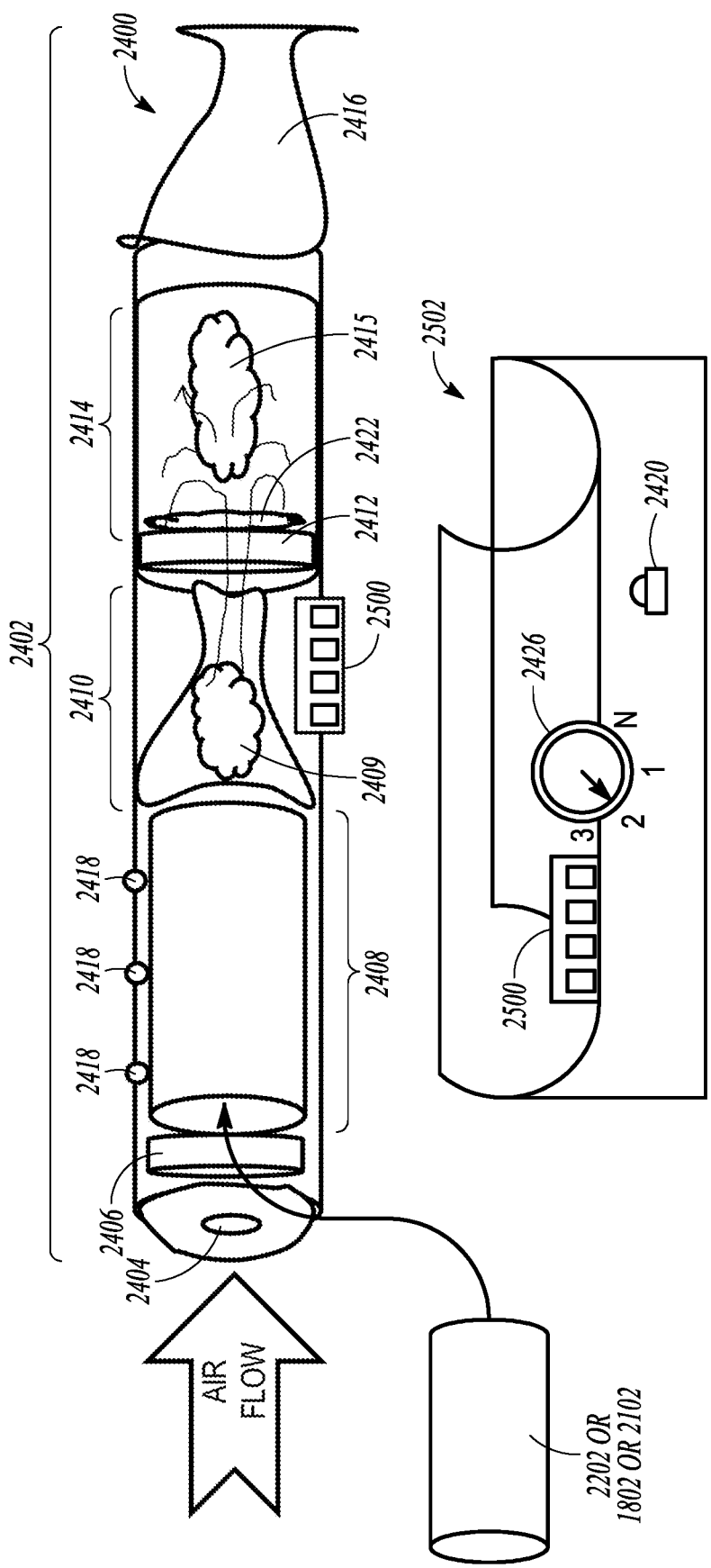
FIG. 24 is a side-view schematic drawing of another example of an herbal extract(s) delivery system.

FIG. 24 is a side-view schematic drawing of another example of a delivery system or nebulizer 2400. The example of FIG. 24 is sized and shaped for ease of use by a user. The delivery system 2400 can include a housing 2402.

An air intake nozzle 2404 can receive air flow from the surroundings and can optionally restrict the air flow into the housing 2402. In some examples, the air intake nozzle 2404 can be adjustable. In some examples, the air intake nozzle 2404 can allow a user to control the rate at which the surrounding air is taken into the housing 2402. In some examples, the air intake nozzle 2404 can control a duration of an inhalation. In some examples, the air intake nozzle 2404 can produce an internal nebulizer pressure when the user inhales.

Air passing through the air intake nozzle 2404 can pass through an air filter 2406. The air filter 2406 can prevent particles or particulate from entering further into the housing 2402. In some examples, the air filter 2406 can be the same in structure and function as the air filter 2236 (FIGS. 22 and 23).

Air passing through the air filter 2406 can enter a volatilizing or entraining chamber 2408. In some examples, the volatilizing chamber 2408 can accommodate delivery cartridges, such as 1802 (FIGS. 17 and 18), 2102 (FIG. 21), or 2202 (FIGS. 22 and 23). An interior of the volatilizing or entraining chamber 2408 can include electrodes that connect to corresponding electrodes on a rolled sheet during use. Air leaving the volatilizing or entraining chamber 2408 can include a prescribed dose of the herbal extract(s), which is volatilized or entrained from the cartridge during use (2409).

A vortex chamber 2410 can reduce a cross-section surface area of gas passing there through. The reduced surface area can increase the velocity of gas passing there through, which can be desirable.

Gas or vapor leaving the vortex chamber 2410 can optionally pass through a misting ring 2412, which can optionally inject mist from a misting reservoir 2422 into the gas. In some examples, the mist can include water. In some examples, the mist can include one or more flavorings or scents. The misting reservoir can alternatively be filled with an emulsion of water and squalene or mineral oil or paraffin oil. The emulsion can act as an adjuvant in substitution for the adjuvant layer described above.

In some examples, the misting ring 2412 can be activated by a controller, such as 2244 (FIGS. 22 and 23). In some examples, the misting reservoir 2422 is refillable. In some of these examples, the housing 2402 can define a port 2424, through which the misting reservoir 2422 can be refilled. In some of these examples, the material to refill the misting reservoir 2422 can be poured through the port 2424 in the housing 2402. In some examples, the material to refill the misting reservoir 2422 can be inserted via a cartridge, or other container, through the port 2424 in the housing 2402. As described further below in reference to FIG. 25, a pump can be used with the reservoir 2422 to deliver the solution from the reservoir 2422 to the misting ring 2412. As shown in FIG. 24, in an example, the misting reservoir 2422 can be located within the vortex chamber 2410. In other examples, the misting reservoir 2422 can be located in an alternative location within the housing 2402 or external to the housing 2402.

Gas or vapor leaving the misting ring 2412 can enter a mixing chamber 2414. The gas or vapor, moving with an increased velocity from the vortex chamber 2410, can expand within the mixing chamber 2414. This expansion can form a vortex, which can improve mixing of the mist with the gas or vapor (2415). The inclusion of a misting ring in the delivery system 2400 can be used to moisturize and cool the air leaving the volatilizing chamber 2408 and can improve inhalation of the vapors or aerosol from the delivery cartridge. The mist can be added to the vapors using additional or alternative features to the misting ring 2412. In an example, a misting solution can be packaged separately or together with a delivery cartridge. The misting solution can be available in different flavors to accommodate user preferences. It is recognized that the misting ring 2412 or comparable misting feature can be used in the other delivery systems described above. The misting ring 2412 can be used independently of the housing electrode design of FIG. 24. The delivery system 2400 of FIG. 24 can alternatively exclude the misting ring 2412.

Vapor or aerosol from the mixing chamber 2414 can exit the housing 2402 through a mouthpiece 2416. In some examples, the mouthpiece 2416 is removable from the housing 2402. A removable mouthpiece 2416 can help ensure sterility for the user. In other examples, the mouthpiece 2416 can be attached to and non-removable from the housing 2402.

The housing 2402 can include an optional status indicator, which can display visual indicia that indicate a status of the housing during use. In the example of FIG. 24, the status indicator can include three light emitting diodes (LEDs, 2418) radiating outward from the housing 2402. This is but one example of a status indicator; other suitable examples can also be used.

In the specific example of FIG. 24, each LED 2418 corresponds to a housing electrode and a corresponding electrode on the rolled sheet. In the specific example of FIG. 24, when the cartridge is inserted into the volatilizing or entraining chamber 2408, the controller can sense a voltage drop across adjacent pairs of electrodes, and can direct corresponding LEDs 2418 to glow red. In this example, a red color indicates that a corresponding dose on the rolled sheet is ready to be volatilized. In this example, a user can depress a button 2420 on the housing 2402, which can instruct the housing to direct current through a corresponding portion of the substrate. The button 2420 can operate as a 'go button'. In other examples, the button 2420 can include additional functionality with regards to operating the delivery system 2400. In the specific example of FIG. 24, when the user depressed the button for the first time, for a particular rolled sheet, corresponding LEDs can alternately blink red and green. In a specific example, blinking red and green can indicate that the controller is heating a selected dose on the rolled sheet. In some examples, the heating can take a relatively short period of time, such as two seconds. In some examples, when a dose is ready to be volatilized or entrained, a corresponding LED can turn solid green. In some examples, when a user depresses the button 2420 for a second time, the controller can monitor an internal pressure, such as in the volatilizing or entraining chamber 2408 or the mixing chamber 2414. In some examples, the controller can include a pressure sensor that detects a drop in pressure. When the pressure drops, corresponding to an inhalation by the user, the controller can volatilize or entrain the corresponding herbal extract dose on the rolled sheet. In some examples, the pressure sensor can provide a rate at which the herbal extract is being depleted to the controller. In some examples, one or more LEDs can blink at a rate indicative of the rate at which the herbal extract is depleted. In some examples, when the controller determines that a dose of the herbal extract is fully dispensed, one of more LEDs can turn off.

In other examples, more or less than the three LEDs 2418 can be used in the housing 2402. The LEDs as described above are but one specific example of a status indicator; other status indicators can also be used.

As shown in FIG. 24, the delivery system 2400 can optionally include a dose selection switch 2426 as part of the electronic controller module 2502 (schematically shown in FIG. 25) for selecting how many dosages are dispensed at one time from a delivery cartridge inserted in the chamber 2408. In some examples, the dose selection switch 2426 can include settings labeled as "1", "2", "3", up to the number of doses capable of being delivered from the cartridge. For example, if the dose selection switch 2426 is set to "3", then the delivery system 2400 can dispense three doses from the cartridge at one time. In operation, the controller module 2502 is removably and electronically connected with delivery system 2400 through the interface connectors 2500. The schematic representation of the connection and electronic control circuits of module 2502 is shown in FIG. 25.

Figure 25:
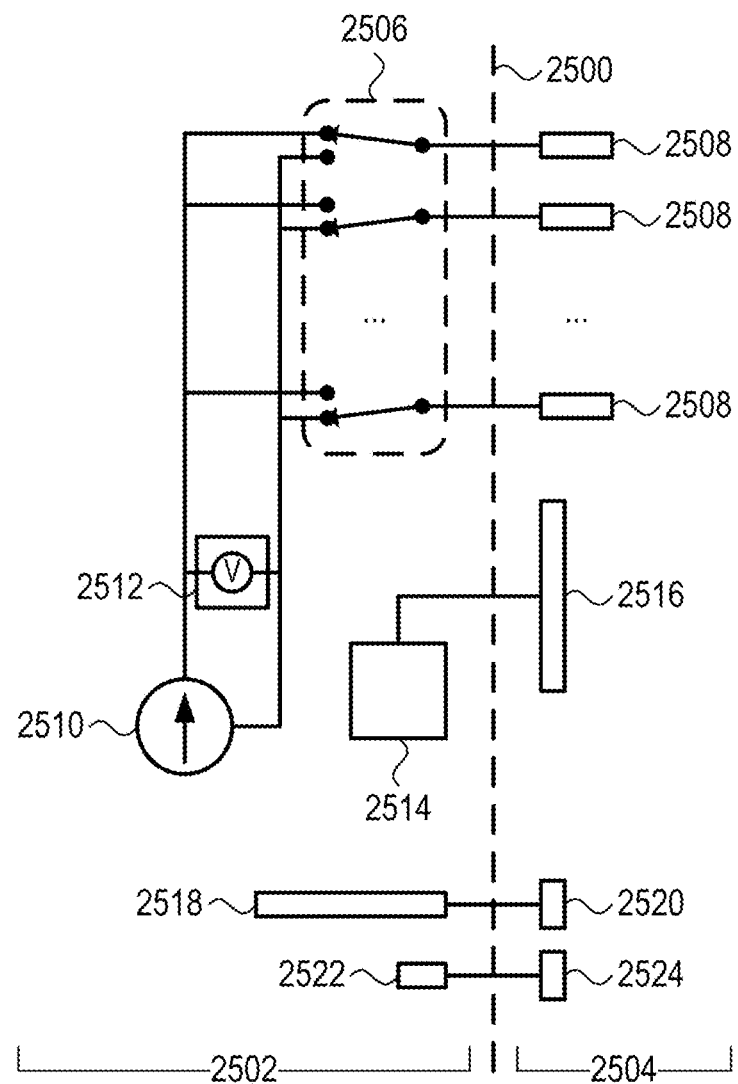
FIG. 25 is a schematic drawing of an example of an interface connector for use with a vaporizer nebulizer and controller.

FIG. 25 is a schematic drawing of an example of an interface connector 2500. The interface connector 2500 can form various connections, including electrical, hydraulic, and gaseous connections, between a controller 2502 for a vaporizing or entraining delivery system such as nebulizer 2400 (FIG. 24), which is the vaporizing or entraining nebulizer shown in outline form in FIG. 25 (2504). The interface connector 2500 is but one example of a connector; other suitable connectors can also be used. The vaporizing or entraining nebulizer 2504 is an outline of for example the nebulizer shown in FIG. 24 and can alternatively be other nebulizer shapes having similar functions. The controller 2502 can be external to the nebulizer 2504, attachable thereto, or integrally formed therewith. The interface connector 2500, the controller 2502 and the vaporizing or entraining nebulizer 2504 can be part of the delivery system.

A controllable switching matrix 2506 can control voltages directed to each electrode 2508 on a delivery cartridge usable in the vaporizing or entraining nebulizer 2504. The controller 2502 can include a controllable current source 2510 to generate the current, and a voltage detector 2512 to monitor the voltage across the leads of the current source 2510. The controllable switching matrix 2506 can controllably switch the electrical connection of each electrode between the two sides of the current source 2510, thus switching or alternating a voltage applied to each electrode between a relatively low value and a relatively high value. When the relative voltages between a pair of adjacent electrodes 2508 are equal (e.g., both relatively low or both relatively high), then no current flows between the electrodes 2508. When the voltages between the pair of adjacent electrodes 2508 are different (e.g., one relatively low and one relatively high), then current flows from the electrode having the relatively high voltage to the electrode having the relatively low voltage. The current generates heat, and the heat volatilizes the desired dose of the herbal extract, which is disposed between the electrodes 2508 in the pair, as described above. The controller 2502 can track which doses have been volatilized or entrained, so that current is directed through each adjacent pair of electrodes 2508 only a single time during use of a particular delivery cartridge.

As shown in FIG. 25, a misting reservoir and pump 2514 can be included in the same mechanical housing as the controllable switching matrix 2506 and, in an example, can be housed within the controller 2502. The interface connector 2500 can hydraulically connect the controller 2502 to the vaporizing or entraining nebulizer 2504 such that the misting reservoir and pump 2514 can controllably direct a specified volume of mist, through the interface connector 2500, to a mister 2516, such as a misting ring 2412 (FIG. 24). In some examples, the controller 2502 supplies a fixed volume of mist for each dose of the herbal extract. In some examples, the controller 2502 allows a user to select the volume of mist for each dose of the herbal extract. For instance, the mist volume can be selected mechanically, such as with a knob, level, or button on the housing. Alternatively, the mist volume can be selected electronically, such as by one or more buttons on the housing of the vaporizing or entraining nebulizer 2504 or the controller 2502.

A pressure sensor 2518 can be included in the controller 2502. The pressure sensor 2518 can measure one or more pressures in the delivery system 2504, such as at an orifice 2520, which can be located, for example, proximate to the mouth of the user. In some examples, the controller 2502 can use the pressure sensor 2518 as a trigger switch, which can trigger additional actions from the controller 2502. When the user inhales from the vaporizing or entraining nebulizer 2504, the pressure at a particular location, such as at the orifice 2520, drops. The pressure sensor 2518 can detect the drop in pressure, and the controller 2502 can take a suitable action, such as directing suitable voltages to the electrodes 2508 to initiate delivery of an herbal extract dose, and/or directing the misting reservoir 2514 to dispense mist. In other examples, the controller 2502 can connect to a Get Ready/Go button on the housing, similar to the button 2420 shown in FIG. 24, to trigger suitable actions.

The interface connector 2500 can optionally include additional electrical connections between the controller 2502 and the vaporizing or entraining nebulizer 2504. For instance, an optional LED controller 2522 can electrically connect, through the interface connector 2500, to one or more LEDs 2524 on or in the housing. In some examples, the controller 2502 can additionally connect to a dose selection switch disposed on the housing. In some examples, the controller can electrically connect to a power source disposed on or in the housing.

Although several features, for example, the misting reservoir and pump 2514, are described above as being part of the controller 2502, it is recognized that some or all of these features do not have to be physically contained within the same housing as the controller 2502 but can still be controlled by the controller 2502.

It is recognized that a delivery system, like the system 2400 of FIG. 24, can exclude a controller, or a controller could be used having more or less features as the controller 2502 shown in FIG. 25. In a delivery system that excludes a controller, a user can manually control operation of the electrodes (or other means of volatilizing or entraining the one or more herbal extracts), or similarly, the user can manually deliver a misting solution to a mixing chamber by manually activating the pump for the mist reservoir.

Figure 26A:
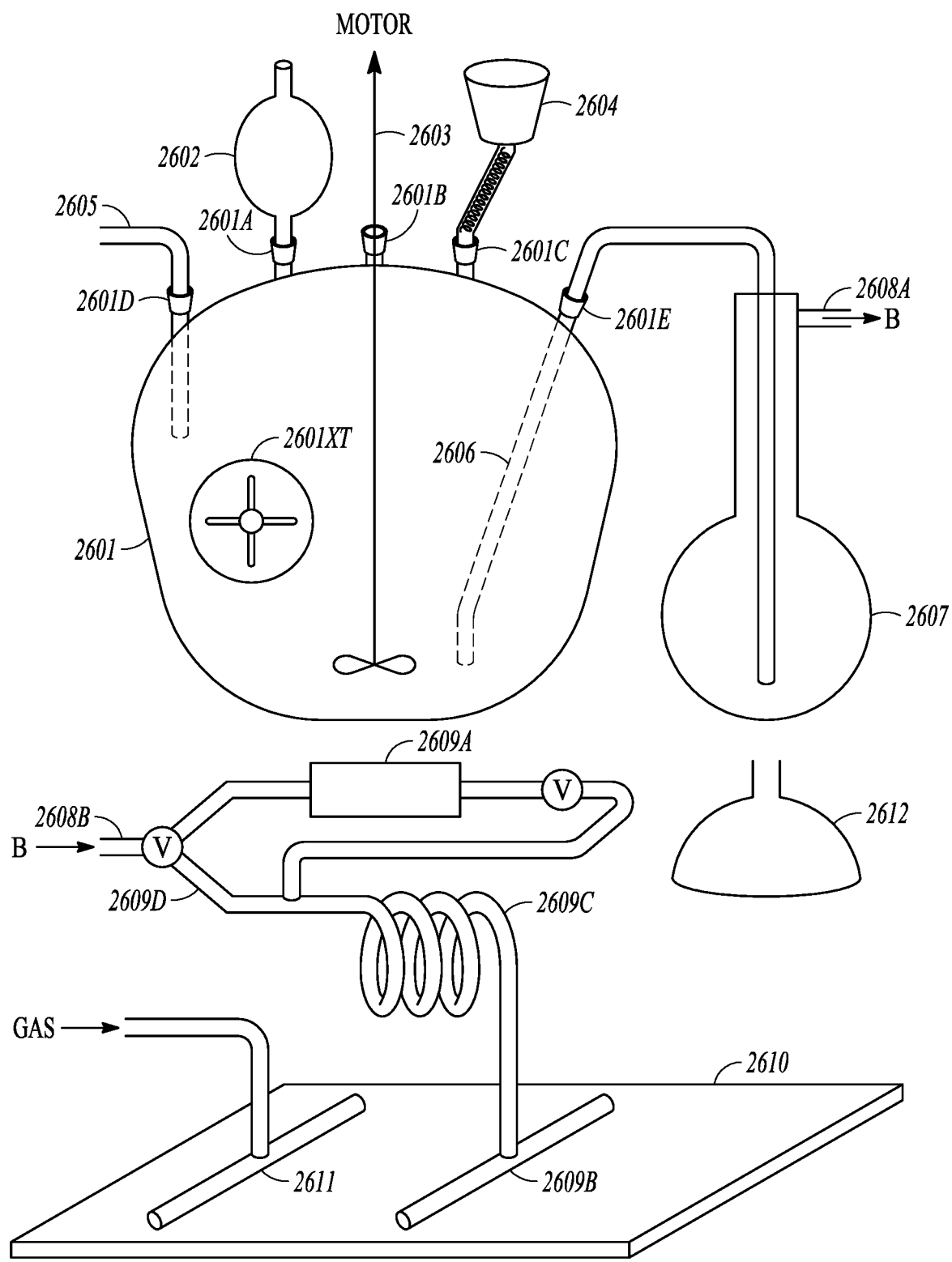
FIGS. 26A and 26B are schematic drawings of a wet extraction process and device and remote multi-storage and deposit unit.
Figure 26B:
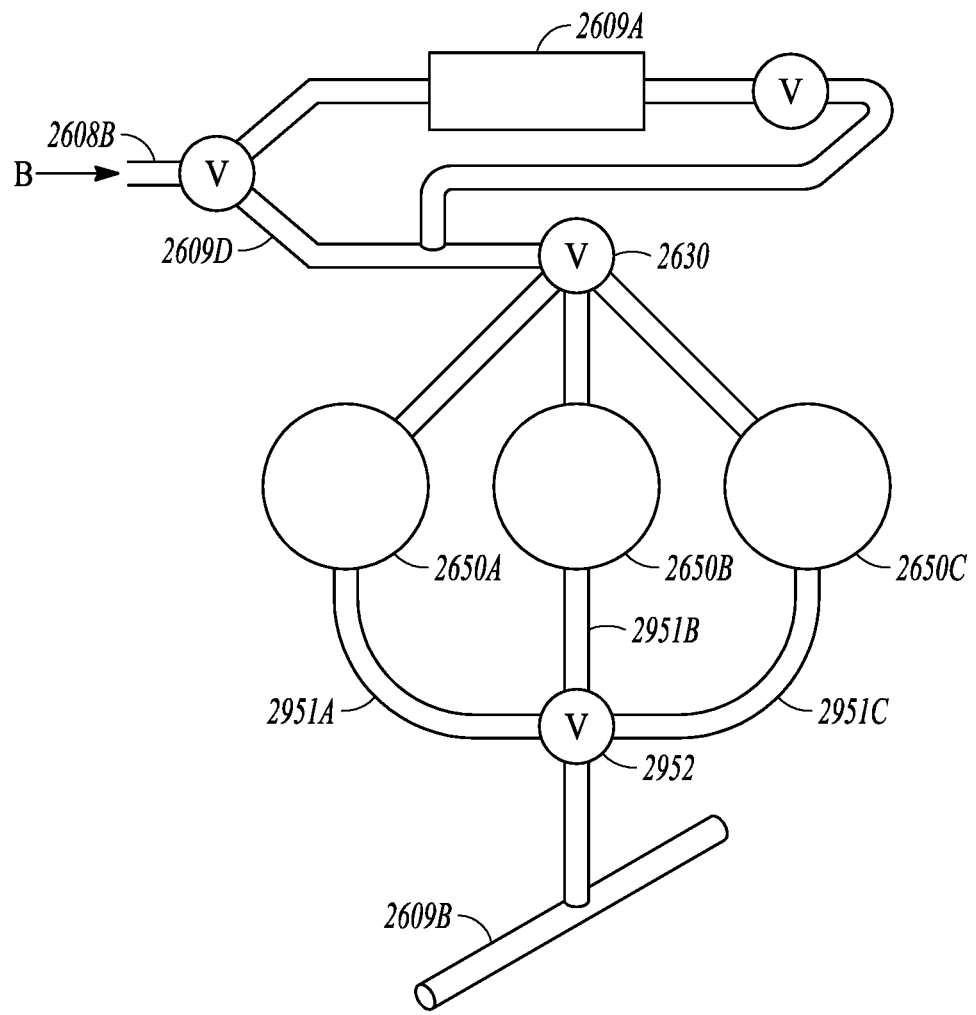

FIG. 26A is a perspective representation and schematic of an example of a wet extraction apparatus with casting chamber for formation of a substrate coated with an herbal extract. A large container for conducting the wet extraction of herbal extract from the herbaceous plant material is the operational device for performing this process. Typically, the large container is a five portal vessel 2601 that can be any size chemical operation vessel ranging from 1 L to 10,000 L or larger. The five portals of the vessel (2601A, B, C, D and E) provide access, delivery and inlet openings to the interior of the vessel. Door 2601XT in extraction vessel 2601 allows large scale access to the interior of the vessel and enables removal of residual herbaceous plant material after the extraction process. Although any arrangement of inlet portals is within the scope of the invention, this example provide separate inlets for the various substances and solvents as well as operational devices. Inlet 2601A is removably connected to a container (solvent container 2602), typically an addition funnel, with valve for variable rate introduction of solvent into the extraction vessel 2601. Inlet 2601B is removably connected to a stirring rod and paddle 2603. The rod and paddle extend into the interior region of the vessel, are powered by a variable speed electric motor (not shown) and provide distribution and mixing of the plant material and solvent. Inlet 2601C is removably connected to a hopper with slide valve for delivery of the herbaceous plant material to the vessel 2601 (delivery hopper 2604). Preferably the herbaceous plant material is cleaned, dried and comminuted into very small particles. Transport of the particles from the delivery hopper into the extraction vessel may be accomplished by gravity flow, pressurized delivery or mechanical transport through the delivery chute. Inlet 2601D is removably connected to a tank of inert gas (gas tube 2605). If the herbal extract is oxidation sensitive, a cloud or atmosphere of inert gas such as nitrogen or argon may be introduced over the solution of solvent and plant material. Inlet 2601E is removably connected to an outlet tube capped at its distal end with a glass frit or other screen material (outlet tube 2606). The outlet tube extends into the interior of the vessel and the frit or screen resides at the bottom of the extraction vessel. Outlet tube 2606 is optionally, removably connected to a trap having an inlet and outlet (trap 2607). The outlet tube 2606 will carry solution and residue of plant material into the trap 2607. The trap allows the residue to settle and enables further transport of clean solution to a concentrator to remove substantially most of the solvent from the solution, provide a concentrate and the concentrate delivered to distribution tube 2608a. If trap 2607 is not needed, it can be bypassed and solution delivered to a concentrator to remove substantially most of the solvent from the solution, provide a concentrate and the concentrate delivered to distribution tube 2608A.

Distribution tube 2608A is removably and variably connected through a Y tube with valve 2608B to a chromatographic column 2609A on one side of the Y tube and a fine flow spray tube 2609B on the other side of the Y tube through a transport tube 2609C. The valve of Y tube 2608B directs solution flow either to cylinder 2609A or to spray tube 2609B through transport tube 2609C. The outlet of cylinder 2609A connects to a valve arrangement and hence to spray tube 2609B. Spray tube 2609B is movably positioned over casting basin 2610 and is designed to deliver a fine sheet of concentrate onto the casting basin. Spray tube 2609B can be transported along the length of the casting basin so as to deliver a layer of concentrate into the casting basin. Also movably positioned over casting basin 2610 is evaporator tube 2611. Evaporator tube 2611 is positioned at an appropriate distance behind spray tube 2609B. Evaporator tube 2611 is connected to a tank of dry inert gas and is equipped with an exhaust hood 2612. The combination of the evaporator tube, gas and exhaust hood enable evaporation of solvent from the cast solution in the casting basin so as to provide a dried layer of herbal extract.

In operation, finely divided herbaceous plant material that preferably has been cleaned and dried to remove water is placed into delivery hopper 2604. The valve or other transport mechanism for delivery of the material to the vessel 2601 is actuated and an appropriate amount of material is delivered to the vessel. Solvent container 2602 is filled with an appropriate solvent in which it is known that the herbal extract is soluble. The solvent container valve is actuated and an appropriate amount of solvent added to the vessel 2601. The stirring rod/paddle 2603 is actuated and the solution of solvent and plant material stirred. Heat may be applied to the solution through a heating mantle around the vessel (not shown). The temperature of the heating process can be appropriately controlled so as to increase the rate of extraction of the herbal extract from the material but not to volatilize the solvent to a great extent. Additional solvent may be added from time to time to replenish solvent loss.

After an appropriate time for achievement of extraction of the herbal extract from the material, gas flow from gas tube 2605 is initiated. At the same time, the valve of the solvent container 2602 is checked to assure it is closed and the gas tight seal around the stirring rod/paddle is checked to assure sealing. The flow of inert gas into flask 2601 increases the internal pressure and causes the solution to flow out through the outlet tube 2606. The glass frit or screen at the distal end of the outlet tube 2606 provides separation of solution from residual plant material. The increased pressure inside vessel 2601 causes the solution to transport optionally into trap 2607 as the trap fills with solution, any residual plant material carried by the solution settles to the bottom of the trap. Clean solution passes from the trap outlet tube into distribution tube 2608a. If the solution from tube 2606 is clean, trap 2607 can be bypassed and the solution delivered directly to tube 2608A. Distribution tube 2608a connects with Y tube and valve 2608B. The Y tube valve can control delivery of the solution either to a chromatography column 2609A or to spray tube 2609B.

Delivery to chromatography column 2609A is an option for further purification of the herbal extract in the solution. The column may be a silica gel, diatomaceous earth, cellulose, cellulose derivatives, alumina, polystyrene microparticles and similar chromatographic materials. Passing the solution through the column will separate a mixture of substances in the herbal extract such that each substance will exit the column at a different time owing to its retention factor in the column material. In this fashion, a gross herbal extract can be further refined to a particular substantially purified substance. Identification of the various fractions can be made by UV and/or IR identification of the fraction at the outflow end of the column (not shown). If the column 2609A is chosen for passage of the solution, the chromatographed, desired herbal extract exiting the column may be directed to the next appropriate step.

With the passage of solution through either column 2609A or by bypassing column 2609A, the solution can be optionally and preferably concentrated by vacuum evaporation of a significant portion of solvent. This may be accomplished for example by roto-vacuum evaporation on a roto-stripper (not shown). The solution is concentrated into a concentrate with a minimum amount of solvent present to enable the concentrate to flow.

The concentrate from vacuum evaporation may be transported to spray tube 2609B. The spray tube is utilized to lay down a broad flat sheet of concentrate into casting basin 2610. Spray tube 2609B is dimensioned so that its length spans the width of the casting basin. Spray tube 1609B has a slit running its entire length so that the spray of concentrate out of the spray tube constitutes a continuous sheet of spray. Into casting basin 2610 is prepositioned substrate 2012. The dimensions of the casting basin and the substrate are coordinated so that the substrate fits tightly into the casting basin. The edges of the substrate seal against the sides of the casting basin so that concentrate is unable to seep past the edges and down underneath the substrate. The edges of the casting basin are higher than the thickness of the substrate and the sheet of concentrate to be laid down so that the sheet of concentrate is held in a stationary configuration on top of the substrate. As concentrate flows out through the slit of spray tube 2608B, the tube may be moved along the length of casting basin 2610 or spray tube 2608B may be remain stationary above casting basin 2610. Because the concentrate is liquid, it will seek its own uniform level on the substrate 2612 in casting basin 2610 when spray tube 2608B is stationary. Nevertheless, transport of spray tube 2608B along the length of casting pan 2610 is preferred. At an appropriate distance and time following the operation of spray tube 2608B, evaporator tube 2611 is actuated to emit a sheet of inert gas to evaporate the solvent from the layer of concentrate laid down on the substrate 2612. Evaporator tube 2611 spans the width of the casting basin and is configured with a thin slit or with a line of holes along its long axis. The slit or holes are arranged to direct a stream of inert gas substantially parallel and at some distance above the casting pan. Preferably, evaporator tube 2611 can be rotated around its long axis so as to direct to flow of inert gas upward and perpendicular to the substrate, or at any rotary angle form upward and perpendicular to downward and perpendicular. Evaporator tube 2611 also can be moved along the length of the casting basin, i.e., is translatable along the length of the casting basin so that it will translate from one end to the other of the casting basin. In operation, the evaporator tube is actuated after completion of the deposit of concentrate on the substrate. The flow of inert gas is first directed upward so as to evaporate a substantial portion of the solvent from the deposited concentrate. As the deposited concentrate become sticky to tacky and tends toward dryness, the flow of inert gas is directed more and more downward so as to continue drying and finally leaving a dried layer of herbal extract on the substrate.

This process can be repeated to deposit multiple layers of herbal extract. For subsequent layers, the evaporator tube preferably is operated substantially soon after the spray tube has deposited a sheet of concentrate. In this fashion, a subsequent sheet of concentrate is dried fairly rapidly as it is laid down so that the underlying layer of herbal extract is not re-dissolved.

It is preferred to include an exhaust hood above the casting basin, spray tube and evaporator tube so that evaporated solvent can be captured and disposed of without exhausting solvent into the atmosphere.

Solvents useful for wet extraction include water, chloroform, ether, ethyl alcohol, glyme, hexane, and similar polar protic or polar aprotic or nonpolar organic solvents having boiling point below 100° C.

As an alternative, as described and depicted in FIG. 26B, a wet extraction process can be employed to produce a series of solutions of herbal extracts held in remote storage vessels 2950A, B and C. On the other side of the process, individual hoppers 2604 A, B and C are used to deliver different herbaceous plant material to the extraction vessel 2601. Each hopper can contain a different individual herbaceous plant material. The chutes of the individual hoppers can be actuated to deliver the herbaceous material to extraction vessel 2601 through inlet 2601C. Following the wet extraction, the solution can be transported to an individual storage vessel, one of vessels 2650 A, B and C. The residual herbaceous material remaining in extraction vessel 2601 can be removed through door 2601XT.

The storage vessels 2651 A, B and C will have inlets connected by a multi directional flow controller (a multiple position valve assembly 2630) to delivery tube 2609D. The controller 2630 can direct the flow of different solutions of herbal extract to individual storage vessels 2651 A, B and C. When needed, the multi-positional valve 2952 connected to the outlets 2951A, B and C of the storage vessels can be actuated and the appropriate solution from a chosen storage vessel delivered to a concentrator (vacuum evaporator) and the concentrate delivered to slit tube 2609*b*. The concentrate from storage vessel 2950 A, B or C may be cast as an individual herbal extract layer on a substrate or as one of a multiple number of layers on a substrate as described above.

There can be potential advantages to delivering the herbal extract(s) using the delivery cartridges described herein. For instance, the herbal extract(s) dosage and purity can be accurately controlled during the manufacturing process. In some examples, an advantage can include allowing a user to ingest herbal extract(s) in a safe, repeatable accurate dose suitable for research and clinical trials. In some examples, an advantage can include forming the cartridge from recyclable aluminum. In some examples, an advantage can include depositing the herbal extract(s) onto the aluminum substrate in a carefully controlled and regulated process, transported to the user. In some examples, an advantage can include removing the toxins during factory processing and disposing of the toxins properly. In some examples, an advantage can include recycling the cartridge, with no waste. In some examples, an advantage can include convenience for the user, and lack of smoke when used. In some examples, an advantage can include disposing multiple doses on a single cartridge, which further enhances convenience, functionality as well as lowering shipping cost. In some examples, an advantage can include the flexibility in accurately setting a dose level, which can provide functionality to both users and researchers alike. In some examples, an advantage can include optionally adding a moisturizing mist, and perhaps a pleasant flavor, which improves the overall experience and comfort for the user.

Embodiments

The present application provides for the following exemplary embodiments, the numbering of which is not to be construed as designating levels of importance:

Embodiment 1 provides a method of purifying an herbal extract from an herbaceous plant composition and the method can comprise heating the composition to a first temperature to volatilize the herbal extract into a first vapor, and condensing the first vapor onto a substrate to form a first coating, the first coating comprising the herbal extract Embodiment 2 provides the method of Embodiment 1 optionally configured to provide multiple layers of herbal extracts, each layer being a different herbal extract. The method comprises practice of embodiment 1 to provide a first coating and optionally further comprising, after forming the first coating, heating a second herbaceous plant composition to a second temperature to volatilize a second herbal extract into a second vapor, and condensing the second vapor onto the substrate to form a second coating over the first coating, the second coating comprising the second herbal extract. As an option of embodiment 2, one of the herbal extracts may be a *Cannabis* extract.

Embodiment 3 provides the method of Embodiment 1 optionally configured such that the substrate includes a first side and a second side and the first coating is formed on the first side of the substrate and comprises the first herbal extract. The method optionally further comprises heating the second herbaceous plant composition to volatilize the second herbal extract into a second vapor and condensing the second vapor onto the second side of the substrate to form a second coating, the second coating comprising the second herbal extract. As an option of embodiment 3, one of the herbal extracts may be a *Cannabis* extract.

Embodiment 4 provides the method of Embodiment 1 optionally configured such that the first coating comprises the first herbal extract and the method optionally further comprising, after forming the first coating, heating the second herbaceous plant composition to volatilize the second herbal extract into a second vapor, and condensing the second vapor onto a second substrate to form a coating comprising the second herbal extract. As an option of embodiment 4, one of the herbal extracts may be a *Cannabis* extract.

Embodiment 5 provides the method of Embodiment 1 optionally configured such that the first temperature is equal to or greater than a temperature sufficient to volatilize the first herbal extract.

Embodiment 6 provides the method of any of Embodiments 1-5 optionally configured such that condensing the first vapor onto a substrate includes placing the substrate on or near a cooling bar.

Embodiment 7 provides the method of any of Embodiments 1-6 optionally configured such that the herbaceous plant composition is one or more of the flowers, seeds buds, leaves, stems, branches, bark and/or roots of the herbaceous plant.

Embodiment 8 provides the method of Embodiment 7 optionally further comprising processing the herbaceous plant composition by comminuting the flowers, buds, seeds, leaves, stems, branches, bark and/or roots into very small pieces prior to heating the raw herbal extracts.

Embodiment 9 provides a method of pre-treating the very small pieces of herbaceous plant material of Embodiment 8 by drying the very small pieces in air at ambient temperature to slightly above ambient temperature to remove water, and optionally collecting the removed water and separating any herbal extract present in the removed water.

Embodiment 10 provides the method of Embodiment 9 optionally further comprising vacuum drying the very small pieces of herbaceous plant material to produce vapors composed of water and herbal extracts, collecting the vapors by condensation and separating the herbal extracts from the water by dissolution of the herbal extracts with a water immiscible solvent.

Embodiment 11 provides a method of making a delivery cartridge and can comprise practice of Embodiments 1-10 followed by converting the coated substrate into a three-dimensional structure configured for use as a delivery cartridge.

Embodiment 12 provides the method of Embodiment 11 optionally configured such that converting the coated substrate includes rolling the coating substrate to form a spirally-wound cylindrical shape.

Embodiment 13 provides the method of Embodiment 12 optionally configured such that a plurality of spacers is placed along the coated substrate prior to converting. The plurality of spacers can be configured to allow for airflow through the spirally-wound cylindrical shape.

Embodiment 14 provides the method of Embodiment 11 optionally configured such that the coated substrate comprises a first end and a second end opposite to the first end and the method can further comprise creating a plurality of notches at multiple locations on the coated substrate between the first and second ends. The notches can create an interface and an interval between adjacent notches defines a segment of coated substrate. The method can further comprise bending the segments relative to one another at the interfaces so as to form a saw-tooth pattern.

Embodiment 15 provides the method of Embodiment 14 optionally further comprising connecting the first end to the second end to form a closed polygonal shape.

Embodiment 16 provides the method of any of Embodiments 11-15 optionally further comprising ascertaining an average amount of the herbal extract(s) in the coating per unit area of the coated substrate.

Embodiment 17 provides the method of any of Embodiments 11-16 optionally configured such that converting the coated substrate into a three-dimensional structure includes determining a total area of the coated substrate to use for the three-dimensional structure based on a predetermined amount of the herbal extract(s) in the delivery cartridge.

Embodiment 18 provides the method of any of Embodiments 11-17 optionally further comprising attaching one or more layers to the coated substrate prior to converting the coated substrate into a three-dimensional structure, the one or more layers configured to provide at least one of flavor or adjuvant substance with the herbal extract(s).

Embodiment 19 provides the method of any of Embodiments 11-18 optionally further comprising depositing multiple overlapping or sequential layers of herbal extract(s) on one or both sides of the substrate, the multiple layers each being a different herbal extract.

Embodiment 20 provides the method of any of Embodiments 11-19 optionally configured such that the vaporization temperatures for producing the herbal extract vapors are selected according to the known vaporization temperatures of the individual herbal extract(s).

Embodiment 21 provides a delivery product comprising a coated substrate with one or more coating layers, the one or more coating layers including one or more herbal extracts Embodiment 22 provides the delivery product of Embodiment 21 optionally configured such that the coated substrate is converted into a three-dimensional structure configured to maximize surface area of the three-dimensional structure and allow for passage of air through the three-dimensional structure, in order to volatize the herbal extract(s) for inhalation by a user when heat is applied to at least one of the three-dimensional structure or the air passing through the three-dimensional structure.

Embodiment 23 provides the delivery product of Embodiment 22 optionally configured such that the three-dimensional structure is a cylindrical shape having multiple layers of the coated substrate, and the three-dimensional structure is formed by rolling the coated substrate into a spiral.

Embodiment 24 provides the acts delivery product of Embodiment 22 optionally configured such that the three-dimensional structure is tubular and includes a longitudinal opening extending from a first end to a second end of the three-dimensional structure, and a cross-section of the three-dimensional structure is a polygon.

Embodiment 25 provides the delivery product of Embodiment 22 optionally configured such that the three-dimensional structure is rectangular and includes multiple layers of the coated substrate folded in a saw-tooth pattern and compressed together to form the rectangular shape.

Embodiment 26 provides the delivery product of any of Embodiments 22-25 optionally in combination with a delivery device configured to receive the three-dimensional structure and comprising a heating element for heating the three-dimensional structure to volatilize or entrain the herbal extract(s) in the three-dimensional structure into a vapor or aerosol.

Embodiment 27 provides the delivery product of Embodiment 26 optionally configured to have multiple layers of herbal extracts, each layer being a different herbal extract and the volatilization or entrainment of the herbal extract(s) is simultaneous or sequential and is controlled by management of the heating temperature produced by the delivery device.

Embodiment 28 provides the delivery product of Embodiment 27 optionally configured to include misting of water such that a hot aerosol is passed over the delivery product and the delivery device further comprises a misting reservoir hydraulically connected to the mister.

Embodiment 29 provides the delivery product of any of Embodiments 22-28 optionally further comprising one or more additional layers attached to the coated substrate and configured to provide at least one of flavor or adjuvant of the one or more herbal extract(s).

Embodiment 30 provides the delivery product of any of Embodiments 22-29 optionally configured such that the coated substrate includes first and second electrodes extending laterally on the coated substrate at first and second longitudinal locations, the first and second electrodes each having an electrical resistance sufficient to conduct current laterally such that at least a portion of the coated substrate can be resistively heated, and the herbal extract or extracts volatilize or entrain in response to the resistive heating.

Embodiment 31 provides a delivery system comprising a coated substrate with one or more coating layers, the one or more coating layers including herbal extract(s), and a heating element for heating the coated substrate to a temperature to volatize or entrain the herbal extract(s) in the one or more coating layers into a vapor or aerosol inhalable by a user.

Embodiment 32 provides the delivery system of Embodiment 31 optionally configured such that the coated substrate is converted into a delivery cartridge configured to maximize surface area of the delivery cartridge and allow for passage of air through delivery cartridge, in order to volatize or entrain herbal extract(s) for inhalation by a user when heat is applied to delivery cartridge or the air passing through the delivery cartridge.

Embodiment 33 provides the delivery system of Embodiment 31 or 32 optionally configured such that the heating element is contained within the delivery device and the delivery cartridge is receivable within a receptacle of the delivery device to heat the delivery cartridge.

Embodiment 34 provides the delivery system of any of Embodiments 31-33 optionally configured such that the heating element is part of a vaporizer or a nebulizer.

Embodiment 35 provides the delivery system of any of Embodiments 31-34 optionally further comprising a mister configured to add a mist to the vapor.

Embodiment 36 provides the delivery system of Embodiment 35 optionally further comprising a misting reservoir hydraulically connected to the mister.

Embodiment 37 provides the delivery system of any of Embodiments 31-36 optionally configured such that the coated substrate includes first and second electrodes extending laterally on the coated substrate at first and second longitudinal locations, the first and second electrodes each having an electrical resistance sufficient to conduct current laterally along the substrate, the substrate having an electrical resistance high enough to conduct current longitudinally between the first and second electrodes and resistively heat at least a portion of the coated substrate in response to the current conducted there through, and the herbal extract(s) volatilizes into a gas or vapor or entrains as an aerosol in response to the resistive heating.

Embodiment 38 provides the delivery system of Embodiment 37 optionally configured such that the heating element includes first and second housing electrodes to deliver current between the first and second electrodes on the substrate to resistively heat at least a portion of the coated substrate.

Embodiment 39 provides a delivery product including a cylindrical structure extending in a longitudinal direction and formed from a substrate of an electrically conductive material. The cylindrical structure can include first and second electrodes extending laterally on the substrate at respective first and second longitudinal locations, the first and second electrodes each having an electrical resistance sufficient to conduct current laterally along the substrate, and a first substrate portion extending longitudinally between the first and second electrodes, the first substrate portion having an electrical resistance high enough to conduct current longitudinally between the first and second electrodes and resistively heat the first substrate portion in response to the current conducted there through. The cylindrical structure can also include a first dose of an herbal extract disposed on the first substrate portion and configured to volatilize or entrain into a gas or vapor or aerosol in response to the resistive heating of the first substrate portion.

Embodiment 40 provides the delivery product of Embodiment 39 optionally configured such that the substrate is rolled to form the cylindrical structure having a spiral cross-section, when viewed from a longitudinal end of the rolled sheet, and can optionally further comprise a plurality of electrically insulating spacers positioned to space apart adjacent layers of the substrate.

Embodiment 41 provides the delivery product of Embodiment 40 optionally configured such that the first and second electrodes are attached to the substrate prior to rolling the substrate to form the cylindrical structure.

Embodiment 42 provides the delivery product of any of Embodiments 39-41 optionally further comprising a housing configured to receive the cylindrical structure within a cavity in the housing, the cavity sized and shaped to correspond to the cylindrical structure, the housing having first and second housing electrodes around a circumference of the cavity and facing inward toward the cavity. The first and second housing electrodes can be positioned longitudinally to respectively contact the first and second electrodes of the cylindrical structure when the cylindrical structure is inserted into the housing, and the first and second housing electrodes can be configured to deliver current between the first and second electrodes of the cylindrical structure.

Embodiment 43 provides the delivery product of any of Embodiments 39-42 optionally configured such that the cylindrical structure further includes a third electrode extending laterally across the cylindrical structure at a third longitudinal location, so that the second electrode is positioned longitudinally between the first and third electrodes; and the third electrode has an electrical resistance small enough to conduct current laterally along the cylindrical structure. The cylindrical structure further includes a second substrate portion extending longitudinally between the second and third electrodes; and the second substrate portion has an electrical resistance sufficient to conduct current longitudinally between the second and third electrodes and resistively heat the second substrate portion in response to the current conducted there through. A second dose of the herbal extract which is the same as or different from the first dose can be disposed on the second substrate portion and configured to volatilize into a gas or vapor or entrain into an aerosol in response to the resistive heating of the second substrate portion.

Embodiment 44 provides the delivery product of Embodiment 43 optionally further comprising a housing configured to receive the cylindrical structure within a cavity in the housing, the cavity sized and shaped to correspond to the cylindrical structure, the housing having first, second, and third housing electrodes around a circumference of the cavity and facing inward toward the cavity, the first, second, and third housing electrodes being positioned longitudinally to respectively contact the first, second, and third electrodes of the cylindrical structure when the cylindrical structure is inserted into the housing, the first and second housing electrodes configured to deliver current between the first and second electrodes of the cylindrical structure, and the second and third housing electrodes configured to deliver current between the second and third electrodes of the cylindrical structure.

Embodiment 45 provides the delivery product of Embodiment 44 optionally further comprising a controller positioned in the housing and configured to deliver current between the first and second housing electrodes to provide the first dose of the herbal extract to a patient, and further configured to deliver current between the second and third housing electrodes to provide second and third doses of the herbal extract to the patient, the herbal extract of the second and third doses being the same as or different from the herbal extract of the first dose and the herbal extracts of the second and third doses being the same or being different.

Embodiment 46 provides the delivery product of Embodiment 45 optionally configured such that the controller delivers current between the first and second housing electrodes at a first time to provide the first dose of the herbal extract to a user and delivers current between the second and third housing electrodes at a second time and third, different from the first time, to provide the second dose and third dose of herbal extract to the user.

Embodiment 47 provides the delivery product of Embodiment 45 optionally configured such that the controller delivers current between the first and second housing electrodes and simultaneously delivers current between the second and third housing electrodes to provide the first, second and doses of herbal extracts to the user at the same time.

Embodiment 48 provides the delivery product of any of Embodiments 44-47 optionally configured such that the housing is elongated and includes a first longitudinal end configured to deliver the vapor or aerosol into a user's mouth.

Embodiment 49 provides the delivery product of any of Embodiments 39-48 optionally configured such that the herbal extract(s) include at least one of a coniferous extract, menthol, nutmeg oil, *Digitalis*, methyl salicylate, acetyl salicylic acid or the methyl ester thereof, tetrahydrocannabinol, cannabidiol, arachidonic acid, a steroid such as budesonide, mometasone or fluticasone, niacin, caffeine, cacao extract, or coca leaf extract. The purified forms of some of these extracts may be purchased as substances previously obtained from herbaceous plants and/or optionally synthetically modified. The non-salt forms, e.g., free bases, free acids and non-complexed neutral forms are preferred for volatilization and/or entrainment as vapors and/or aerosols.

Embodiment 50 provides the delivery product of any of Embodiments 39-49 optionally configured such that the first and second electrodes are formed integrally with the substrate and are thicker than the first substrate portion.

Embodiment 51 provides the delivery product of any of Embodiments 39-50 optionally configured such that the housing further comprises a mister configured to add a mist to the volatized first dose of the one or more herbal extracts.

Embodiment 52 provides the delivery product of Embodiment 51 optionally configured such that the housing further comprises a misting reservoir hydraulically connected to the mister.

Embodiment 53 provides an apparatus including a cylindrical structure extending in a longitudinal direction and formed from a substrate of an electrically conductive material. The cylindrical structure can include a plurality of electrodes extending laterally on the substrate at respective longitudinal locations, each electrode in the plurality having an electrical resistance sufficient to conduct current laterally along the substrate. The cylindrical structure can include at least one substrate portion extending longitudinally between the adjacent electrodes in the plurality, each substrate portion having an electrical resistance sufficient to conduct current longitudinally between the adjacent electrodes and resistively heat the substrate portion in response to the current conducted there through. The cylindrical structure can include herbal extract(s) disposed on each substrate portion and configured to volatilize or entrain into a vapor or aerosol in response to the resistive heating of the substrate portion Embodiment 54 provides the apparatus of Embodiment 53 optionally configured such that the substrate is rolled to form the cylindrical structure having a spiral cross-section, when viewed from a longitudinal end of the rolled sheet, and optionally further comprising a plurality of electrically insulating spacers positioned to space apart adjacent layers of the substrate.

Embodiment 55 provides the apparatus of Embodiment 54 optionally configured such that the first and second electrodes are attached to the substrate prior to rolling the substrate to form the cylindrical structure.

Embodiment 56 provides the apparatus of any of Embodiments 53-55 optionally configured such that a first lateral end of the substrate is connected to a second lateral end of the substrate to form the cylindrical structure having a tubular shape, and each of the plurality of electrodes extend around an exterior circumference of the tubular shape.

Embodiment 57 provides the apparatus of any of Embodiments 53-56 optionally further comprising a housing configured to receive the cylindrical structure within a cavity sized and shaped to receive the cylindrical structure, the housing having a plurality of housing electrodes around a circumference of the cavity and facing inward toward the cavity, each housing electrode being positioned longitudinally to respectively contact a respective electrode of the cylindrical structure when the cylindrical structure is inserted into the housing. Each pair of adjacent housing electrodes can be configured to deliver current between a corresponding pair of adjacent electrodes of the cylindrical structure.

Embodiment 58 provides the apparatus of Embodiment 57 optionally further comprising a controller positioned in the housing and configured to deliver current between adjacent pairs of housing electrodes at sequential times to provide a dose of the corresponding herbal extract to a user at each sequential time, or deliver current between adjacent pairs of housing electrodes simultaneously to provide more than one dose of the corresponding herbal extract(s) to the user at one time.

Embodiment 59 provides the apparatus of any of Embodiments 53-58 optionally configured such that the herbal extract or extracts includes at least one of a coniferous extract, menthol, nutmeg oil, *Digitalis*, methyl salicylate, acetyl salicylic acid or the methyl ester thereof, tetrahydrocannabinol, cannabidiol, arachidonic acid, a steroid such as budesonide, mometasone or fluticasone, niacin, caffeine, cacao extract, or coca leaf extract. The purified forms of some of these extracts may be purchased as substances previously obtained from herbaceous plants and/or optionally synthetically modified. The non-salt forms, e.g., free bases, free acids and non-complexed neutral forms are preferred for volatilization and/or entrainment as vapors and/or aerosols.

Embodiment 60 provides the apparatus of any of Embodiments 53-59 optionally configured such that the housing further comprises a mister configured to add a mist to the volatilized herbal extract or extracts.

Embodiment 61 provides the apparatus of Embodiment 60 optionally configured such that the housing further comprises a misting reservoir hydraulically connected to the mister.

Embodiment 62 provides a method including forming or providing a sheet of conductive material, the sheet extending in longitudinal and lateral dimensions, the sheet having a plurality of contact portions spaced apart longitudinally and extending laterally across the sheet, the sheet having at least one substrate portion extending longitudinally between a pair of adjacent contact portions, the contact portions having a thickness greater than a thickness of the at least one substrate portion. The method including depositing an herbal extract or multiple herbal extracts on the corresponding substrate portion or portions, the herbal extract(s) being configured to volatilize into a vapor or entrain as an aerosol in response to resistive heating of the respective substrate portion, and converting the sheet into a cylindrical structure.

Embodiment 63 provides the method of Embodiment 62 optionally configured such that converting the sheet into a cylindrical structure includes rolling the sheet such that the cylindrical structure has a spiral cross-section, when viewed from a longitudinal end of the rolled sheet. The method can optionally further comprise, as the sheet is rolled, placing a plurality of electrically insulating spacers between adjacent layers of the sheet, the spacers being spaced apart to allow a flow of gas or aerosol there-around.

Embodiment 64 provides the method of Embodiment 62 or 63 optionally configured such that converting the sheet into a cylindrical structure includes connecting a first lateral end of the sheet to a second lateral end of the sheet to form the cylindrical structure having a tubular shape, and each of the plurality of contact portions extends around a circumference of the tubular shape.

Embodiment 65 provides the method of any of Embodiments 62-64 optionally configured such that the cylindrical structure is configured for use as a delivery cartridge.

Embodiment 66 provides the method of any of Embodiments 62-65 wherein the herbal extract(s) includes at least one of a coniferous extract, menthol, nutmeg oil, *Digitalis*, methyl salicylate, acetyl salicylic acid or the methyl ester thereof, tetrahydrocannabinol, cannabidiol, arachidonic acid, a steroid such as budesonide, mometasone or fluticasone, niacin, caffeine, cacao extract, or coca leaf extract. The purified forms of some of these extracts may be purchased as substances previously obtained from herbaceous plants and/or optionally synthetically modified. The non-salt forms, e.g., free bases, free acids and non-complexed neutral forms are preferred for volatilization and/or entrainment as vapors and/or aerosols.

Embodiment 67 provides a method, system, product or apparatus of any one or any combination of Embodiments 1-66, which can be optionally configured such that all steps or elements recited are available to use or select from.

Embodiment 68 provides a method, system, product and/or apparatus for practicing wet extraction and isolation of herbal extract(s) from one or more comminuted herbaceous plant compositions to produce one or more purified herbal extracts and deposition of one or more herbal extract on corresponding portions of a substrate to provide a substrate coated with one or more herbal extracts, the herbal extract(s) being present as overlapping layers on the substrate or as segregated layers on the substrate, the coated substrate being preferably configured to provide a delivery cartridge corresponding to a delivery system wherein the delivery system is configured to volatilize the herbal extract(s) or entrain the herbal extract(s) so as to produce a vapor or aerosol of the herbal extract(s) for administrative delivery by inhalation to a patient.

Embodiment 69 provides a method and product of Embodiment 68 in which the wet extraction and isolation includes formation of a concentrate of the one or more comminuted herbaceous plant compositions in one or more appropriate solvents so as to extract the herbal extract(s) from the composition or compositions and provide one or more solutions of herbal extract(s), concentrating the one or more solutions to form concentrates or optionally crystallizing the herbal extract(s) from the solutions or optionally forming neet oils of the one or more concentrated solutions and depositing and/or casting the one or more crystallized herbal extract(s) and/or one or more oils of herbal extracts and/or one or more concentrates onto the one or more corresponding portions of the substrate.

Embodiment 70 provides a method and product of Embodiments 68 and 69 in which the concentration of the one or more solutions is accomplished by stirred vacuum removal of solvent and the crystallization is accomplished by addition of a non-solvent for the herbal extract(s) to the concentrated solution of herbal extract(s).

Embodiment 71 provides a method, system, product and/or apparatus of Embodiments 68, 69 and/or 70 wherein the herbaceous plant material is pre-treated as described in Embodiments 7-10.

Embodiment 72 provides a coated substrate, a delivery cartridge and/or a delivery system of any of Embodiments 11-66 wherein the substrate coated with one or more overlapping or segregated layer is herbal extract(s) is produced according to the wet extraction methods of Embodiments 68, 69 and/or 70 and optionally by incorporating the pre-treatment of herbaceous plant material according to Embodiments 7-10.

Embodiment 73 provides an apparatus including a cylindrical structure extending in a longitudinal direction and formed from a substrate of an electrically conductive material. The cylindrical structure can include a plurality of electrodes extending laterally on the substrate at respective longitudinal locations, each electrode in the plurality having an electrical resistance sufficient to conduct current laterally along the substrate. The cylindrical structure can include at least one substrate portion extending longitudinally between the adjacent electrodes in the plurality, each substrate portion having an electrical resistance sufficient to conduct current longitudinally between the adjacent electrodes and resistively heat the substrate portion in response to the current conducted there-through. The cylindrical structure can include herbal extract(s) of Embodiments 68-70 disposed on each substrate portion and configured to volatilize into a gas or vapor or to become entrained as an aerosol in air in response to the resistive heating of the substrate portion and an optional flow of air through the cylindrical structure.

STATEMENTS

1. An herbal extract delivery system comprising:
   a coated substrate with one or more coating layers, the one or more coating layers including one or more herbal extracts; and
   a heating element for heating the coated substrate to a temperature to volatize or entrain the one or more herbal extracts on the one or more coating layers into one or more vapors or aerosols inhalable by a user.

2. An herbal extract delivery system of statement 1 further comprising multiple coating layers, each layer being a different herbal extract.

3. An herbal extract delivery system of statement 1 further comprising a control element for the heating element that controls the time and temperature of heating.

4. An herbal extract delivery system of statement 2 further comprising a control element for the heating element that controls the time and temperature of heating.

5. An herbal extract delivery system of statement 3 further comprising multiple coating layers and an arrangement of the control element to volatilize sequentially the multiple layers of herbal extracts.

6. An herbal extract delivery system of statement 4 further comprising multiple coating layers and an arrangement of the control element to volatilize sequentially the multiple layers of herbal extracts.

7. An herbal extract delivery system of statement 2 further comprising overlapping layers in which the layers are ordered by volatilization temperature, the herbal extract with the lowest volatilization temperature being the top layer and the herbal extract with the highest volatilization temperature being the bottom layer adjacent to the substrate.

8. An herbal extract delivery system of statement 3 further comprising overlapping layers in which the layers are ordered by volatilization temperature, the herbal extract with the lowest volatilization temperature being the top layer and the herbal extract with the highest volatilization temperature being the bottom layer adjacent to the substrate.

9. An herbal extract delivery system of statement 4 further comprising overlapping layers in which the layers are ordered by volatilization temperature, the herbal extract with the lowest volatilization temperature being the top layer and the herbal extract with the highest volatilization temperature being the bottom layer adjacent to the substrate.

10. An herbal extract delivery system of statement 5 further comprising overlapping layers in which the layers are ordered by volatilization temperature, the herbal extract with the lowest volatilization temperature being the top layer and the herbal extract with the highest volatilization temperature being the bottom layer adjacent to the substrate.

11. An herbal extract delivery system of statement 6 further comprising overlapping layers in which the layers are ordered by volatilization temperature, the herbal extract with the lowest volatilization temperature being the top layer and the herbal extract with the highest volatilization temperature being the bottom layer adjacent to the substrate.

12. An herbal extract delivery system of statement 2 further comprising segregated layers of herbal extracts having a coterminous arrangement such that the layers are free from overlap.

13. An herbal extract delivery system of statement 3 further comprising segregated layers of herbal extracts having a coterminous arrangement such that the layers are free from overlap.

14. An herbal extract delivery system of statement 4 further comprising segregated layers of herbal extracts having a coterminous arrangement such that the layers are free from overlap.

15. An herbal extract delivery system of statement 5 further comprising segregated layers of herbal extracts having a coterminous arrangement such that the layers are free from overlap.

16. An herbal extract delivery system of statement 6 further comprising segregated layers of herbal extracts having a coterminous arrangement such that the layers are free from overlap.

17. An herbal extract delivery system of statement 1 further comprising herbal extracts of herbaceous plants selected from the group consisting of damiana, blue lotus, mullein, *Lobelia*, peppermint, spearmint, catnip, thyme, sage, wild dagga, lavender, rosemary, *Salvia divinorum*, basil, lemon balm, hops, yerba mate, calea zacatechichi, chamomile, ashwagandha *Eucalyptus*, passion flower, St John's wart, valerian, *Astragalus, Avena sativa*, kinnikinnick, cacao, chago, cinnamon, nutmeg, mace, *Cordyceps*, Don Quai, Gotu Kola, ginger root, *Ginseng*, green tea, kava, maca, moringa leaf, mullein, sacred pink lotus, red raspberry, *Rhodiola*, rooibos, tong kat ali, vanilla, yohimbine, garlic, turmeric, nutmeg, capsaicin, rosemary, *Cannabis*, coniferous trees, yew bush, willow tree, aspen tree, blood root, opium poppy, *Atropa belladonna*, strychnine, *Vinca rosea*, coffee plant, cacao tree and beans (chocolate), coca plant (cocaine), *Nicotinaa tabacum, Camelia sinensis*, monkshood, castor oil, henbane, calabar bean, *Digitalis* sp, autumn *Crocus*, peyote, *Amanita*, orange, lemon, and any other known herbaceous plants which produce known agents having useful medicinal, pharmacological, physiological, beneficial, sensory or other perceived measurable effects on humans.

18. An herbal extract delivery system of statement 2 further comprising herbal extracts of herbaceous plants selected from the group consisting of damiana, blue lotus, mullein, *Lobelia*, peppermint, spearmint, catnip, thyme, sage, wild dagga, lavender, rosemary, *Salvia divinorum*, basil, lemon balm, hops, yerba mate, calea zacatechichi, chamomile, ashwagandha *Eucalyptus*, passion flower, St John's wart, valerian, *Astragalus, Avena sativa*, kinnikinnick, cacao, chago, cinnamon, nutmeg, mace, *Cordyceps*, Don Quai, Gotu Kola, ginger root, *Ginseng*, green tea, kava, maca, moringa leaf, mullein, sacred pink lotus, red raspberry, *Rhodiola*, rooibos, tong kat ali, vanilla, yohimbine, garlic, turmeric, nutmeg, capsaicin, rosemary, *Cannabis*, coniferous trees, yew bush, willow tree, aspen tree, blood root, opium poppy, *Atropa belladonna*, strychnine, *Vinca rosea*, coffee plant, cacao tree and beans (chocolate), coca plant (cocaine), *Nicotinaa tabacum, Camelia sinensis*, monkshood, castor oil, henbane, calabar bean, *Digitalis* sp, autumn *Crocus*, peyote, *Amanita*, orange, lemon, and any other known herbaceous plants which produce known agents having useful medicinal, pharmacological, physiological, beneficial, sensory or other perceived measurable effects on humans.

19. An herbal extract delivery system of statement 7 further comprising herbal extracts of herbaceous plants selected from the group consisting of damiana, blue lotus, mullein, *Lobelia*, peppermint, spearmint, catnip, thyme, sage, wild dagga, lavender, rosemary, *Salvia divinorum*, basil, lemon balm, hops, yerba mate, calea zacatechichi, chamomile, ashwagandha *Eucalyptus*, passion flower, St John's wart, valerian, *Astragalus, Avena sativa*, kinnikinnick, cacao, chago, cinnamon, nutmeg, mace, *Cordyceps*, Don Quai, Gotu Kola, ginger root, *Ginseng*, green tea, kava, maca, moringa leaf, mullein, sacred pink lotus, red raspberry, *Rhodiola*, rooibos, tong kat ali, vanilla, yohimbine, garlic, turmeric, nutmeg, capsaicin, rosemary, *Cannabis*, coniferous trees, yew bush, willow tree, aspen tree, blood root, opium poppy, *Atropa belladonna*, strychnine, *Vinca rosea*, coffee plant, cacao tree and beans (chocolate), coca plant (cocaine), *Nicotinaa tabacum, Camelia sinensis*, monkshood, castor oil, henbane, calabar bean, *Digitalis* sp, autumn *Crocus*, peyote, *Amanita*, orange, lemon, and any other known herbaceous plants which produce known agents having useful medicinal, pharmacological, physiological, beneficial, sensory or other perceived measurable effects on humans.

20. An herbal extract delivery system of statement 12 further comprising herbal extracts of herbaceous plants selected from the group consisting of damiana, blue lotus, mullein, *Lobelia*, peppermint, spearmint, catnip, thyme, sage, wild dagga, lavender, rosemary, *Salvia divinorum*, basil, lemon balm, hops, yerba mate, calea zacatechichi, chamomile, ashwagandha *Eucalyptus*, passion flower, St John's wart, valerian, *Astragalus, Avena sativa*, kinnikinnick, cacao, chago, cinnamon, nutmeg, mace, *Cordyceps*, Don Quai, Gotu Kola, ginger root, *Ginseng*, green tea, kava, maca, moringa leaf, mullein, sacred pink lotus, red raspberry, *Rhodiola*, rooibos, tong kat ali, vanilla, yohimbine, garlic, turmeric, nutmeg, capsaicin, rosemary, *Cannabis*, coniferous trees, yew bush, willow tree, aspen tree, blood root, opium poppy, *Atropa belladonna*, strychnine, *Vinca rosea*, coffee plant, cacao tree and beans (chocolate), coca plant (cocaine), *Nicotinaa tabacum, Camelia sinensis*, monkshood, castor oil, henbane, calabar bean, *Digitalis* sp, autumn *Crocus*, peyote, *Amanita*, orange, lemon, and any other known herbaceous plants which produce known agents having useful medicinal, pharmacological, physiological, beneficial, sensory or other perceived measurable effects on humans.

21. An herbal extract delivery product comprising: a substrate coated with one or more layers of one or more herbal extracts of one or more herbaceous plants.

22. An herbal extract delivery product of statement 21 further comprising a heating element associated with the substrate, the heating element being capable of heating the substrate in a controlled fashion to a selected temperature.

23. An herbal extract delivery product of statement 21 further comprising multiple overlapping layers of individual herbal extracts on the substrate.

24. An herbal extract delivery product of statement 22 further comprising multiple overlapping layers of individual herbal extracts on the substrate.

25. An herbal extract delivery product of statement 23 further comprising an arrangement of the overlapping layers in which the arrangement orders the layers according to the volatilization temperatures of the herbal extracts, the herbal extract with the lowest volatilization temperature being the top layer and the herbal extract with the highest volatilization temperature being the bottom layer adjacent to the substrate.

26. An herbal extract delivery product of statement 24 further comprising an arrangement of the overlapping layers in which the arrangement orders the layers according to the volatilization temperatures of the herbal extracts, the herbal extract with the lowest volatilization temperature being the top layer and the herbal extract with the highest volatilization temperature being the bottom layer adjacent to the substrate.

27. An herbal extract delivery product of statement 21 further comprising multiple segregated layers of individual herbal extracts.

28. An herbal extract delivery product of statement 22 further comprising multiple segregated layers of individual herbal extracts.

29. An herbal extract delivery product of statement 27 wherein the segregated layers of herbal extracts are arranged sequentially on the substrate.

30. An herbal extract delivery product of statement 28 wherein the segregated layers of herbal extracts are arranged sequentially on the substrate.

31. An herbal extract delivery product of statement 23 wherein the herbal extract of one layer differs from the herbal extracts on all other layers.

32. An herbal extract delivery product of statement 27 wherein the herbal extract of one layer differs from the herbal extracts on all other layers.

33. An herbal extract delivery product of statement 21 further comprising herbal thermal extracts of herbaceous plants selected from the group consisting of damiana, blue lotus, mullein, *Lobelia*, peppermint, spearmint, catnip, thyme, sage, wild dagga, lavender, rosemary, *Salvia divinorum*, basil, lemon balm, hops, yerba mate, calea zacatechichi, chamomile, ashwagandha *Eucalyptus*, passion flower, St John's wart, valerian, *Astragalus, Avena sativa*, kinnikinnick, cacao, chago, cinnamon, nutmeg, mace, *Cordyceps*, Don Quai, Gotu Kola, ginger root, *Ginseng*, green tea, kava, maca, moringa leaf, mullein, sacred pink lotus, red raspberry, *Rhodiola*, rooibos, tong kat ali, vanilla, yohimbine, garlic, turmeric, nutmeg, capsaicin, rosemary, *Cannabis*, coniferous trees, yew bush, willow tree, aspen tree, blood root, opium poppy, *Atropa belladonna*, strychnine, *Vinca rosea*, coffee plant, cacao tree and beans (chocolate), coca plant (cocaine), *Nicotinaa tabacum, Camelia sinensis*, monkshood, castor oil, henbane, calabar bean, *Digitalis* sp, autumn *Crocus*, peyote, *Amanita*, orange, lemon, and any other known herbaceous plants which produce known agents having useful medicinal, pharmacological, physiological, beneficial, sensory or other perceived measurable effects on humans.

34. An herbal extract delivery product of statement 23 further comprising herbal thermal extracts of herbaceous plants selected from the group consisting of damiana, blue lotus, mullein, *Lobelia*, peppermint, spearmint, catnip, thyme, sage, wild dagga, lavender, rosemary, *Salvia divinorum*, basil, lemon balm, hops, yerba mate, calea zacatechichi, chamomile, ashwagandha *Eucalyptus*, passion flower, St John's wart, valerian, *Astragalus, Avena sativa*, kinnikinnick, cacao, chago, cinnamon, nutmeg, mace, *Cordyceps*, Don Quai, Gotu Kola, ginger root, *Ginseng*, green tea, kava, maca, moringa leaf, mullein, sacred pink lotus, red raspberry, *Rhodiola*, rooibos, tong kat ali, vanilla, yohimbine, garlic, turmeric, nutmeg, capsaicin, rosemary, *Cannabis*, coniferous trees, yew bush, willow tree, aspen tree, blood root, opium poppy, *Atropa belladonna*, strychnine, *Vinca rosea*, coffee plant, cacao tree and beans (chocolate), coca plant (cocaine), *Nicotinaa tabacum, Camelia sinensis*, monkshood, castor oil, henbane, calabar bean, *Digitalis* sp, autumn *Crocus*, peyote, *Amanita*, orange, lemon, and any other known herbaceous plants which produce known agents having useful medicinal, pharmacological, physiological, beneficial, sensory or other perceived measurable effects on humans.

35. An herbal extract delivery product of statement 27 further comprising herbal thermal extracts of herbaceous plants selected from the group consisting of damiana, blue lotus, mullein, *Lobelia*, peppermint, spearmint, catnip, thyme, sage, wild dagga, lavender, rosemary, *Salvia divinorum*, basil, lemon balm, hops, yerba mate, calea zacatechichi, chamomile, ashwagandha *Eucalyptus*, passion flower, St John's wart, valerian, *Astragalus, Avena sativa*, kinnikinnick, cacao, chago, cinnamon, nutmeg, mace, *Cordyceps*, Don Quai, Gotu Kola, ginger root, *Ginseng*, green tea, kava, maca, moringa leaf, mullein, sacred pink lotus, red raspberry, *Rhodiola*, rooibos, tong kat ali, vanilla, yohimbine, garlic, turmeric, nutmeg, capsaicin, rosemary, *Cannabis*, coniferous trees, yew bush, willow tree, aspen tree, blood root, opium poppy, *Atropa belladonna*, strychnine, *Vinca rosea*, coffee plant, cacao tree and beans (chocolate), coca plant (cocaine), *Nicotinaa tabacum, Camelia sinensis*, monkshood, castor oil, henbane, calabar bean, *Digitalis* sp, autumn *Crocus*, peyote, *Amanita*, orange, lemon, and any other known herbaceous plants which produce known agents having useful medicinal, pharmacological, physiological, beneficial, sensory or other perceived measurable effects on humans.

36. An herbal extract delivery product of statement 21, comprising:
  A cylindrical structure extending in a longitudinal direction and formed from a substrate of an electrically conductive material, the cylindrical structure comprising:
    At least a first set of electrodes extending longitudinally and laterally on the substrate, the at least first set of electrodes having an electrical resistance sufficient to conduct current laterally along the substrate;
    An at least first substrate portion coterminous with the at least first set of electrodes, the first substrate portion having an electrical resistance high enough to conduct current from the first set of electrodes and resistively heat the first substrate portion in response to the current conducted there through; and
    At least a first dose of an herbal extract disposed on the first substrate portion and configured to volatilize or entrain into a gas or aerosol in response to the resistive heating of the first substrate portion.

37. An herbal extract delivery product of statement 36 wherein multiple herbal 1 extracts are present and the substrate and extracts are arranged as overlapping layers in which the arrangement orders the layers according to the volatilization temperatures of the herbal extracts, the herbal extract with the lowest volatilization temperature being the top layer and the herbal extract with the highest volatilization temperature being the bottom layer adjacent to the substrate.

38. An herbal extract delivery product of statement 36 wherein multiple herbal extracts are present and the substrate and extracts are arranged as multiple segregated layers of individual herbal extracts distributed sequentially on the substrate.

39. An apparatus, comprising:
  A cylindrical structure extending in a longitudinal direction and formed from a substrate of an electrically conductive material, the cylindrical structure comprising:
    A plurality of electrodes extending laterally on the substrate at respective longitudinal locations, each electrode in the plurality having an electrical resistance sufficient to conduct current laterally along the substrate;
    at least one substrate portion extending longitudinally between the adjacent electrodes in the plurality, each substrate portion having an electrical resistance sufficient to conduct current longitudinally between the adjacent electrodes and resistively heat the substrate portion in response to the current conducted there through; and
    At least one herbal extract disposed on at least one substrate portion and configured to volatilize or entrain into a vapor or aerosol in response to the resistive heating of the substrate portion.

40. An apparatus of statement 39 wherein multiple herbal extracts are present and the substrate and extracts are arranged as overlapping layers in which the arrangement orders the layers according to the volatilization temperatures of the herbal extracts, the herbal extract with the lowest volatilization temperature being the top layer and the herbal extract with the highest volatilization temperature being the bottom layer adjacent to the substrate.

41. An apparatus of statement 39 wherein multiple herbal extracts are present and the substrate and the extracts are arranged as multiple segregated layers of individual herbal extracts distributed sequentially on the substrate.

42. A method of purifying at least one or more herbal extracts from one or more medicinal herbs, the method comprising:
  Heating an appropriate herbaceous plant part to a first temperature to volatilize the herbal extract into a first vapor; and
  Condensing the first vapor onto a substrate to form a first coating or the herbal extract.

43. A method of statement 42 further comprising sequentially heating appropriate multiple herbaceous plant parts to volatilize sequentially multiple herbal extracts and condensing sequentially the multiple vapors onto a substrate to form sequential layers of herbal extracts on the substrate.

44. A method of making An herbal extract delivery cartridge, the method comprising:
  Heating an appropriate herbaceous plant part to a temperature to volatize an herbal extract into a vapor;
  Condensing the vapor onto a substrate to form a coating of herbal extract on the substrate; and
  Converting the coated substrate into a three-dimensional structure configured for use as An herbal extract delivery cartridge.

45. A method according to statement 44 further comprising:
  Providing a substrate that is a sheet of conductive material, the sheet extending in longitudinal and lateral dimensions, the sheet having at least one substrate portion extending longitudinally between a pair of adjacent contact portions;
  Depositing at least one herbal extract on the substrate portion, the herbal extract configured to volatilize into a vapor in response to resistive heating of the respective substrate portion.

46. A method of statement 45 comprising converting the sheet into a cylindrical structure.

47. A method of statement 45 further comprising depositing as overlapping layers a multiplicity of herbal extracts.

48. A method of statement 45 further comprising
  Sequentially volatilizing herbal extracts from a multiplicity of herbaceous plants into vapors, Sequentially depositing the herbal extract vapors on a moving cooling belt to form solid substances of the herbal extracts on the belt, Sequentially stripping the solid substances from the cooling belt and heating the stripped solid substances to form liquid herbal extracts;

Sequentially transferring the liquid herbal t extracts into a heated container,

Sequentially depositing the liquid herbal extracts from the heated container to the sheet of conductive material that is optionally cooled, Forming uniform layers of the deposited herbal extracts on the sheet.

49. A method of statement 48 further comprising forming overlapping layers of the deposited herbal extracts.

50. A method of statement 48 further comprising forming sequential layers of the deposited herbal extracts.

51. A method of statement 42 further comprising herbal extracts of herbaceous plants selected from the group consisting of damiana, blue lotus, mullein, *Lobelia*, peppermint, spearmint, catnip, thyme, sage, wild dagga, lavender, rosemary, *Salvia divinorum*, basil, lemon balm, hops, yerba mate, calea zacatechichi, chamomile, ashwagandha *Eucalyptus*, passion flower, St John's wart, valerian, *Astragalus, Avena sativa*, kinnikinnick, cacao, chago, cinnamon, nutmeg, mace, *Cordyceps*, Don Quai, Gotu Kola, ginger root, *Ginseng*, green tea, kava, maca, moringa leaf, mullein, sacred pink lotus, red raspberry, *Rhodiola*, rooibos, tong kat ali, vanilla, yohimbine, garlic, turmeric, nutmeg, capsaicin, rosemary, *Cannabis*, coniferous trees, yew bush, willow tree, aspen tree, blood root, opium poppy, *Atropa belladonna*, strychnine, *Vinca rosea*, coffee plant, cacao tree and beans (chocolate), coca plant (cocaine), *Nicotinaa tabacum, Camelia sinensis*, monkshood, castor oil, henbane, calabar bean, *Digitalis* sp, autumn *Crocus*, peyote, *Amanita*, orange, lemon, and any other known herbaceous plants which produce known agents having useful medicinal, pharmacological, physiological, beneficial, sensory or other perceived measurable effects on humans.

52. A method of statement 44 further comprising herbal extracts of herbaceous plants selected from the group consisting of damiana, blue lotus, mullein, *Lobelia*, peppermint, spearmint, catnip, thyme, sage, wild dagga, lavender, rosemary, *Salvia divinorum*, basil, lemon balm, hops, yerba mate, calea zacatechichi, chamomile, ashwagandha *Eucalyptus*, passion flower, St John's wart, valerian, *Astragalus, Avena sativa*, kinnikinnick, cacao, chago, cinnamon, nutmeg, mace, *Cordyceps*, Don Quai, Gotu Kola, ginger root, *Ginseng*, green tea, kava, maca, moringa leaf, mullein, sacred pink lotus, red raspberry, *Rhodiola*, rooibos, tong kat ali, vanilla, yohimbine, garlic, turmeric, nutmeg, capsaicin, rosemary, *Cannabis*, coniferous trees, yew bush, willow tree, aspen tree, blood root, opium poppy, *Atropa belladonna*, strychnine, *Vinca rosea*, coffee plant, cacao tree and beans (chocolate), coca plant (cocaine), *Nicotinaa tabacum, Camelia sinensis*, monkshood, castor oil, henbane, calabar bean, *Digitalis* sp, autumn *Crocus*, peyote, *Amanita*, orange, lemon, and any other known herbaceous plants which produce known agents having useful medicinal, pharmacological, physiological, beneficial, sensory or other perceived measurable effects on humans.

53. A method for producing a substrate coated with one or more herbal extracts, comprising
   a. Comminuting herbaceous plant material to produce particulate material
   b. Extracting the particulate plant material with a solvent in which the herbal extract is soluble to produce a solution;
   c. Concentrating the solution to produce a concentrate;
   d. Depositing the concentrate on the substrate; and,
   e. Evaporating the solvent from the concentrate to produce a coating of the herbal extract on the substrate;
   f. Optionally repeating steps a-e to produce multiple layers of herbal extracts on the substrate.

54. A method according to statement 53 further comprising preforming steps a-e on multiple different herbaceous plant materials to product multiple layers of herbal extracts on the substrate.

55. A method of statement 54 further comprising forming overlapping layers of the deposited herbal extracts.

56. A method of statement 54 further comprising forming sequential layers of the deposited herbal extracts.

57. A method of statement 53 further comprising herbal extracts of herbaceous plants selected from the group consisting of damiana, blue lotus, mullein, *Lobelia*, peppermint, spearmint, catnip, thyme, sage, wild dagga, lavender, rosemary, *Salvia divinorum*, basil, lemon balm, hops, yerba mate, calea zacatechichi, chamomile, ashwagandha *Eucalyptus*, passion flower, St John's wart, valerian, *Astragalus, Avena sativa*, kinnikinnick, cacao, chago, cinnamon, nutmeg, mace, *Cordyceps*, Don Quai, Gotu Kola, ginger root, *Ginseng*, green tea, kava, maca, moringa leaf, mullein, sacred pink lotus, red raspberry, *Rhodiola*, rooibos, tong kat ali, vanilla, yohimbine, garlic, turmeric, nutmeg, capsaicin, rosemary, *Cannabis*, coniferous trees, yew bush, willow tree, aspen tree, blood root, opium poppy, *Atropa belladonna*, strychnine, *Vinca rosea*, coffee plant, cacao tree and beans (chocolate), coca plant (cocaine), *Nicotinaa tabacum, Camelia sinensis*, monkshood, castor oil, henbane, calabar bean, *Digitalis* sp, autumn *Crocus*, peyote, *Amanita*, orange, lemon, and any other known herbaceous plants which produce known agents having useful medicinal, pharmacological, physiological, beneficial, sensory or other perceived measurable effects on humans.

MISCELLANEOUS CHARACTERIZATIONS

The foregoing detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The foregoing description is intended to be illustrative, and not restrictive. For example, the above-described examples, statements and the embodiments (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An herbal extract delivery product comprising:
a cylindrical structure extending in a longitudinal direction and formed from a substrate of an electrically conductive material, the substrate being rolled to provide a spiral cross-section arrangement of spirally arranged strata of substrate, and at least a first section of the substrate being coated on one side thereof with at least one coating layer of at least one herbal extract, the cylindrical structure comprising:
at least a first set of electrodes extending longitudinally and laterally on an uncoated side of the substrate, the at least first set of electrodes having an electrical resistance sufficient to conduct current laterally along the substrate;
the first substrate section being coterminous with the at least first set of electrodes, the first substrate section having an electrical resistance high enough to conduct current from the first set of electrodes and resistively heat the first substrate section in response to the current conducted there through;
a plurality of electrically insulating spacers positioned to space apart adjacent strata of the spiral arranged substrate;
a control element for the electrodes that controls the time and temperature of heating; and the at least one coating layer of at least one herbal extract is configured to volatilize or entrain into a gas or aerosol in response to the resistive heating of the first substrate section.

2. An herbal extract delivery product of claim 1 wherein multiple coating layers are present, each layer being a different herbal extract.

3. An herbal extract delivery product of claim 2 wherein the multiple coating layers are segregated and have a coterminous arrangement such that the layers are free from overlap.

4. An herbal extract delivery product of claim 3 having multiple pairs of electrodes, each pair connected to a different substrate section corresponding to a different coating layer and having an arrangement of the control element to volatilize sequentially the multiple layers of herbal extracts.

5. An herbal extract delivery product of claim 2 having an arrangement of the control element to volatilize sequentially the multiple layers of herbal extracts.

6. An herbal extract delivery product of claim 2 having overlapping layers of different herbal extracts, the layers being arranged by volatilization temperature of the herbal extract with the herbal extract having the lowest volatilization temperature being the top layer and the herbal extract having the highest volatilization temperature being the bottom layer adjacent to the substrate surface.

7. An herbal extract delivery product of claim 1 wherein the at least one herbal extract is obtained from an herbaceous plant selected from the group consisting of damiana, blue lotus, mullein, *Lobelia*, peppermint, spearmint, catnip, thyme, sage, wild dagga, lavender, rosemary, *Salvia divinorum*, basil, lemon balm, hops, yerba mate, calea zacatechichi, chamomile, ashwagandha *Eucalyptus*, passion flower, St John's wart, valerian, *Astragalus, Avena sativa*, kinnikinnick, cacao, chago, cinnamon, nutmeg, mace, *Cordyceps*, Don Quai, Gotu Kola, ginger root, *Ginseng*, green tea, kava, maca, moringa leaf, mullein, sacred pink lotus, red raspberry, *Rhodiola*, rooibos, tong kat ali, vanilla, yohimbine, garlic, turmeric, nutmeg, capsaicin, rosemary, *Cannabis*, coniferous trees, yew bush, willow tree, aspen tree, blood root, opium poppy, *Atropa belladonna*, strychnine, *Vinca rosea*, coffee plant, cacao tree and beans, coca plant, *Nicotinaa tabacum, Camelia sinensis*, monkshood, castor oil, henbane, calabar bean, *Digitalis* sp, autumn *Crocus*, peyote, *Amanita*, orange, lemon, and any other known herbaceous plant which produces a known agent having useful medicinal, pharmacological, physiological, beneficial, sensory or other perceived measurable effects on humans and any combination thereof.

8. An herbal extract delivery product of claim 1 wherein the aerosol or vapor is inhalable by a user.

9. A method for producing a substrate coated on one side with at least one herbal extract, comprising comminuting herbaceous plant material to produce particulate material;
extracting the particulate plant material with a solvent in which the herbal extract is soluble to produce a solution;
concentrating the solution to produce a concentrate;
depositing the concentrate on one side of the substrate thereby producing a coated side and an uncoated side of the substrate; and,
evaporating the solvent from the concentrate to produce at least one coating layer of the herbal extract on the coated side of the substrate;
attaching at least one set of electrodes longitudinally and laterally on the uncoated side of the substrate;
positioning a plurality of electrically insulating spacers on the uncoated side of the substrate and rolling the coated substrate so as to produce a cylindrical structure having a spiral cross-section arrangement of successive strata of substrate which strata are spaced apart by the insulating spacers.

10. A method of claim 9 wherein the at least one herbal extract is obtained from an herbaceous plant selected from the group consisting of damiana, blue lotus, mullein, *Lobelia*, peppermint, spearmint, catnip, thyme, sage, wild dagga, lavender, rosemary, *Salvia* divinorum, basil, lemon balm, hops, yerba mate, calea zacatechichi, chamomile, ashwagandha *Eucalyptus*, passion flower, St John's wart, valerian, *Astragalus, Avena sativa*, kinnikinnick, cacao, chago, cinnamon, nutmeg, mace, *Cordyceps*, Don Quai, Gotu Kola, ginger root, *Ginseng*, green tea, kava, maca, moringa leaf, mullein, sacred pink lotus, red raspberry, *Rhodiola*, rooibos, tong kat ali, vanilla, yohimbine, garlic, turmeric, nutmeg, capsaicin, rosemary, *Cannabis*, coniferous trees, yew bush, willow tree, aspen tree, blood root, opium poppy, *Atropa belladonna*, strychnine, *Vinca rosea*, coffee plant, cacao tree and beans, coca plant, *Nicotinaa tabacum, Camelia sinensis*, monkshood, castor oil, henbane, calabar bean, *Digitalis* sp, autumn *Crocus*, peyote, *Amanita*, orange, lemon, and any other known herbaceous plant which produces a known agent having useful medicinal, pharmacological, physiological, beneficial, sensory or other perceived measurable effects on humans and any combination thereof.

11. A method according to claim 9 wherein the steps of comminuting, extracting, concentrating, depositing and evaporating are repeated one or more times with different herbaceous plant materials to produce multiple coating layers of herbal extracts on the substrate.

* * * * *